(12) United States Patent
Ochsner et al.

(10) Patent No.: US 8,895,241 B2
(45) Date of Patent: Nov. 25, 2014

(54) **APTAMERS FOR *CLOSTRIDIUM DIFFICILE* DIAGNOSTICS**

(75) Inventors: Urs Ochsner, Denver, CO (US);
Evaldas Katilius, Superior, CO (US);
Nebojsa Janjic, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 143 days.

(21) Appl. No.: 13/417,035

(22) Filed: Mar. 9, 2012

(65) Prior Publication Data

US 2012/0231467 A1   Sep. 13, 2012

Related U.S. Application Data

(60) Provisional application No. 61/451,227, filed on Mar. 10, 2011.

(51) Int. Cl.
*C12Q 1/68* (2006.01)
*C12N 15/115* (2010.01)
*C07H 21/02* (2006.01)
*C07H 21/04* (2006.01)

(52) U.S. Cl.
CPC .......... *C12N 15/115* (2013.01); *C12N 2310/16* (2013.01)
USPC ............................ 435/6.1; 536/23.1; 536/24.5

(58) Field of Classification Search
CPC ............ A61K 35/74; C12Q 1/68; C12Q 1/04; C12Q 2525/205; C12Q 1/00; C12Q 1/689; C12N 15/113; C12N 2310/16; C12N 15/115; C12N 2310/335; C12N 15/1048; C08L 69/00; C07H 21/04; C07H 19/073; C07H 19/06; C07H 19/10; C07H 19/173; C07H 1/00; C07H 21/00
See application file for complete search history.

(56) References Cited

U.S. PATENT DOCUMENTS

| | | | |
|---|---|---|---|
| 2009/0004667 A1* | 1/2009 | Zichi et al. ....................... 435/6 |
| 2009/0163536 A1 | 6/2009 | Guiles et al. | |
| 2009/0215032 A1* | 8/2009 | White et al. ...................... 435/6 |
| 2010/0035247 A1 | 2/2010 | Burton | |
| 2010/0317723 A1 | 12/2010 | Lee et al. | |
| 2011/0256535 A1* | 10/2011 | Dolinger et al. .............. 435/6.11 |
| 2013/0034847 A1* | 2/2013 | Kojic et al. .................... 435/6.1 |

OTHER PUBLICATIONS

Hicke, B.J. and Stephens, A. W., "Escort aptamers: a delivery service for diagnostics and therapy", J. Clin. Invest. 106(8): 923-928 (2000).
International Search Report and Written Opinion issued Aug. 14, 2012 in PCT/US2012/028632.

* cited by examiner

*Primary Examiner* — Dana Shin
(74) *Attorney, Agent, or Firm* — Swanson & Bratschun, L.L.C.

(57) ABSTRACT

The present disclosure relates generally to the field of nucleic acids and, more particularly, to aptamers capable of binding to toxins produced by *Clostridium difficile*; diagnostic kits and methods comprising such aptamers; and methods of making and using such aptamers.

6 Claims, 16 Drawing Sheets

TOXIN A rTcdA 2250-2709 (57.1 kDa) protein

PCR with tcdA-6 + tcdA-2 tcdA 1,375 bp

FIG. 1A

TOXIN B

FIG. 1B

BINARY TOXIN A CHAIN rCdtA 35-463 (54.7 kDa) protein

PCR with cdtA-1 + cdtA-2 cdtA 1,300 bp (kb)
3.0
2.0
1.6
1.0 kDa
260
160
110
80
60
50
40
30
20
15
10

FIG. 1C

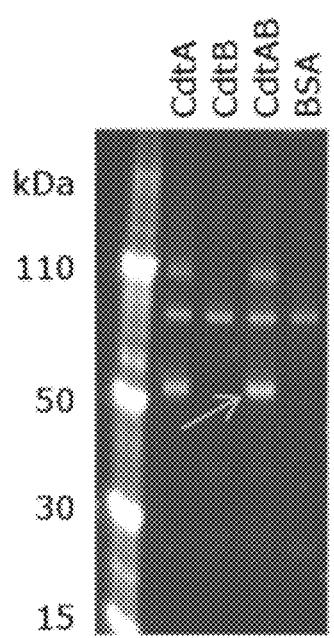 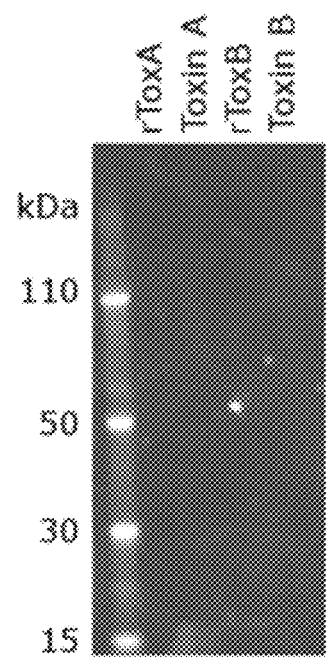
FIG. 2C
FIG. 2D

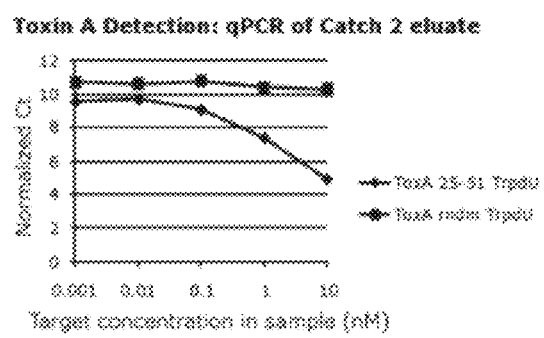 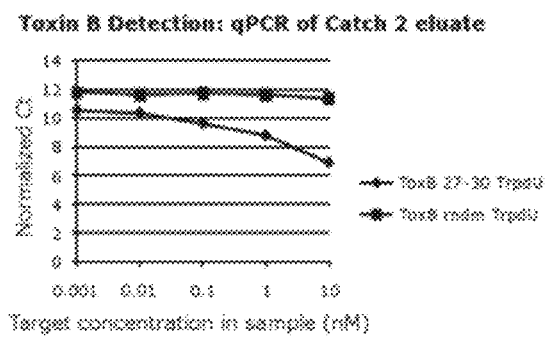
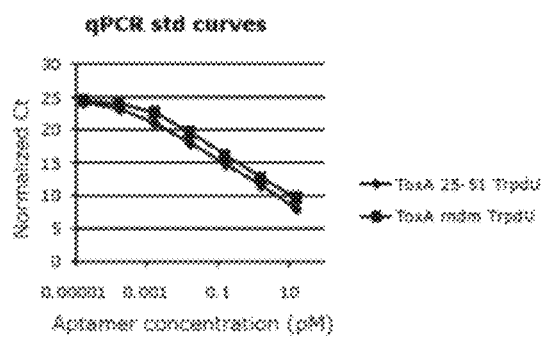 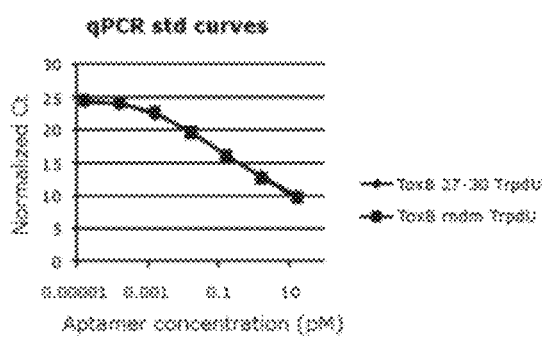
FIG. 4A  FIG. 4B wherein

R'''' is selected from the group consisting of a branched or linear lower alkyl (C1-C20); hydroxyl (OH), halogen (F, Cl, Br, I); nitrile (CN); boronic acid ($BO_2H_2$); carboxylic acid (COOH); carboxylic acid ester (COOR'''); primary amide ($CONH_2$); secondary amide (CONHR'); tertiary amide (CONR'R''); sulfonamide ($SO_2NH_2$); N-alkylsulfonamide (SONHR');

wherein

R', R''' are independently selected from a group consisting of a branched or linear lower alkyl (C1-C2)); phenyl (C6H5); an R'''' substituted phenyl ring (R''''C6H4); wherein R'''' is defined above; a carboxylic acid (COOH); a carboxylic acid ester (COOR''''); wherein R'''' is a branched or linear lower alkyl (C1-C20); and cycloalkyl; wherein R' = R''' = $(CH_2)_n$;

wherein n =2-10.

FIG. 9 continued

SEQUENCE LISTING

```
<160> NUMBER OF SEQ ID NOS: 170

<210> SEQ ID NO 1
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 1
aannccnanc cnanncanca cnnncnnaga nnanncnang                           40

<210> SEQ ID NO 2
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 2
gncanngngc cccacgncan nancngacnn cgacnaacga                           40

<210> SEQ ID NO 3
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 3
acnngnagna gcccnnaann gggnngcgnc ggcannangg                           40

<210> SEQ ID NO 4
<211> LENGTH: 40
<212> TYPE: DNA
<213> ORGANISM: Artificial Sequence
```

```
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 4
cncgnnaggg nnnanccaan accgnggngc cnnaacnaaa                                40

<210> SEQ ID NO 5
<211> LENGTH: 16
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(1)
<223> OTHER INFORMATION: n = 5-tryptaminocarboxyamide-dU
<220> FEATURE:
<221> NAME/KEY: misc_feature
<222> LOCATION: (3)..(3)
<223> OTHER INFORMATION: n = 5-tryptaminocarboxyamide-dU
<220> FEATURE:
<221> NAME/KEY: misc_feature
<222> LOCATION: (5)..(6)
<223> OTHER INFORMATION: n = A, G, C, or 5-tryptaminocarboxyamide-dU
<220> FEATURE:
<221> NAME/KEY: misc_feature
<222> LOCATION: (8)..(10)
<223> OTHER INFORMATION: n = 5-tryptaminocarboxyamide-dU
<220> FEATURE:
<221> NAME/KEY: misc_feature
<222> LOCATION: (12)..(13)
<223> OTHER INFORMATION: n = A, G, C, or 5-tryptaminocarboxyamide-dU
<220> FEATURE:
<221> NAME/KEY: misc_feature
<222> LOCATION: (15)..(15)
<223> OTHER INFORMATION: n = A, G, C, or 5-tryptaminocarboxyamide-dU
<220> FEATURE:
<221> NAME/KEY: misc_feature
<222> LOCATION: (16)..(16)
<223> OTHER INFORMATION: n = 5-tryptaminocarboxyamide-dU

<400> SEQUENCE: 5
nananncnnn cnncnn                                                         16

<210> SEQ ID NO 6
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 6
agcannaaan nanagacnnn cgncancgnc cccnnnnggn                                40

<210> SEQ ID NO 7
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU
```

-continued

```
<400> SEQUENCE: 7
ancncncaca nnanagacnn ncnncanggn ccnccngaga                              40

<210> SEQ ID NO 8
<211> LENGTH: 32
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(32)
<223> OTHER INFORMATION: n = 5-tryptaminocarboxyamide-dU

<400> SEQUENCE: 8
ngccnaaacc nanaaccnnn ccacgngnac nn                                     32

<210> SEQ ID NO 9
<211> LENGTH: 39
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(39)
<223> OTHER INFORMATION: 5-tryptaminocarboxyamide-dU

<400> SEQUENCE: 9
gnanancaac ncgncanggn agcgnaannc nagcnnaga                              39

<210> SEQ ID NO 10
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 10
ccngacgggc gaggnnccaa cnnacnnccg ncacnanngc                             40

<210> SEQ ID NO 11
<211> LENGTH: 10
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(10)
<223> OTHER INFORMATION: n = 5-(2-naphthylmethyl)carboxyamide

<400> SEQUENCE: 11 naaagnaggn                                                              10

<210> SEQ ID NO 12
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
```

```
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 12
cgcangngnn cnganacacn ggccnaaagn aggncngnag                           40

<210> SEQ ID NO 13
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 13
ccgnncnaan accaanggan aaagnaggna ggagcncgca                           40

<210> SEQ ID NO 14
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 14
naccaganag nnanaanacg cnggcnaaag naggnacnaa                           40

<210> SEQ ID NO 15
<211> LENGTH: 13
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (2)..(3)
<223> OTHER INFORMATION: n = 5-(2-naphthylmethyl)carboxyamide
<220> FEATURE:
<221> NAME/KEY: misc_feature
<222> LOCATION: (4)..(4)
<223> OTHER INFORMATION: n = A or G
<220> FEATURE:
<221> NAME/KEY: misc_feature
<222> LOCATION: (5)..(5)
<223> OTHER INFORMATION: n = 5-(2-naphthylmethyl)carboxyamide
<220> FEATURE:
<221> NAME/KEY: misc_feature
<222> LOCATION: (7)..(7)
<223> OTHER INFORMATION: n = A or C
<220> FEATURE:
<221> NAME/KEY: misc_feature
<222> LOCATION: (8)..(8)
<223> OTHER INFORMATION: n = g or 5-(2-naphthylmethyl)carboxyamide
<220> FEATURE:
<221> NAME/KEY: misc_feature
<222> LOCATION: (9)..(9)
<223> OTHER INFORMATION: n = 5-(2-naphthylmethyl)carboxyamide
<220> FEATURE:
<221> NAME/KEY: misc_feature
<222> LOCATION: (11)..(11)
<223> OTHER INFORMATION: n = 5-(2-naphthylmethyl)carboxyamide
```

```
<400> SEQUENCE: 15
gnnnncnnnc nga                                                          13

<210> SEQ ID NO 16
<211> LENGTH: 38
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(38)
<223> OTHER INFORMATION: n = 5-(2-naphthylmethyl)carboxyamide

<400> SEQUENCE: 16
cnaaangaag nngncagncn gacgccagng cgnaccgn                                38

<210> SEQ ID NO 17
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 17
ngcgnacccg cngnngncag ncngagagan cggcnaagaa                              40

<210> SEQ ID NO 18
<211> LENGTH: 39
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(39)
<223> OTHER INFORMATION: n = 5-(2-naphthylmethyl)carboxyamide

<400> SEQUENCE: 18
cnagcngcan accccacgnn gncagncnga gcgcccacn                               39

<210> SEQ ID NO 19
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 19
ngccngccca ccngnngnca gncngagagc nanccaaaca                              40

<210> SEQ ID NO 20
<211> LENGTH: 39
<212> TYPE: DNA
<213> ORGANISM: Artificial Sequence
<220> FEATURE:
```

```
<223> OTHER INFORMATION: Modifications are 5-(2-naphthylmethyl)
      carboxyamide
<220> FEATURE:
<221> NAME/KEY: misc_feature
<222> LOCATION: (1)..(39)
<223> OTHER INFORMATION: n = 5-(2-naphthylmethyl)carboxyamide

<400> SEQUENCE: 20
cangccngca naccacacgn ngnnagncng agggnnagg                    39

<210> SEQ ID NO 21
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 21
ggnaccnacc cgcagngnna ncanncngac cgcgacnnnn                   40

<210> SEQ ID NO 22
<211> LENGTH: 39
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(39)
<223> OTHER INFORMATION: n = 5-(2-naphthylmethyl)carboxyamide

<400> SEQUENCE: 22
cngnnanccg ncngacaccn accnaccgga gnaagancc                    39

<210> SEQ ID NO 23
<211> LENGTH: 19
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(19)
<223> OTHER INFORMATION: n = 5-(2-naphthylmethyl)carboxyamide

<400> SEQUENCE: 23
cgggncgnga cagancgca                                          19

<210> SEQ ID NO 24
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 24
cgagcgggnc gngacaganc gcagagcgaa ggcnnacnac                   40
```

<210> SEQ ID NO 25
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 25 ncnganggggc caacaaangn ccgggncgng acagancgca                              40

<210> SEQ ID NO 26
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 26
gcngaggccg ngcncannaa nngaacnnag aanancccna                               40

<210> SEQ ID NO 27
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 27
accgcnaaag naggncacgn ncnaanaccc ngggaggngn                               40

<210> SEQ ID NO 28
<211> LENGTH: 21
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(1)
<223> OTHER INFORMATION: n = 5-(2-naphthylmethyl)carboxyamide
<220> FEATURE:
<221> NAME/KEY: misc_feature
<222> LOCATION: (10)..(11)
<223> OTHER INFORMATION: n = 5-(2-naphthylmethyl)carboxyamide
<220> FEATURE:
<221> NAME/KEY: misc_feature
<222> LOCATION: (12)..(12)
<223> OTHER INFORMATION: n = A, G, C, or 5-(2-naphthylmethyl)
      carboxyamide
<220> FEATURE:
<221> NAME/KEY: misc_feature
<222> LOCATION: (13)..(13)
<223> OTHER INFORMATION: n = 5-(2-naphthylmethyl)carboxyamide
<220> FEATURE:
<221> NAME/KEY: misc_feature
<222> LOCATION: (17)..(17)
<223> OTHER INFORMATION: n = 5-(2-naphthylmethyl)carboxyamide -continued

```
<220> FEATURE:
<221> NAME/KEY: misc_feature
<222> LOCATION: (19)..(19)
<223> OTHER INFORMATION: n = 5-(2-naphthylmethyl)carboxyamide

<400> SEQUENCE: 28
naccgaacgn nnncagncng a                                            21

<210> SEQ ID NO 29
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 29
gcngccnacc gaacgnngnc agncngagcg ancgaacnng                        40

<210> SEQ ID NO 30
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 30
agccacgnac anaccgaacg nnancagncn gacgcngnga                        40

<210> SEQ ID NO 31
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 31
ccgngcanac ccccngnng ncagncngac ggccagacac                         40

<210> SEQ ID NO 32
<211> LENGTH: 10
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(1)
<223> OTHER INFORMATION: n = C or 5-tyrosylcarboxyamide-dU
<220> FEATURE:
<221> NAME/KEY: misc_feature
<222> LOCATION: (2)..(3)
<223> OTHER INFORMATION: n = 5-tyrosylcarboxyamide-dU
<220> FEATURE:
<221> NAME/KEY: misc_feature
<222> LOCATION: (4)..(5)
<223> OTHER INFORMATION: n = C or G
```

```
<220> FEATURE:
<221> NAME/KEY: misc_feature
<222> LOCATION: (6)..(6)
<223> OTHER INFORMATION: n = 5-tyrosylcarboxyamide-dU
<220> FEATURE:
<221> NAME/KEY: misc_feature
<222> LOCATION: (10)..(10)
<223> OTHER INFORMATION: n = A or 5-tyrosylcarboxyamide-dU

<400> SEQUENCE: 32 nnnnnngaan                                                               10

<210> SEQ ID NO 33
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 33
nannnccnna aggcnnggng aaaaccgcnn nncggnngcg                               40

<210> SEQ ID NO 34
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 34
nggaccacna nccncccca cnnnnncgng aacnngagnn                                40

<210> SEQ ID NO 35
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 35
nggancacgn anncccacnn accnnccnga aanagcannn                               40

<210> SEQ ID NO 36
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 36 acnggngaa anncacnnnc ngccagcanc nanncccgcn                                40

<210> SEQ ID NO 37
```

```
<211> LENGTH: 43
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(43)
<223> OTHER INFORMATION: n = 5-tyrosylcarboxyamide-dU

<400> SEQUENCE: 37
nnggcacgaa gnanngacnn ngaanngcng aaacancnnn ncn                    43

<210> SEQ ID NO 38
<211> LENGTH: 35
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(35)
<223> OTHER INFORMATION: n = 5-tyrosylcarboxyamide-dU

<400> SEQUENCE: 38
nggacaccna nnacagncnn cgngaaanng cannn                            35

<210> SEQ ID NO 39
<211> LENGTH: 38
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(38)
<223> OTHER INFORMATION: n = 5-tyrosylcarboxyamide-dU

<400> SEQUENCE: 39
gngcngccca ncnanccncn cnnangaanc cgaanncc                         38

<210> SEQ ID NO 40
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 40
nccannccac cgcggngcca cagnancang nnngcngaan                       40

<210> SEQ ID NO 41
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 41
nccnanccnc ncnncgngaa nccgaanngc cnacngccnn                       40
```

```
<210> SEQ ID NO 42
<211> LENGTH: 41
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(41)
<223> OTHER INFORMATION: n = 5-tyrosylcarboxyamide-dU

<400> SEQUENCE: 42
ncacaaacna nccgnnccnn ggngaanncn caannncngg n                    41

<210> SEQ ID NO 43
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 43
nacnancacg cnnnnggnga anngcgaann cccggaggnn                      40

<210> SEQ ID NO 44
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 44
aggcgggncn ncanancccg caanngaang cacgcnnncc                      40

<210> SEQ ID NO 45
<211> LENGTH: 39
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(39)
<223> OTHER INFORMATION: n = 5-tyrosylcarboxyamide-dU

<400> SEQUENCE: 45
gngaccaacn angnnancnn cgngaanccg aanngccgn                       39

<210> SEQ ID NO 46
<211> LENGTH: 39
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(39)
<223> OTHER INFORMATION: n = 5-tyrosylcarboxyamide-dU

<400> SEQUENCE: 46
cacacnannc ccnaccanga nnggngaaan agcannncn                       39
```

<210> SEQ ID NO 47
<211> LENGTH: 6
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(1)
<223> OTHER INFORMATION: n = C or 5-tyrosylcarboxyamide-dU
<220> FEATURE:
<221> NAME/KEY: misc_feature
<222> LOCATION: (5)..(5)
<223> OTHER INFORMATION: n = A or 5-tyrosylcarboxyamide-dU
<220> FEATURE:
<221> NAME/KEY: misc_feature
<222> LOCATION: (6)..(6)
<223> OTHER INFORMATION: n = 5-tyrosylcarboxyamide-dU

<400> SEQUENCE: 47 ngaann                                                                  6

<210> SEQ ID NO 48
<211> LENGTH: 36
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(36)
<223> OTHER INFORMATION: n = 5-tyrosylcarboxyamide-dU

<400> SEQUENCE: 48
cnnacngaan acnngagcaa cancccgcan ngccga                                 36

<210> SEQ ID NO 49
<211> LENGTH: 38
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(38)
<223> OTHER INFORMATION: n = 5-tyrosylcarboxyamide-dU

<400> SEQUENCE: 49
gngcngccca ncnanccncn cnnangaanc cgaanncc                               38

<210> SEQ ID NO 50
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 50
nccnanccnc ncnncgngaa nccgaanngc cnacngccnn                             40

<210> SEQ ID NO 51
<211> LENGTH: 39
<212> TYPE: DNA
<213> ORGANISM: Artificial Sequence
<220> FEATURE:
<223> OTHER INFORMATION: Modifications are 5-tyrosylcarboxyamide-dU

```
<220> FEATURE:
<221> NAME/KEY: misc_feature
<222> LOCATION: (1)..(39)
<223> OTHER INFORMATION: n = 5-tyrosylcarboxyamide-dU

<400> SEQUENCE: 51
gngaccaacn angnnancnn cgngaanccg aanngccgn                                  39

<210> SEQ ID NO 52
<211> LENGTH: 39
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(39)
<223> OTHER INFORMATION: n = 5-tyrosylcarboxyamide-dU

<400> SEQUENCE: 52 aaccongnan nccacaccnn gccgaaanng annncnngn                                  39

<210> SEQ ID NO 53
<211> LENGTH: 39
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(39)
<223> OTHER INFORMATION: n = 5-tyrosylcarboxyamide-dU

<400> SEQUENCE: 53
accangnann accccnccnn gccgaaanca gannncngg                                  39

<210> SEQ ID NO 54
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 54
nacnancacg cnnnnggnga anngcgaann cccggaggnn                                 40

<210> SEQ ID NO 55
<211> LENGTH: 36
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(36)
<223> OTHER INFORMATION: n = 5-tyrosylcarboxyamide-dU

<400> SEQUENCE: 55
ncnanncccc gagncnngan anccacgann gaannn                                     36

<210> SEQ ID NO 56
<211> LENGTH: 43
<212> TYPE: DNA
<213> ORGANISM: Artificial Sequence
<220> FEATURE:
```

```
<223> OTHER INFORMATION: Modifications are 5-tyrosylcarboxyamide-dU
<220> FEATURE:
<221> NAME/KEY: misc_feature
<222> LOCATION: (1)..(43)
<223> OTHER INFORMATION: n = 5-tyrosylcarboxyamide-dU

<400> SEQUENCE: 56
nnggcacgaa gnanngacnn ngaanngcng aaacancnnn ncn                         43

<210> SEQ ID NO 57
<211> LENGTH: 41
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(41)
<223> OTHER INFORMATION: n = 5-tyrosylcarboxyamide-dU

<400> SEQUENCE: 57
ncacaaacna nccgnnccnn ggngaanncn caannncngg n                           41

<210> SEQ ID NO 58
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 58
ncnaaccggn ncgcanncac angaaannag gaggacancg                             40

<210> SEQ ID NO 59
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 59
gagcnaanng aagcnacagg acncnnggca cgacgggnna                             40

<210> SEQ ID NO 60
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 60
nggancacgn anncccacnn accnnccnga aanagcannn                             40

<210> SEQ ID NO 61
<211> LENGTH: 40
<212> TYPE: DNA
<213> ORGANISM: Artificial Sequence
```

```
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 61
ggncncancg acaaannggg aangngcgag cacnanncgn                               40

<210> SEQ ID NO 62
<211> LENGTH: 40
<212> TYPE: DNA
<213> ORGANISM: Artificial Sequence
<220> FEATURE:
<223> OTHER INFORMATION: Modifications are 5-tyrosylcarboxyamide-dU
<220> FEATURE:
<221> NAME/KEY: misc_feature
<222> LOCATION: (1)..(40)
<223> OTHER INFORMATION: n = 5-tyrosylcarboxyamide-dU

<400> SEQUENCE: 62
gggcncagna ncngcagagc cagnaggaac nagacggngn                               40

<210> SEQ ID NO 63
<211> LENGTH: 40
<212> TYPE: DNA
<213> ORGANISM: Artificial Sequence
<220> FEATURE:
<223> OTHER INFORMATION: Modifications are 5-benzylcarboxyamide-dU
<220> FEATURE:
<221> NAME/KEY: misc_feature
<222> LOCATION: (1)..(40)
<223> OTHER INFORMATION: n = 5-benzylcarboxyamide-dU

<400> SEQUENCE: 63
nnggcgccgn nngcggnang acncccnnnn cnnanggcng                               40

<210> SEQ ID NO 64
<211> LENGTH: 39
<212> TYPE: DNA
<213> ORGANISM: Artificial Sequence
<220> FEATURE:
<223> OTHER INFORMATION: Modifications are 5-benzylcarboxyamide-dU
<220> FEATURE:
<221> NAME/KEY: misc_feature
<222> LOCATION: (1)..(39)
<223> OTHER INFORMATION: n = 5-benzylcarboxyamide-dU

<400> SEQUENCE: 64
agngcnagcg acnccgcggn acnacnncnc ccnacnagn                                39

<210> SEQ ID NO 65
<211> LENGTH: 40
<212> TYPE: DNA
<213> ORGANISM: Artificial Sequence
<220> FEATURE:
<223> OTHER INFORMATION: Modifications are 5-benzylcarboxyamide-dU
<220> FEATURE:
<221> NAME/KEY: misc_feature
<222> LOCATION: (1)..(40)
<223> OTHER INFORMATION: n = 5-benzylcarboxyamide-dU

<400> SEQUENCE: 65
nanaaaganc nngccnnngn aanncncan gacanaaana                                40

<210> SEQ ID NO 66
<211> LENGTH: 10
<212> TYPE: DNA
```

```
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(1)
<223> OTHER INFORMATION: n = G or 5-naphthylmethylcarboxyamide-dU
<220> FEATURE:
<221> NAME/KEY: misc_feature
<222> LOCATION: (2)..(2)
<223> OTHER INFORMATION: n = C or G
<220> FEATURE:
<221> NAME/KEY: misc_feature
<222> LOCATION: (5)..(6)
<223> OTHER INFORMATION: n = 5-naphthylmethylcarboxyamide-dU
<220> FEATURE:
<221> NAME/KEY: misc_feature
<222> LOCATION: (9)..(9)
<223> OTHER INFORMATION: n = A or G
<220> FEATURE:
<221> NAME/KEY: misc_feature
<222> LOCATION: (10)..(10)
<223> OTHER INFORMATION: n = A or 5-naphnhylmenhylcarboxyamide-dU

<400> SEQUENCE: 66 nnganngynn                                                           10

<210> SEQ ID NO 67
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 67
nccnnngcga ancggganng gannacggnn gggcaanagn                           40

<210> SEQ ID NO 68
<211> LENGTH: 39
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(39)
<223> OTHER INFORMATION: n = 5-naphthylmethylcarboxyamide-dU

<400> SEQUENCE: 68
aggcncaang gngnancgan nggaaagcag nnaancgan                            39

<210> SEQ ID NO 69
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 69
gcgcncagnn ggnnggannn ggagnnggaa nnaggnagca                           40
```

<210> SEQ ID NO 70
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 70
ngggncncaa gnnggnnggc ccannggggan nggaagnccn                              40

<210> SEQ ID NO 71
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 71
cccngcgcng annngcaann agcacggcng ncggngaacn                               40

<210> SEQ ID NO 72
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(40)
<223> OTHER INFORMATION: n = 5-naphthylmethylcarboxyamide-dU

<400> SEQUENCE: 72
nccancggga ccacnaacgn nagcnccagg cgggacngnc                               40

<210> SEQ ID NO 73
<211> LENGTH: 39
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature
<222> LOCATION: (1)..(39)
<223> OTHER INFORMATION: n = 5-naphthylmethylcarboxyamide-dU

<400> SEQUENCE: 73
nancagaccn ccancgcgnc acnnangagn ngaacacga                                39

<210> SEQ ID NO 74
<211> LENGTH: 40
<212> TYPE: DNA
<213> ORGANISM: Artificial Sequence
<220> FEATURE:
<223> OTHER INFORMATION: Modifications are 5-naphthylmethylcarboxyamide-
      dU
<220> FEATURE:
<221> NAME/KEY: misc_feature

```
<222> LOCATION: (1)..(40)
<223> OTHER INFORMATION: n = 5-naphthylmethylcarboxyamide-dU

<400> SEQUENCE: 74
nannngnccc anncccacnn aangcnagca cacgnnaaca                              40

<210> SEQ ID NO 75
<211> LENGTH: 23
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(1)
<223> OTHER INFORMATION: n = 5-tryptaminocarboxyamide-dU
<220> FEATURE:
<221> NAME/KEY: misc_feature
<222> LOCATION: (2)..(2)
<223> OTHER INFORMATION: n = A, G, C, or 5-tryptaminocarboxyamide-dU
<220> FEATURE:
<221> NAME/KEY: misc_feature
<222> LOCATION: (4)..(4)
<223> OTHER INFORMATION: n = C or 5-tryptaminocarboxyamide-dU
<220> FEATURE:
<221> NAME/KEY: misc_feature
<222> LOCATION: (5)..(7)
<223> OTHER INFORMATION: n = A, G, C, or 5-tryptaminocarboxyamide-dU
<220> FEATURE:
<221> NAME/KEY: misc_feature
<222> LOCATION: (8)..(8)
<223> OTHER INFORMATION: n = 5-tryptaminocarboxyamide-dU
<220> FEATURE:
<221> NAME/KEY: misc_feature
<222> LOCATION: (10)..(11)
<223> OTHER INFORMATION: n = 5-tryptaminocarboxyamide-dU
<220> FEATURE:
<221> NAME/KEY: misc_feature
<222> LOCATION: (12)..(12)
<223> OTHER INFORMATION: n = A, G, C, or 5-tryptaminocarboxyamide-dU
<220> FEATURE:
<221> NAME/KEY: misc_feature
<222> LOCATION: (15)..(15)
<223> OTHER INFORMATION: n = A or G
<220> FEATURE:
<221> NAME/KEY: misc_feature
<222> LOCATION: (16)..(16)
<223> OTHER INFORMATION: n = A or 5-nrypnaminocarboxyamide-dU
<220> FEATURE:
<221> NAME/KEY: misc_feature
<222> LOCATION: (17)..(17)
<223> OTHER INFORMATION: n = 5-nrypnaminocarboxyamide-dU
<220> FEATURE:
<221> NAME/KEY: misc_feature
<222> LOCATION: (18)..(18)
<223> OTHER INFORMATION: n = A or C
<220> FEATURE:
<221> NAME/KEY: misc_feature
<222> LOCATION: (20)..(20)
<223> OTHER INFORMATION: n = A or C
<220> FEATURE:
<221> NAME/KEY: misc_feature
<222> LOCATION: (21)..(21)
<223> OTHER INFORMATION: n = C or G
<220> FEATURE:
<221> NAME/KEY: misc_feature
<222> LOCATION: (22)..(22)
<223> OTHER INFORMATION: n = C or 5-nrypnaminocarboxyamide-dU
<220> FEATURE:
<221> NAME/KEY: misc_feature
<222> LOCATION: (23)..(23)
<223> OTHER INFORMATION: n = 5-tryptaminocarboxyamide-dU

<400> SEQUENCE: 75
nncnnnnncn nnaannnnan nnn                                                23
```

<210> SEQ ID NO 76
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 76
cangncncaa ncnnaagan aacgnngacc gcgagnaccg         40

<210> SEQ ID NO 77
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 77
ngcngacaga cacangnccc cncncnnaaa ganaacgnng         40

<210> SEQ ID NO 78
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 78
ancaccccnc nnnaaganaa cgnnccggac cgcgcganaa         40

<210> SEQ ID NO 79
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 79
ncngcnangn cnnnaaganc aaccnaagag angcangana         40

<210> SEQ ID NO 80
<211> LENGTH: 41
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(41)
<223> OTHER INFORMATION: n = 5-tryptaminocarboxyamide-dU

<400> SEQUENCE: 80
gnnggagcgn ngnggcnnca ccnnacngga ncnngaaccn c         41

```
<210> SEQ ID NO 81
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 81
gncgancnnc aaannangna cganngaccn aacanggnac                                40

<210> SEQ ID NO 82
<211> LENGTH: 41
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(41)
<223> OTHER INFORMATION: n = 5-tryptaminocarboxyamide-dU

<400> SEQUENCE: 82
nggnnagcac nncanncang gaccananaa cncnagnnna a                              41

<210> SEQ ID NO 83
<211> LENGTH: 15
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (2)..(2)
<223> OTHER INFORMATION: n = 5-tryptaminocarboxyamide-dU
<220> FEATURE:
<221> NAME/KEY: misc_feature
<222> LOCATION: (3)..(3)
<223> OTHER INFORMATION: n = A, G, C, or 5-tryptaminocarboxyamide-dU
<220> FEATURE:
<221> NAME/KEY: misc_feature
<222> LOCATION: (5)..(5)
<223> OTHER INFORMATION: n = A, G, C, or 5-tryptaminocarboxyamide-dU
<220> FEATURE:
<221> NAME/KEY: misc_feature
<222> LOCATION: (7)..(7)
<223> OTHER INFORMATION: n = 5-tryptaminocarboxyamide-dU
<220> FEATURE:
<221> NAME/KEY: misc_feature
<222> LOCATION: (9)..(9)
<223> OTHER INFORMATION: n = 5-tryptaminocarboxyamide-dU
<220> FEATURE:
<221> NAME/KEY: misc_feature
<222> LOCATION: (15)..(15)
<223> OTHER INFORMATION: n = 5-tryptaminocarboxyamide-dU

<400> SEQUENCE: 83
cnngnancng gaaan                                                          15

<210> SEQ ID NO 84
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
```

<223> OTHER INFORMATION: n = 5-tryptaminocarboxyamide-dU

<400> SEQUENCE: 84
acnnnncgca cccggccnna ngccnngcan cnggaaangg                           40

<210> SEQ ID NO 85
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 85
nnnncggaag ccgcnnancc gcccacncgg ancnggaaan                           40

<210> SEQ ID NO 86
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 86
ngncgagnaa acggcgaccg nnnccccngn agnaacnaca                           40

<210> SEQ ID NO 87
<211> LENGTH: 39
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(39)
<223> OTHER INFORMATION: n = 5-tryptaminocarboxyamide-dU

<400> SEQUENCE: 87
ngnnncaacn angaanccag cnaccgngca accaangna                            39

<210> SEQ ID NO 88
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 88
agngnaanag naacccnnag acnangcccn ngggnancgg                           40

<210> SEQ ID NO 89
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 89
ngcggcngaa gaagcangca agncancggn ccgnnggnan       40

<210> SEQ ID NO 90
<211> LENGTH: 38
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (2)..(2)
<223> OTHER INFORMATION: n = A, G, C, or 5-(2-naphthylmethyl)
      carboxyamide
<220> FEATURE:
<221> NAME/KEY: misc_feature
<222> LOCATION: (4)..(4)
<223> OTHER INFORMATION: n = A, G, C, or 5-(2-naphthylmethyl)
      carboxyamide
<220> FEATURE:
<221> NAME/KEY: misc_feature
<222> LOCATION: (5)..(7)
<223> OTHER INFORMATION: n = 5-(2-naphthylmethyl)carboxyamide
<220> FEATURE:
<221> NAME/KEY: misc_feature
<222> LOCATION: (11)..(11)
<223> OTHER INFORMATION: n = 5-(2-naphthylmethyl)carboxyamide
<220> FEATURE:
<221> NAME/KEY: misc_feature
<222> LOCATION: (16)..(18)
<223> OTHER INFORMATION: n = 5-(2-naphthylmethyl)carboxyamide
<220> FEATURE:
<221> NAME/KEY: misc_feature
<222> LOCATION: (19)..(19)
<223> OTHER INFORMATION: n = A, G, C, or 5-(2-naphthylmethyl)
      carboxyamide
<220> FEATURE:
<221> NAME/KEY: misc_feature
<222> LOCATION: (21)..(29)
<223> OTHER INFORMATION: n = A, G, C, or 5-(2-naphthylmethyl)
      carboxyamide
<220> FEATURE:
<221> NAME/KEY: misc_feature
<222> LOCATION: (31)..(31)
<223> OTHER INFORMATION: n = A, G, C, or 5-(2-naphthylmethyl)
      carboxyamide
<220> FEATURE:
<221> NAME/KEY: misc_feature
<222> LOCATION: (33)..(34)
<223> OTHER INFORMATION: n = 5-(2-naphthylmethyl)carboxyamide
<220> FEATURE:
<221> NAME/KEY: misc_feature
<222> LOCATION: (35)..(35)
<223> OTHER INFORMATION: n = A, G, C, or 5-(2-naphthylmethyl)
      carboxyamide
<220> FEATURE:
<221> NAME/KEY: misc_feature
<222> LOCATION: (37)..(37)
<223> OTHER INFORMATION: n = 5-(2-naphthylmethyl)carboxyamide

<400> SEQUENCE: 90
ancnnnnaag ngaacnnnna nnnnnnnnng ngnnnana       38

<210> SEQ ID NO 91
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:

```
<221> NAME/KEY: misc_feature
<222> LOCATION: (1)..(40)
<223> OTHER INFORMATION: n = 5-(2-naphthylmethyl)carboxyamide

<400> SEQUENCE: 91
ccagcannna agngaacnnn aaggaaggga ggagnncana                  40

<210> SEQ ID NO 92
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 92
agaccgnnna agngaacnnn caacgggang cgngnnaana                  40

<210> SEQ ID NO 93
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 93
agnggcgnna angcannnaa cgagcacnga ggcgnnaana                  40

<210> SEQ ID NO 94
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 94
cnnnnnnacc gcngcangac nnnagcggca gncgngngng                  40

<210> SEQ ID NO 95
<211> LENGTH: 34
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(34)
<223> OTHER INFORMATION: n = 5-phenethyl-1-carboxyamide

<400> SEQUENCE: 95
gccnnncnng nnaaacgncc nnganggcag cgnn                        34

<210> SEQ ID NO 96
<211> LENGTH: 40
<212> TYPE: DNA
```

-continued

```
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 96
gaacgngccn nncnngnnaa acgnccnnga nggcagcgnn                              40

<210> SEQ ID NO 97
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 97
aacncggccn nncnngnnaa acgnccnnga nggcagcgnn                              40

<210> SEQ ID NO 98
<211> LENGTH: 11
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(11)
<223> OTHER INFORMATION: n = 5-phenethyl-1-carboxyamide

<400> SEQUENCE: 98
agnnngancc c                                                             11

<210> SEQ ID NO 99
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 99
nacggcannc nggnggcaag nnnganccen ccgagccnan                              40

<210> SEQ ID NO 100
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 100
cgancacanc gcacannagn cagnnnganc ccannaanca                              40

<210> SEQ ID NO 101
<211> LENGTH: 40
```

<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 101
ncaggnnana cccagngnag gaaaacgngn acgnnccgan                                40

<210> SEQ ID NO 102
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 102
aannnangng ancaanngag cagaccgcca nnngacnncg                                40

<210> SEQ ID NO 103
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 103
ggnggnggaa annggcaagn gnanggnggn nacgccgnan                                40

<210> SEQ ID NO 104
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 104
ngcgncngan ccgnaaaacc annncaagcn accangnnna                                40

<210> SEQ ID NO 105
<211> LENGTH: 39
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(39)
<223> OTHER INFORMATION: n = 5-phenethyl-1-carboxyamide

<400> SEQUENCE: 105
cgccgnnncc gnccggccac aannnaagna caannggan                                 39

<210> SEQ ID NO 106

```
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 106
ngnccgccga ccannnncng nanagccncn ngnaannagn                          40

<210> SEQ ID NO 107
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 107
gaaagcnncg nacgnagnng ngagaggncn cngcccncnn                          40

<210> SEQ ID NO 108
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 108
annaagcnng nggcnggnag cngacagcca ggganncnga                          40

<210> SEQ ID NO 109
<211> LENGTH: 40
<212> TYPE: DNA
<213> ORGANISM: Artificial Sequence
<220> FEATURE:
<223> OTHER INFORMATION: Modifications are 5-tryptaminocarboxyamide-dU
<220> FEATURE:
<221> NAME/KEY: misc_feature
<222> LOCATION: (1)..(40)
<223> OTHER INFORMATION: n = 5-tryptaminocarboxyamide-dU

<400> SEQUENCE: 109
gaagacnnna anncngacan ggngnccaan ggcgcgcgag                          40

<210> SEQ ID NO 110
<211> LENGTH: 29
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (4)..(4)
<223> OTHER INFORMATION: n = 5-(2-naphthylmethyl)carboxyamide
<220> FEATURE:
<221> NAME/KEY: misc_feature
<222> LOCATION: (6)..(6)
```

```
<223> OTHER INFORMATION: n = 5-(2-naphthylmethyl)carboxyamide
<220> FEATURE:
<221> NAME/KEY: misc_feature
<222> LOCATION: (7)..(7)
<223> OTHER INFORMATION: n = A, G, C, or 5-(2-naphthylmethyl)
      carboxyamide
<220> FEATURE:
<221> NAME/KEY: misc_feature
<222> LOCATION: (8)..(8)
<223> OTHER INFORMATION: n = 5-(2-naphthylmethyl)carboxyamide
<220> FEATURE:
<221> NAME/KEY: misc_feature
<222> LOCATION: (12)..(12)
<223> OTHER INFORMATION: n = 5-(2-naphthylmethyl)carboxyamide
<220> FEATURE:
<221> NAME/KEY: misc_feature
<222> LOCATION: (15)..(15)
<223> OTHER INFORMATION: n = A, G, C, or 5-(2-naphthylmethyl)
      carboxyamide
<220> FEATURE:
<221> NAME/KEY: misc_feature
<222> LOCATION: (17)..(17)
<223> OTHER INFORMATION: n = 5-(2-naphthylmethyl)carboxyamide
<220> FEATURE:
<221> NAME/KEY: misc_feature
<222> LOCATION: (20)..(20)
<223> OTHER INFORMATION: n = 5-(2-naphthylmethyl)carboxyamide
<220> FEATURE:
<221> NAME/KEY: misc_feature
<222> LOCATION: (22)..(23)
<223> OTHER INFORMATION: n = A, G, C, or 5-(2-naphthylmethyl)
      carboxyamide
<220> FEATURE:
<221> NAME/KEY: misc_feature
<222> LOCATION: (25)..(25)
<223> OTHER INFORMATION: n = 5-(2-naphthylmethyl)carboxyamide
<220> FEATURE:
<221> NAME/KEY: misc_feature
<222> LOCATION: (27)..(28)
<223> OTHER INFORMATION: n = 5-(2-naphthylmethyl)carboxyamide
<220> FEATURE:
<221> NAME/KEY: misc_feature
<222> LOCATION: (29)..(29)
<223> OTHER INFORMATION: n = C or G

<400> SEQUENCE: 110
gaanannncc gngangnaan gnnanannn                                        29

<210> SEQ ID NO 111
<211> LENGTH: 28
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(28)
<223> OTHER INFORMATION: n = 5-(2-naphthylmethyl)carboxyamide

<400> SEQUENCE: 111
gaancngncc gngacgnaan gaanannc                                         28

<210> SEQ ID NO 112
<211> LENGTH: 38
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(38)
<223> OTHER INFORMATION: n = 5-(2-naphthylmethyl)carboxyamide
```

<400> SEQUENCE: 112
gaancngncc gngacgnaan gccananncg gaggggan                                    38

<210> SEQ ID NO 113
<211> LENGTH: 34
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(34)
<223> OTHER INFORMATION: n = 5-(2-naphthylmethyl)carboxyamide

<400> SEQUENCE: 113
gaancngncc gngaagnaan gccananncg cang                                        34

<210> SEQ ID NO 114
<211> LENGTH: 29
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(29)
<223> OTHER INFORMATION: n = 5-(2-naphthylmethyl)carboxyamide

<400> SEQUENCE: 114
gaanangncc gngaagnaan gcganannc                                              29

<210> SEQ ID NO 115
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 115
gaanangncc gngaagnaan ggcananncg nccacgnggg                                  40

<210> SEQ ID NO 116
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 116
cgggncaccg canncnccgn gacgnaanga cananncggn                                  40

<210> SEQ ID NO 117
<211> LENGTH: 40
<212> TYPE: DNA
<213> ORGANISM: Artificial Sequence
<220> FEATURE:
<223> OTHER INFORMATION: Modifications are 5-(2-naphthylmethyl)

```
                                 carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 117
aaccccgcgg caannanccg ngaagnaang aananccga                              40

<210> SEQ ID NO 118
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 118
acagaggcan ncnccgngan gnaangcaan annccgccgn                             40

<210> SEQ ID NO 119
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 119
ngcaacnanc cgngangnaa ngcaananng caacangngc                             40

<210> SEQ ID NO 120
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 120
ggacnacncn ccgngangna angcgaaann cccagangna                             40

<210> SEQ ID NO 121
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 121
ncgaangana acangnaacn ccgngannac ancgaanagn                             40
```

```
<210> SEQ ID NO 122
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 122
cnaagcnccg aggcnnacnc cgngancgca nggnnnaacc                              40

<210> SEQ ID NO 123
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 123
ncgagcaacg agnaacnccg ngannacaan cganaganga                              40

<210> SEQ ID NO 124
<211> LENGTH: 15
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (2)..(3)
<223> OTHER INFORMATION: n = 5-(2-naphthylmethyl)carboxyamide
<220> FEATURE:
<221> NAME/KEY: misc_feature
<222> LOCATION: (4)..(4)
<223> OTHER INFORMATION: n = A or G
<220> FEATURE:
<221> NAME/KEY: misc_feature
<222> LOCATION: (7)..(7)
<223> OTHER INFORMATION: n = 5-(2-naphthylmethyl)carboxyamide
<220> FEATURE:
<221> NAME/KEY: misc_feature
<222> LOCATION: (8)..(8)
<223> OTHER INFORMATION: n = A, G, C, or 5-(2-naphthylmethyl)
      carboxyamide
<220> FEATURE:
<221> NAME/KEY: misc_feature
<222> LOCATION: (11)..(11)
<223> OTHER INFORMATION: n = 5-(2-naphthylmethyl)carboxyamide
<220> FEATURE:
<221> NAME/KEY: misc_feature
<222> LOCATION: (15)..(15)
<223> OTHER INFORMATION: n = C or G

<400> SEQUENCE: 124
annngcnncc nggcn                                                        15

<210> SEQ ID NO 125
<211> LENGTH: 9
<212> TYPE: DNA
<213> ORGANISM: Artificial Sequence
<220> FEATURE:
<223> OTHER INFORMATION: Modifications are 5-(2-naphthylmethyl)
      carboxyamide
```

```
<220> FEATURE:
<221> NAME/KEY: misc_feature
<222> LOCATION: (1)..(1)
<223> OTHER INFORMATION: n = A or 5-(2-naphthylmethyl)carboxyamide
<220> FEATURE:
<221> NAME/KEY: misc_feature
<222> LOCATION: (3)..(3)
<223> OTHER INFORMATION: n = A or 5-(2-naphthylmethyl)carboxyamide
<220> FEATURE:
<221> NAME/KEY: misc_feature
<222> LOCATION: (4)..(5)
<223> OTHER INFORMATION: n = 5-(2-naphthylmethyl)carboxyamide
<220> FEATURE:
<221> NAME/KEY: misc_feature
<222> LOCATION: (7)..(8)
<223> OTHER INFORMATION: n = 5-(2-naphthylmethyl)carboxyamide

<400> SEQUENCE: 125 nannnanna                                                                9

<210> SEQ ID NO 126
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 126
nngcnaccca annagcnccn ggcgggnnaa nnannagaca                              40

<210> SEQ ID NO 127
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 127
canccaanna gcnccnggc gangnaanna nnanggcacn                               40

<210> SEQ ID NO 128
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 128
ncgnanaccg aannagcngc cnggcgaccn aannannaca                              40

<210> SEQ ID NO 129
<211> LENGTH: 40
<212> TYPE: DNA
<213> ORGANISM: Artificial Sequence
<220> FEATURE:
<223> OTHER INFORMATION: Modifications are 5-(2-naphthylmethyl)
```

```
               carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 129
ccngccncan nagcnccngg cgcccnnaan nannaaaacn                              40

<210> SEQ ID NO 130
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 130
gaccncanca nnggcnccng gccggnnaan nannaccacc                              40

<210> SEQ ID NO 131
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 131
nagagaaann ggcngcgngg ccacccnaan nannagagca                              40

<210> SEQ ID NO 132
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 132
cncaaggcna nnggcngcng gcagannaan nannaaagnc                              40

<210> SEQ ID NO 133
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 133
annggcnccn ggccgganaa nnnannaccc agngagngaa                              40
```

```
<210> SEQ ID NO 134
<211> LENGTH: 15
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (4)..(5)
<223> OTHER INFORMATION: n = 5-(2-naphthylmethyl)carboxyamide
<220> FEATURE:
<221> NAME/KEY: misc_feature
<222> LOCATION: (11)..(12)
<223> OTHER INFORMATION: n = 5-(2-naphthylmethyl)carboxyamide
<220> FEATURE:
<221> NAME/KEY: misc_feature
<222> LOCATION: (14)..(14)
<223> OTHER INFORMATION: n = A or C

<400> SEQUENCE: 134
gganngcagg nncnc                                              15

<210> SEQ ID NO 135
<211> LENGTH: 39
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(39)
<223> OTHER INFORMATION: n = 5-(2-naphthylmethyl)carboxyamide

<400> SEQUENCE: 135
nagncacggn gaacnggann gcaggnnccc cccnggcna                    39

<210> SEQ ID NO 136
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 136
ggncagcngg anngcaggnn cccccngan aggacggnnn                    40

<210> SEQ ID NO 137
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 137
gnagncggan ngcaggnncc caccaaacac cnnnggnaga                   40

<210> SEQ ID NO 138
<211> LENGTH: 40
<212> TYPE: DNA
```

```
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 138
cnggagacng gncagaacag ccgggganngc aggnncacgg                            40

<210> SEQ ID NO 139
<211> LENGTH: 11
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(11)
<223> OTHER INFORMATION: n = 5-(2-naphthylmethyl)carboxyamide

<400> SEQUENCE: 139
gaanngnncc g                                                           11

<210> SEQ ID NO 140
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 140
gnngaanngn nccgccgccn nncngnccgc gggnngcngn                             40

<210> SEQ ID NO 141
<211> LENGTH: 38
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(38)
<223> OTHER INFORMATION: n = 5-(2-naphthylmethyl)carboxyamide

<400> SEQUENCE: 141
ngncagaann gnnccganag ggnngcngcc acnganan                               38

<210> SEQ ID NO 142
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 142
```
gccnnnnggc gaggngagnn nncccagncn gangaagcnn                40

<210> SEQ ID NO 143
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 143
cggagcccga aggnnaagcg gnncaccann anacganacg                40

<210> SEQ ID NO 144
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 144
cnccgnanng cgnccngggc agnnaancna nnagaagcca                40

<210> SEQ ID NO 145
<211> LENGTH: 9
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(1)
<223> OTHER INFORMATION: n = 5-phenethyl-1-carboxyamide
<220> FEATURE:
<221> NAME/KEY: misc_feature
<222> LOCATION: (5)..(5)
<223> OTHER INFORMATION: n = A or 5-phenethyl-1-carboxyamide
<220> FEATURE:
<221> NAME/KEY: misc_feature
<222> LOCATION: (7)..(9)
<223> OTHER INFORMATION: n = 5-phenethyl-1-carboxyamide

<400> SEQUENCE: 145 naaangnnn                                                   9

<210> SEQ ID NO 146
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 146
gngngncagc gcannanacg cgnaannaaa ngnnnagaga                40

<210> SEQ ID NO 147
<211> LENGTH: 40

-continued

```
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 147
gcgngncngn annaaaagnn ngcggagggg nncccggnac                          40

<210> SEQ ID NO 148
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 148
nnncgagaan aaangnnnga nacannacnn anaananggn                          40

<210> SEQ ID NO 149
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 149
agccggngng ngnannaacn cnnncggcnn nccnccccgca                         40

<210> SEQ ID NO 150
<211> LENGTH: 40
<212> TYPE: DNA
<213> ORGANISM: Artificial Sequence
<220> FEATURE:
<223> OTHER INFORMATION: Modifications are 5-phenethyl-1-carboxyamide
<220> FEATURE:
<221> NAME/KEY: misc_feature
<222> LOCATION: (1)..(40)
<223> OTHER INFORMATION: n = 5-phenethyl-1-carboxyamide

<400> SEQUENCE: 150
cnngngnaaa ccgngcgnna gnannggaga nagcngacan                          40

<210> SEQ ID NO 151
<211> LENGTH: 8
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(2)
<223> OTHER INFORMATION: n = 5-(2-naphthylmethyl)carboxyamide
<220> FEATURE:
<221> NAME/KEY: misc_feature
<222> LOCATION: (4)..(4)
<223> OTHER INFORMATION: n = A or G
<220> FEATURE:
<221> NAME/KEY: misc_feature
```

```
<222> LOCATION: (6)..(6)
<223> OTHER INFORMATION: n = C or G
<220> FEATURE:
<221> NAME/KEY: misc_feature
<222> LOCATION: (8)..(8)
<223> OTHER INFORMATION: n = C or G

<400> SEQUENCE: 151 nnanancn                                                                  8

<210> SEQ ID NO 152
<211> LENGTH: 12
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(12)
<223> OTHER INFORMATION: n = 5-(2-naphthylmethyl)carboxyamide

<400> SEQUENCE: 152
nnnggcnnna cg                                                            12

<210> SEQ ID NO 153
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 153
aagnnaaacc gagacgcggc cggaagccnn nggcnnnacg                               40

<210> SEQ ID NO 154
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 154
gnnaaacccc ggggggggcca agcgcannng gcnnnacgaa                              40

<210> SEQ ID NO 155
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 155
caacgnnaan nagagccnnn gnccnaacaa annacgcang                               40
```

```
<210> SEQ ID NO 156
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 156
aancggagcc cnnanaaccc nnaaacccnn nanaccaann                              40

<210> SEQ ID NO 157
<211> LENGTH: 12
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (5)..(7)
<223> OTHER INFORMATION: n = 5-(2-naphthylmethyl)carboxyamide
<220> FEATURE:
<221> NAME/KEY: misc_feature
<222> LOCATION: (9)..(9)
<223> OTHER INFORMATION: n = A or G
<220> FEATURE:
<221> NAME/KEY: misc_feature
<222> LOCATION: (11)..(12)
<223> OTHER INFORMATION: n = 5-(2-naphthylmethyl)carboxyamide

<400> SEQUENCE: 157
agccnnngnc nn                                                           12

<210> SEQ ID NO 158
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 158
aagnnaaacc gagacgcggc cggaagccnn nggcnnnacg                              40

<210> SEQ ID NO 159
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 159
gnnaannaga gccnnngacn ngaacaggnn cacgcannac                              40

<210> SEQ ID NO 160
<211> LENGTH: 40
```

```
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 160
cnngacngna ccnnnnncga cacagaacag caagaccnnc                              40

<210> SEQ ID NO 161
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 161
ggaccganga ancnagcnng nnaanagcgn ngagcnancc                              40

<210> SEQ ID NO 162
<211> LENGTH: 40
<212> TYPE: DNA
<213> ORGANISM: Artificial Sequence
<220> FEATURE:
<223> OTHER INFORMATION: Modifications are 5-(2-naphthylmethyl)
      carboxyamide
<220> FEATURE:
<221> NAME/KEY: misc_feature
<222> LOCATION: (1)..(40)
<223> OTHER INFORMATION: n = 5-(2-naphthylmethyl)carboxyamide

<400> SEQUENCE: 162
cacnnagcaa ccgacacaag nngnnccgnn anccgnnana                              40

<210> SEQ ID NO 163
<211> LENGTH: 39
<212> TYPE: DNA
<213> ORGANISM: Artificial Sequence
<220> FEATURE:
<223> OTHER INFORMATION: primer for tcdA

<400> SEQUENCE: 163
gcgcaagctt cttcaaaatg gatatattac tattgaaag                               39

<210> SEQ ID NO 164
<211> LENGTH: 32
<212> TYPE: DNA
<213> ORGANISM: Artificial Sequence
<220> FEATURE:
<223> OTHER INFORMATION: primer for tcdA

<400> SEQUENCE: 164
gcgcgagctc catatatccc aggggcttttt ac                                     32

<210> SEQ ID NO 165
<211> LENGTH: 38
<212> TYPE: DNA
<213> ORGANISM: Artificial Sequence
<220> FEATURE:
<223> OTHER INFORMATION: primer for tcdB
```

<400> SEQUENCE: 165
gcgcaagctt atgagtttag ttaatagaaa acagttag        38

<210> SEQ ID NO 166
<211> LENGTH: 32
<212> TYPE: DNA
<213> ORGANISM: Artificial Sequence
<220> FEATURE:
<223> OTHER INFORMATION: primer for tcdB

<400> SEQUENCE: 166
gcgcgagctc catcttcacc aagagaacct tc        32

<210> SEQ ID NO 167
<211> LENGTH: 32
<212> TYPE: DNA
<213> ORGANISM: Artificial Sequence
<220> FEATURE:
<223> OTHER INFORMATION: primer for cdtA

<400> SEQUENCE: 167
gcgcaagctt caagacttac aaagctatag tg        32

<210> SEQ ID NO 168
<211> LENGTH: 32
<212> TYPE: DNA
<213> ORGANISM: Artificial Sequence
<220> FEATURE:
<223> OTHER INFORMATION: primer for cdtA

<400> SEQUENCE: 168
gcgcgagctc caggtatcaa tgttgcatca ac        32

<210> SEQ ID NO 169
<211> LENGTH: 29
<212> TYPE: DNA
<213> ORGANISM: Artificial Sequence
<220> FEATURE:
<223> OTHER INFORMATION: primer for cdtB

<400> SEQUENCE: 169
gcgcaagctt caaactagta caagtaatc        29

<210> SEQ ID NO 170
<211> LENGTH: 33
<212> TYPE: DNA
<213> ORGANISM: Artificial Sequence
<220> FEATURE:
<223> OTHER INFORMATION: primer for cdtB

<400> SEQUENCE: 170
gcgcgagctc ggtcaaagaa attgttattt ggg        33

APTAMERS FOR *CLOSTRIDIUM DIFFICILE* DIAGNOSTICS

CROSS-REFERENCE TO RELATED APPLICATIONS

This application claims priority under 35 U.S.C. §119(e) to U.S. Provisional Application Ser. No. 61/451,227, which was filed on Mar. 10, 2011, the disclosure of which is incorporated herein in its entirety.

FIELD OF THE INVENTION

The present disclosure relates generally to the field of nucleic acids and more particularly to aptamers capable of binding to toxins produced by *C. difficile* and useful for diagnostic tests for *C. difficile*. The disclosure further relates to materials and methods for diagnosing *C. difficile* contamination or infection.

Incorporated by reference herein in its entirety is the Sequence Listing entitled "20120221SequenceListing005741_ST25.txt", created Mar. 9, 2012, size of 9 kilobytes.

BACKGROUND

The following description provides a summary of information relevant to the present disclosure and is not an admission that any of the information provided or publications referenced herein is prior art to the present disclosure.

*C. difficile* infection (CDI) has been on the rise worldwide over the last several years. The clinical and economic consequences are substantial, with more than half a million cases and estimated costs of 3.2 billion dollars per year for CDI management in the U.S. alone (O'Brien, J. A., et al., Infect. Control Hosp. Epidemiol., 2007. 28(11): p. 1219-27).

CDI is an inflammatory condition of the large bowel characterized by diarrhea and can range in severity from mild to fulminant. More severe CDI syndromes are pseudomembranous colitis and toxic megacolon. Most CDI cases occur in elderly patients in a hospital setting or in nursing homes. Hospitalization, however, increases the risk of colonization also for healthy adults. In the U.S., CDI hospitalizations and CDI-related case-fatality rates doubled between 2000 and 2005. A number of recent outbreaks have been reported in which CDI cases were primarily clonal in nature. A strain type classified as BI/NAP1/027 was responsible for more than half of the cases, and hallmarks of this epidemic "outbreak" strain are high morbidity and mortality, higher resistance to antibiotics (e.g. fluoroquinolones), the presence of a tcdC variant gene, and toxin hyper-production (Freeman, J., et al., Clin. Microbiol. Rev., 2010. 23(3): p. 529-49; Rupnik, M., M. H. Wilcox, and D. N. Gerding, Nat. Rev. Microbiol., 2009. 7(7): p. 526-36).

Use of antibiotics is a strong predisposing factor for CDI due to the disruption of the normal gut flora that otherwise suppresses *C. difficile*. Ingestion of spores is the main route of colonization of the human gut by *C. difficile*. Spores are extremely resistant to disinfectants and can persist in the environment for more than 12 months with little loss of viability or pathogenicity. Spores are also implicated in the 20-25% of CDI cases which relapse after treatment. Current treatment regimens for CDI are vancomycin or metronidazole. Several new, more selective agents that hold promise to reduce CDI recurrence rates are in clinical development.

The inflammation of the intestinal lining is caused by two toxins (toxin A and toxin B) that are expressed by some *C. difficile* strains. Toxin A and toxin B are glucosyltransferases that target small host GTPases in the Ras superfamily. They are encoded on the 19.6 kb pathogenicity locus and strains lacking these toxin genes are non-pathogenic. Toxinogenic strains can be further classified into toxinotypes according to sequence variability within the pathogenicity locus. Both toxins contribute to CDI, as shown by using isogenic mutants that produced either toxin A or toxin B alone and were cytotoxic in vitro and virulent in vivo (Kuehne, S. A., et al., Nature, 2010. 467(7316): p. 711-3). A vaccine prototype based on inactivated toxins A and B (toxoids) and anti-toxin monoclonal antibodies are being studied for their effectiveness in preventing recurrent CDI.

Toxin A and toxin B are structurally related, large toxins of MW~300 kDa, and consist of an amino-terminal catalytic domain (glucosyltransferase), a central peptidase C80 domain, a translocation domain, and multiple carboxy-terminal β-hairpin repeats. The mechanism of action of the clostridial toxins has been shown to involve binding of these β-hairpin repeats to carbohydrates present on the surface of gastrointestinal cells, endopeptidase-mediated cleavage, and internalization of the catalytic domain (Pfeifer, G., et al., J. Biol. Chem., 2003. 278(45): p. 44535-41).

Some *C. difficile* strains produce a binary toxin which possesses ADP-ribosyltransferase activity. Although its role in pathogenesis is unclear, the presence of binary toxin is a good marker for the epidemic outbreak strain BI/NAP1/027. The binary toxin consists of two subunits, which are the actin ADP-ribosyltransferase binary toxin A chain and the pore-forming binary toxin B chain. They are secreted from the bacterial cells as separate polypeptides and have the potential to combine to form a potent cytotoxin which has been shown to kill Vero cells (Sundriyal, A., et al., Protein Expr. Purif., 2010. 74(1): p. 42-8).

Rapid and accurate CDI diagnosis is important for patient care, infection control and surveillance. The *C. difficile* toxins A and B are of high clinical diagnostic relevance since they are sufficiently pathogen-specific targets and the demonstration of their presence is important for CDI diagnosis. All currently used CDI diagnostic tests are qualitative and belong to one of three types, (i) cytotoxin assay (tissue culture), (ii) non-molecular toxin tests (EIA), and (iii) molecular tests (PCR).

The tissue culture-based cytotoxin assay is considered the gold standard, but is cumbersome and not routinely performed by most clinical laboratories. In essence, this assay detects *C. difficile* toxin via the toxin's cytopathic effect in cell culture that can be neutralized with specific anti-sera. The cytotoxicity assay detects as little as 10 pg of toxin B and is the recommended confirmatory test for 510(k) submissions in the "Draft Guidance for Industry and Food and Drug Administration Staff Establishing the Performance Characteristics of In Vitro Diagnostic Devices for the Detection of *Clostridium difficile*" that was released in November 2010 FDA, http://www.fda.gov/MedicalDevices/DeviceRegulationandGuidance/GuidanceDocuments/ucm234868.htm.2010.

Molecular tests for CDI are available from several diagnostic companies. The Cepheid GeneXpert™ test is based on multiplex PCR (tcdB, cdt, tcdC), with advertised sensitivity and specificity of >95% and time-to-result of 30 min. The Meridian Illumigene™ *C. difficile* test detects the presence of the toxin producing region by isothermal loop amplification and advertised to provide results in under an hour. The BD GeneOhm™ *C diff* assay is a real-time PCR method for the detection of toxin B gene (tcdB) direct from stool samples, with an assay protocol time of less than two hours, sensitivity of 93.8% and specificity of 95.5%. Gen-Probe offers the Prodesse ProGastro Cd test which also detects the toxin B gene (tcdB) by PCR and is advertised to provide results in three hours with a sensitivity of 91.7% and specificity of 94.7%.

Non-molecular tests for *C. difficile* toxin detection in stool samples from patients with suspected CDI are also available. Enzyme immunoassays (EIAs) are the most widely used rapid detection methods for *C. difficile* common antigen and toxin A/B antigens, but traditional EIAs have modest sensitivity and specificity. Among the well-type EIAs, the Meridian Premier™ Toxins A/B test and the Techlab TOX A/B II™ test are considered the best-performing ELISAs and detect both toxins in stool specimens in less than 1 hour. These assays had about 80% sensitivity and 98% specificity when tested independently. The toxin B antibodies for the Premier™ Toxins A/B (Meridian) and for the *C. difficile* TOX A/B II™ (TechLab) were able to detect 125 pg and 250 pg of toxin B, respectively, when tested side by side (Novak-Weekley, S. M. and M. H. Hollingsworth. Clin Vaccine Immunol, 2008. 15(3): p. 575-8). Many other well-type EIAs assays have been brought to market (GA's *C. difficile* antigen, R-Biopharm's Ridascreen™ Toxin A/B; Remel's ProSpect™ Toxin A/B) but are used less often in the U.S. Membrane EIA assays performed with lateral flow devices are the Meridian ImmunoCard™ Toxins A&B, the Techlab Tox A/B Quik Chek™, and the Remel Xpect™ assays.

There is one automated test on the market, bioMérieux's VIDAS™ *C. difficile* Toxin A&B, which combines toxin testing and culture based identification with the API® 20A strip and automated bacterial genotyping with the DiversiLab® system.

Aptamer-based *C. difficile* toxin tests, like EIAs, have the advantage over molecular tests that they do not require big investments in equipment or expensive reagents. Aptamers have several distinct advantages over antibodies that are currently used in non-molecular assays, such as EIAs: aptamers generally have lower molecular weight, provide higher multiplexing capabilities (low cross-reactivity, universally-applicable assay conditions), chemical stability (to heat, drying, and solvents, reversible renaturation), provide ease of reagent manufacturing, consistent lot-to-lot performance and can be produced at lower cost.

Aptamers can be generated against virtually any protein target, not only toxins A/B, but also binary toxin for which there is no antibody-based test of which Applicants are aware. Detection and read-out methods can be the same as for existing tests, thus minimizing equipment needs and training requirements.

SUMMARY

The present disclosure provides various aptamers that bind to toxins produced by *C. difficile*. Included are diagnostic kits and diagnostic methods comprising such aptamers; and methods of making and using such aptamers.

The provided aptamers bind to *C. difficile* toxin A, toxin B, binary toxin A chain, or binary toxin B chain. Diagnostic methods are provided for detecting a *C. difficile* toxin which comprise an aptamer to a toxin produced by *C. difficile* including but are not limited to pull-down assays, dot blot assays, PCR assays and sandwich assays.

The provided aptamers optionally comprise at least one pyrimidine modified at a C-5 position and may comprise at least one addition chemical modification. Also provided are aptamers and methods for identifying or producing such aptamers which bind to a *C. difficile* toxin which have a slow off-rate from the toxin. Further provided are aptamers and methods for identifying or producing such aptamers which bind to a *C. difficile* toxin which have nuclease resistance.

BRIEF DESCRIPTION OF THE DRAWINGS

Figure 1B:
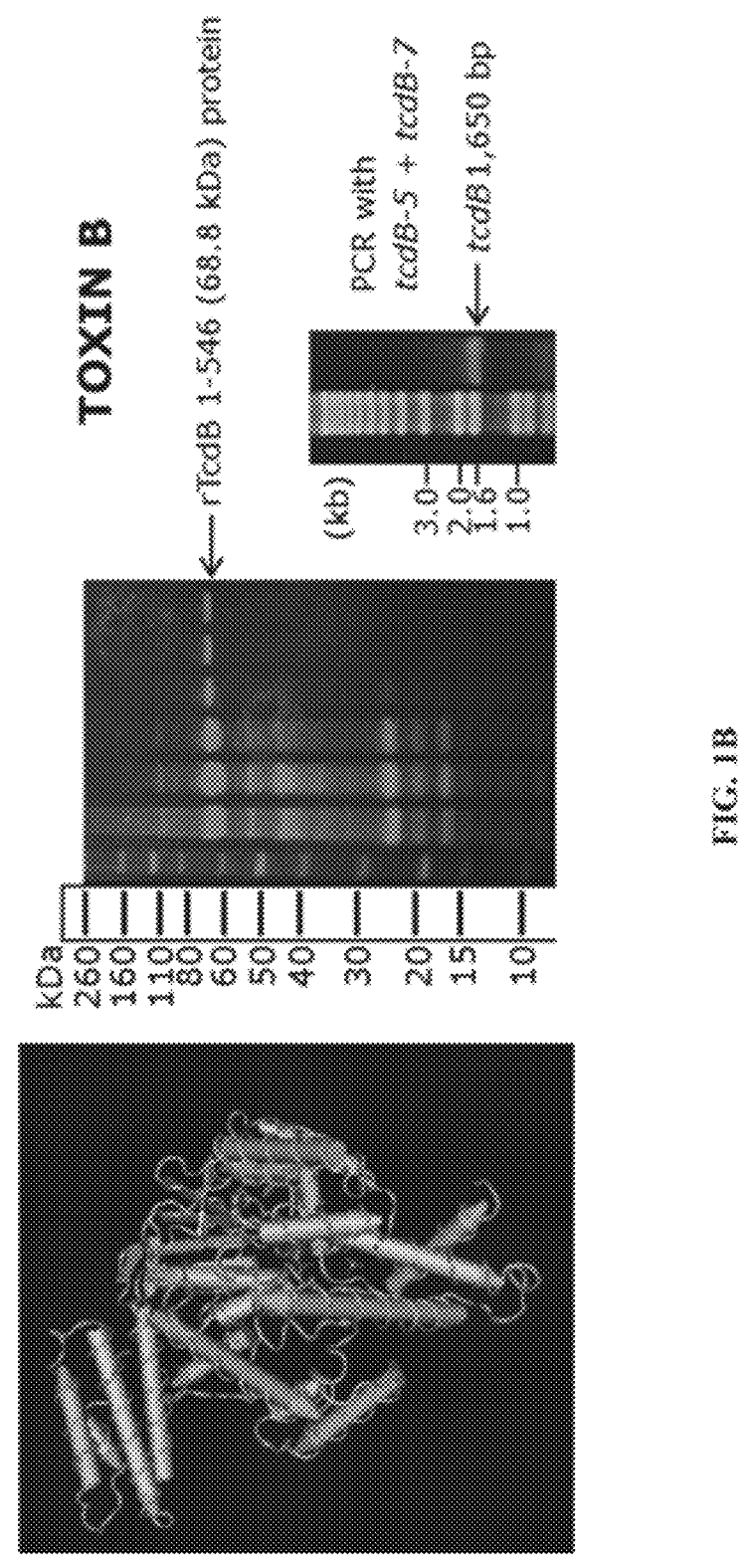

FIG. 1A illustrates the crystal structure of *C. difficile* toxin A (rTcdA) including five carboxy-terminal receptor-binding repeats (Ho, J. G., et al. Proc. Natl. Acad. Sci. USA, 2005. 102(51): p. 18373-8); shows the purification of toxin A as a recombinant tagged protein purified via affinity chromatography with Ni-NTA agarose and Strep•Tactin resin using the His-tag and Strep tag of toxin A; and PCR amplification of corresponding portion of the toxin gene encoding toxin A (tcdA). FIG. 1B illustrates the crystal structure of *C. difficile* toxin B (rTcdB) amino-terminal catalytic domain (Reinert, D. J. et al. (2005), J. Mol. Biol. 351: 973-981); shows the purification of toxin B as a recombinant tagged protein purified via affinity chromatography with Ni-NTA agarose and Strep•Tactin resin using the His-tag and Strep tag of toxin B; and PCR amplification of corresponding portion of the toxin gene encoding toxin B (tcdB). FIG. 1C illustrates the crystal structure of the full-length *C. difficile* binary toxin A chain (rCdtA) (Sundriyal, A., et al., J. Biol. Chem. 2009. 284(42): p. 28713-9); shows the purification of binary toxin A chain as a recombinant tagged protein purified via affinity chromatography with Ni-NTA agarose and Strep•Tactin resin using the His-tag and Strep tag of the binary toxin A chain; and PCR amplification of corresponding portion of the toxin gene encoding the binary toxin A chain (cdtA).

FIG. 2C illustrates the results of a pull-down assay of binary toxin with aptamers to binary toxin A chain showing specificity for binary toxin A chain over binary toxin B chain and control protein BSA. FIG. 2D illustrates the results of a pull-down assay of recombinant and native toxin A as well as recombinant and native toxin B with random aptamers showing no proteins present in the pull-down fraction.

FIG. 3A illustrates detection of *C. difficile* toxin A on dot blots using biotinylated aptamers to toxin A and streptavidin-alkaline phosphatase conjugate. FIG. 3B illustrates detection of *C. difficile* toxin B on dot blots using biotinylated aptamers to toxin B and streptavidin-alkaline phosphatase conjugate.

FIG. 4A illustrates quantitative detection of toxin A by qPCR of aptamers eluted from a sample containing aptamers in complex with toxin A wherein unbound aptamers have been removed before quantitative measurement of aptamers as proxy measurement for toxin A. FIG. 4B illustrates quantitative detection of toxin B by qPCR of aptamers eluted from a sample containing aptamers in complex with toxin B wherein unbound aptamers have been removed before quantitative measurement of aptamers as proxy measurement for toxin B.

DETAILED DESCRIPTION

Figure 1D:
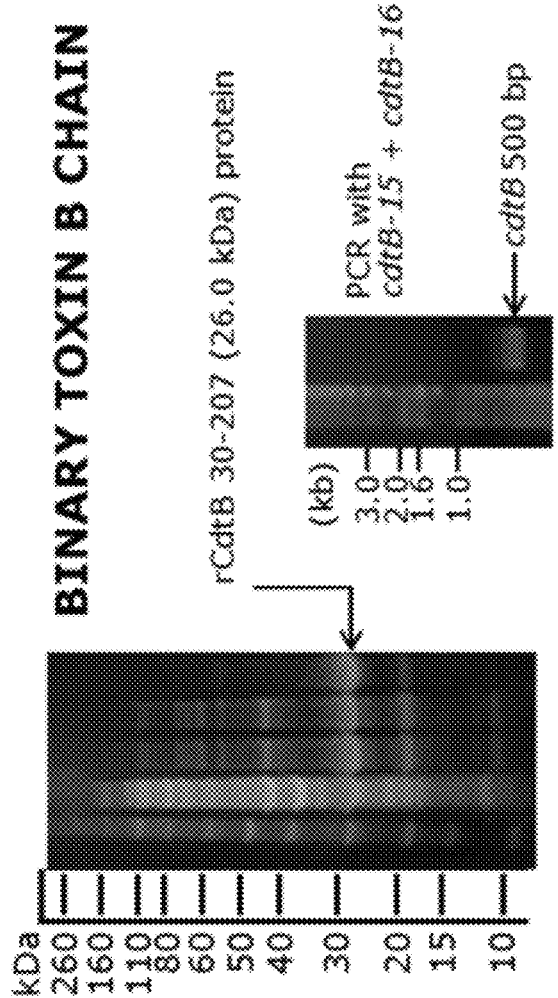
FIG. 1D illustrates the modeled structure of the full-length *C. difficile* binary toxin B chain (rCdtB); shows the purification of binary toxin B chain as a recombinant tagged protein purified via affinity chromatography with Ni-NTA agarose and Strep•Tactin resin using the His-tag and Strep tag of the binary toxin B chain; and PCR amplification of corresponding portion of the toxin gene encoding the binary toxin B chain (cdtB).
Figure 1D:
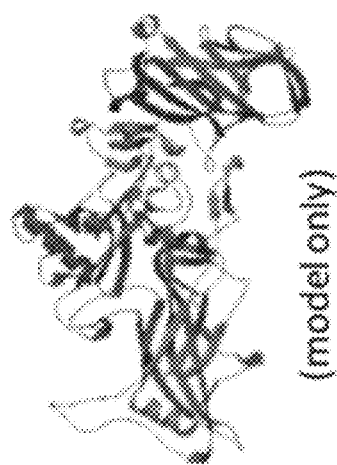

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Unless defined otherwise, technical and scientific terms used herein have the same meaning as commonly understood by one of ordinary skill in the art(s) to which this invention belongs. Although any methods, devices, and materials similar or equivalent to those described herein can be used in the practice or testing of the invention, the preferred methods, devices and materials are now described.

All publications, published patent documents, and patent applications cited in this disclosure are indicative of the level of skill in the art(s) to which the disclosure pertains. All publications, published patent documents, and patent applications cited herein are hereby incorporated by reference to the same extent as though each individual publication, published patent document, or patent application was specifically and individually indicated as being incorporated by reference.

As used in this disclosure, including the appended claims, the singular forms "a," "an," and "the" include plural references, unless the content clearly dictates otherwise, and are used interchangeably with "at least one" and "one or more." Thus, reference to "an aptamer" includes mixtures of aptamers, and the like.

As used herein, the term "about" represents an insignificant modification or variation of the numerical value such that the basic function of the item to which the numerical value relates is unchanged.

As used herein, the term "aptamer clone" refers to an aptamer of a particular nucleotide sequence. Aptamer clones are identified herein by "Aptamer ID No." as well as by "SEQ ID NO:."

As used herein, "competitor molecule" and "competitor" are used interchangeably to refer to any molecule that can form a non-specific complex with a non-target molecule. A "competitor molecule" or "competitor" is a set of copies of one type or species of molecule. "Competitor molecules" or "competitors" refer to more than one such set of molecules. Competitor molecules include oligonucleotides, polyanions (e.g., heparin, single-stranded salmon sperm DNA, and polydextrans (e.g., dextran sulphate)), abasic phosphodiester polymers, dNTPs, and pyrophosphate. In the case of a kinetic challenge that uses a competitor, the competitor can also be any molecule that can form a non-specific complex with an aptamer. Such competitor molecules include polycations (e.g., spermine, spermidine, polylysine, and polyarginine) and amino acids (e.g., arginine and lysine).

As used in tables 4, 6, 8 and 10, the term "count" refers to the number of occurrences of a particular aptamer sequence among all aptamers that were cloned and sequenced from a pool that resulted from SELEX.

As used herein, the term "dot blot" refers to an assay wherein a mixture containing the target molecule to be detected is applied directly onto a substrate as a dot followed by detection of the presence of the target molecule by an affinity molecule, wherein the affinity molecule may be, but is not limited to, an aptamer or antibody.

The term "each" when used herein to refer to a plurality of items is intended to refer to at least two of the items. It need not require that all of the items forming the plurality satisfy an associated additional limitation.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, "consensus sequence," when used in reference to a series of related nucleic acids, refers to a nucleotide sequence that reflects the most common choice of base at each position in the sequence where the series of related nucleic acids has been subjected to mathematical and/or sequence analysis.

As used herein, the term "nucleotide" refers to a ribonucleotide or a deoxyribonucleotide, or a modified form thereof, as well as an analog thereof. Nucleotides include species that include purines (e.g., adenine, hypoxanthine, guanine, and their derivatives and analogs) as well as pyrimidines (e.g., cytosine, uracil, thymine, and their derivatives and analogs).

As used herein, "nucleic acid," "oligonucleotide," and "polynucleotide" are used interchangeably to refer to a polymer of nucleotides and include DNA, RNA, DNA/RNA hybrids and modifications of these kinds of nucleic acids, oligonucleotides and polynucleotides, wherein the attachment of various entities or moieties to the nucleotide units at any position are included. The terms "polynucleotide," "oligonucleotide," and "nucleic acid" include double- or single-stranded molecules as well as triple-helical molecules. Nucleic acid, oligonucleotide, and polynucleotide are broader terms than the term aptamer and, thus, the terms nucleic acid, oligonucleotide, and polynucleotide include polymers of nucleotides that are aptamers but the terms nucleic acid, oligonucleotide, and polynucleotide are not limited to aptamers.

As used herein, the terms "modify", "modified", "modification", and any variations thereof, when used in reference to an oligonucleotide, means that at least one of the four constituent nucleotide bases (i.e., A, G, T/U, and C) of the oligonucleotide is an analog or ester of a naturally occurring nucleotide. In some embodiments, the modified nucleotide confers nuclease resistance to the oligonucleotide. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R', P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

Figure 9:
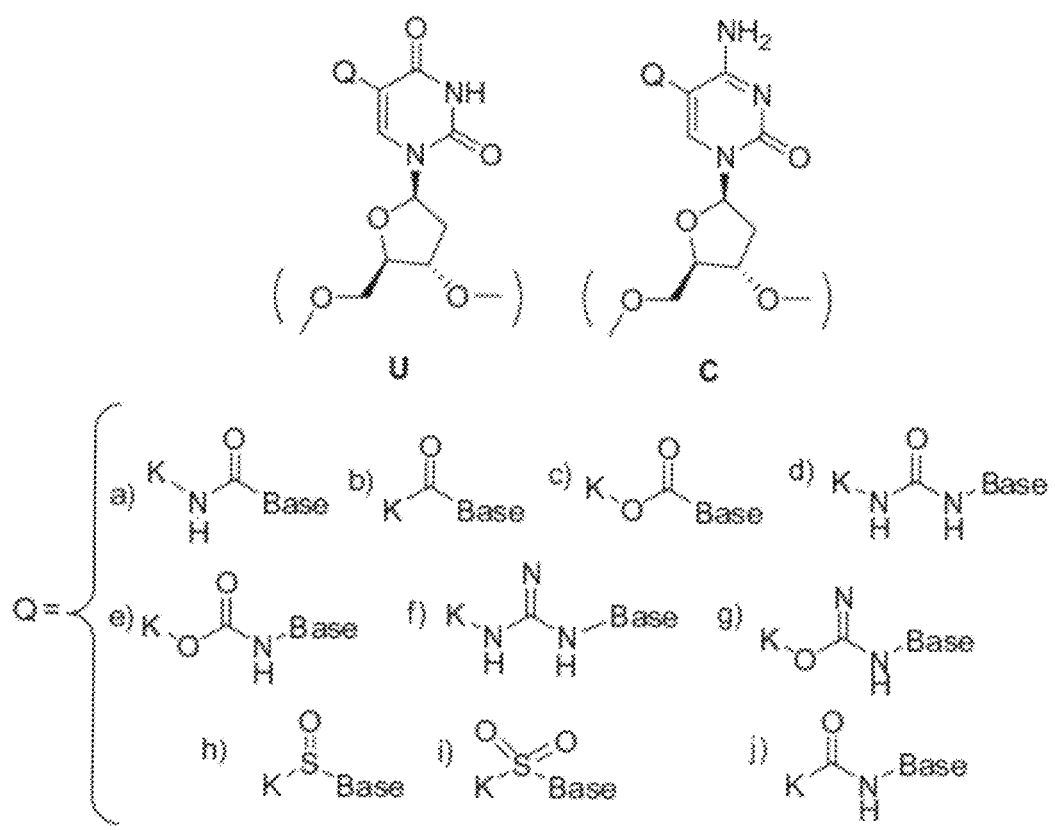
FIG. 9 illustrates examples of C-5 modified pyrimidines which may be used in the methods of making aptamers described herein.
Figure 9:
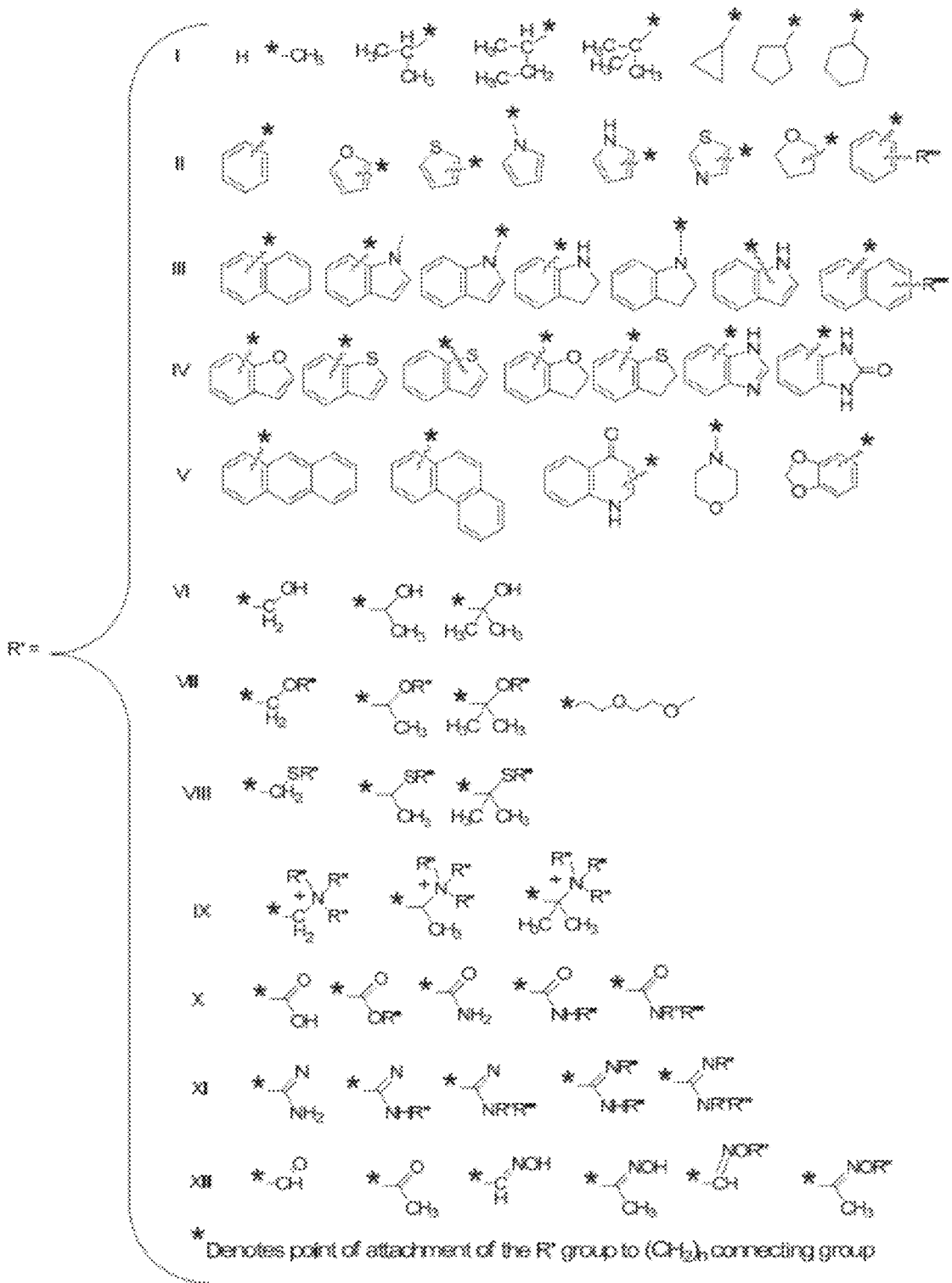

As used herein, the term "C-5 modified pyrimidine" refers to a pyrimidine with a modification at the C-5 position including, but not limited to, those moieties illustrated in FIG. 9. Examples of a C-5 modified pyrimidine include those described in U.S. Pat. Nos. 5,719,273 and 5,945,527. Examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), tyrosylcarboxyamide (alternatively tyrosylaminocarbonyl) (Tyr), 2-naphthylmethylcarboxyamide (alternatively 2-naphthylmethylaminocarbonyl) (2Nap) and phenethyl-1-carboxyamide (alternatively phenethyl-1-aminocarbonyl) (PE), as illustrated immediately below.

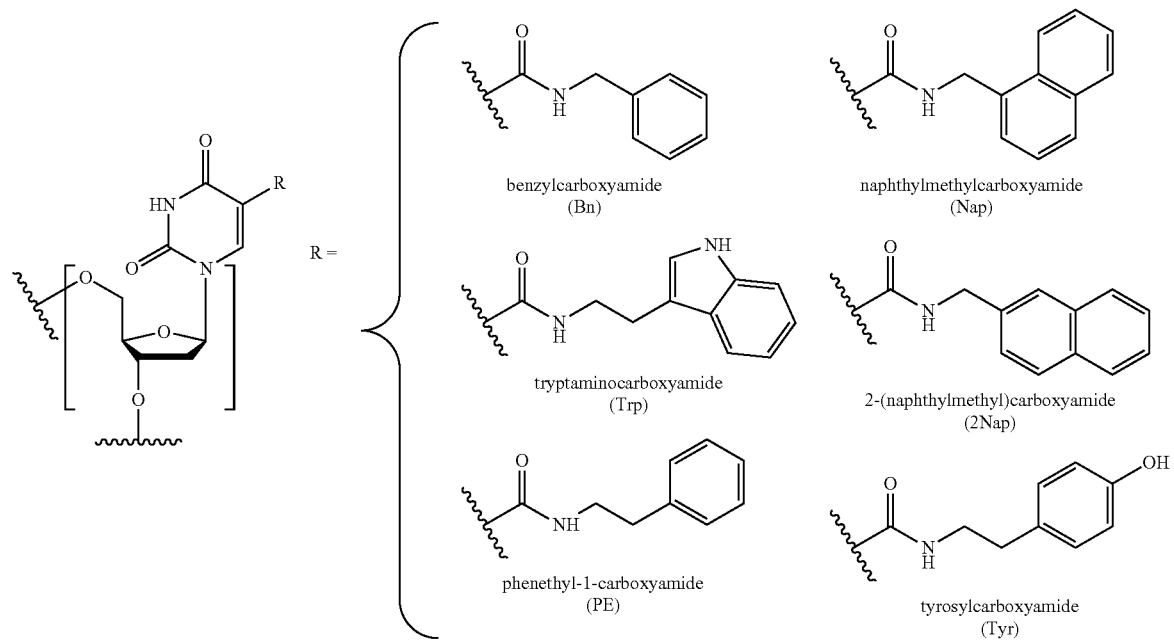

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-naphthylmethylcarboxyamide)-2'-deoxyuridine (NapdU), 5-(N-naphthylmethylcarboxyamide)-2'-O-methyluridine, 5-(N-naphthylmethylcarboxyamide)-2'-fluorouridine, 5-(N-tyrosylcarboxyamide)-2'-deoxyuridine (TyrdU), 5-(N-tyrosylcarboxyamide)-2'-O-methyluridine, 5-(N-tyrosylcarboxyamide)-2'-fluorouridine, 5-(N-(2-naphthylmethyl)carboxyamide)-2'-deoxyuridine (2NapdU), 5-(N-(2-naphthylmethyl)carboxyamide)-2'-O-methyluridine, 5-(N-(2-naphthylmethyl)carboxyamide)-2'-fluorouridine, 5-(N-phenethyl-1-carboxyamide)-2'-deoxyuridine (PEdU), 5-(N-phenethyl-1-carboxyamide)-2'-O-methyluridine, or 5-(N-phenethyl-1-carboxyamide)-2'-fluorouridine.

If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

As used herein, the term "at least one pyrimidine," when referring to modifications of a nucleic acid, refers to one or more, two or more, three or more, four or more, five or more, or all pyrimidines in the nucleic acid, indicating that any or all occurrences of any or all of C, T, or U in a nucleic acid may be modified or not.

As used herein, the terms "kinetically challenge" and "kinetic challenge" refer to a process of enrichment for an aptamer affinity complex from a set of complexes that includes an aptamer affinity complex and non-specific complexes, by applying kinetic pressure and making use of the different affinity characteristics of the constituents of such classes of complexes, including dissociation rates. A kinetic challenge generally results in an increase in specificity, since aptamer-non-target complexes are typically reduced compared to aptamer-target complexes. As used herein, the term "kinetic pressure" refers to a means for providing an opportunity for the natural dissociation of complexes and/or inhibiting the rebinding of molecules that dissociate from a complex naturally. Kinetic pressure can be applied by the addition of a competitor molecule, or by sample dilution, or by extensive washes when complexes are bound to a solid support, or by any other means known to one skilled in the art. As one of ordinary skill in the art will appreciate, because a kinetic challenge generally depends upon the differing dissociation rates of aptamer affinity complexes and aptamer-non-target complexes, the duration of the kinetic challenge is chosen so as to retain a high proportion of aptamer affinity complexes while substantially reducing the number of aptamer-non-target complexes. For a kinetic challenge to be effective, the dissociation rate for the aptamer affinity complex is preferably significantly lower than those for aptamer-non-target complexes. Since an aptamer can be selected to include particular properties, the constituents of an aptamer affinity complex can be designed to have a comparatively low dissociation rate, i.e. slow off rate.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix formation, wherein the aptamer is not a nucleic acid having the known physiological function of being bound by the target molecule. Aptamers to a given target include nucleic acids that are identified from a candidate mixture of nucleic acids, where the aptamer is a ligand of the target, by a method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby aptamers of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded or triple stranded regions.

As used herein, IUPAC nucleotide ambiguity codes are: M=A or C; R=A or G; W=A or N; S=C or G; Y=C or N; K=G or N(N represents the pool-specific modified dU).

As used herein, "plateau" refers to a region of a binding curve (in which the fraction of aptamers bound increases up the y-axis and the concentration of target increases to the right on the x-axis) where a plateau is reached as increasing target concentration causes relatively little change in the fraction of aptamers bound to target. The plateau percentage provided herein is relative to 100% of aptamers being bound to target.

As used herein, "protein" is used synonymously with "peptide", "polypeptide", or "peptide fragment." A "purified" polypeptide, protein, peptide, or peptide fragment is substantially free of cellular material or other contaminating proteins from the cell, tissue, or cell-free source from which the amino acid sequence is obtained, or substantially free from chemical precursors or other chemicals when chemically synthesized.

As used herein, "pull-down assay" refers to an assay which comprises removal of a target from solution wherein the removal is accomplished by a selective affinity interaction between the target and a second molecule. In one embodiment, the molecule having selective affinity for the target molecule is an aptamer. In another embodiment, the molecule having selective affinity for the target is an antibody.

As used herein, "PCR" refers to a polymerase chain reaction used to amplify the copy number of a DNA molecule. As used herein, "qPCR" or "quantitative PCR" refers to a polymerase chain reaction that is used to amplify and simultaneously quantify a targeted DNA molecule.

As used herein, "sandwich assay" refers to an assay capable of detecting the presence of or quantitating the amount of a target of interest. The assay requires the use of two different affinity molecules capable of binding two different, non-overlapping (noncompetitive) regions on a target of interest. Affinity molecules include but are not limited to aptamers and antibodies.

As used herein, "substrate" refers to a surface, including but not limited to the surface of a plate, bead or membrane to which an organic molecule can attach. A substrate may or may not comprise a first molecule that mediates attachment of a second molecule, such as a substrate comprising streptavidin which can mediate attachment of biotin or a molecule comprising a biotin moiety. In one embodiment, the substrate is nitrocellulose.

As used herein, "test sample" refers to a sample in which the presence or amount of one or more analytes of interest (e.g. *C. difficile* toxin A, toxin B, binary toxin A chain, or binary toxin B chain) are unknown and to be determined in an assay, preferably a diagnostic test comprising an aptamer. In one embodiment, the test sample can be a "biological sample" such as cellular and non-cellular biological material, including, but not limited to, tissue samples, blood, serum, other bodily fluids, and excrement. In another embodiment, the test sample can be an "environmental sample" which can be obtained from water, soil or air. Normally no prior culturing is necessary for detection of *C. difficile* in environmental samples.

The SELEX Method

The terms "SELEX" and "SELEX process" are used interchangeably herein to refer generally to a combination of (1) the selection of nucleic acids that interact with a target molecule in a desirable manner, for example binding with high affinity to a protein, with (2) the amplification of those selected nucleic acids. The SELEX process can be used to identify aptamers with high affinity to a specific target molecule or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: ChemiSELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication No. 2009/0098549, entitled "SELEX and PHOTOSELEX," which describes nucleic acid libraries having expanded physical and chemical properties and their use in SELEX and photoSELEX.

The nuclease resistant oligonucleotides include at least one pyrimidine modified at the C-5 position with a group selected from those set forth in FIG. 9. In various embodiments, the modifications include substitution of deoxyuridine at the C-5 position with a substituent independently selected from: benzylcarboxyamide (Bn), naphthylmethylcarboxyamide (Nap), tryptaminocarboxyamide (Trp), tyrosylcarboxyamide (Tyr), (2-naphthylmethyl)carboxyamide (2Nap), and phenethyl-1-carboxyamide (PE) as illustrated above.

SELEX can also be used to identify aptamers that have desirable off-rate characteristics. See U.S. Patent Publication No. 2009/0004667, entitled "Method for Generating Aptamers with Improved Off-Rates," which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates dissociate and do not reform, while complexes with slow dissociation rates remain intact. Additionally, the methods include the use of modified nucleotides in the production of candidate nucleic acid mixtures to generate aptamers with improved off-rate performance (see U.S. Patent Publication No. 2009/0098549, entitled "SELEX and PhotoSELEX").

"Target" or "target molecule" or "target" refers herein to any compound upon which a nucleic acid can act in a desirable manner. A target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector may be a suitable target. Molecules of any size can serve as targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein." In the instant case, the targets include *C. difficile* toxin A, toxin B, binary toxin, binary toxin A chain, or binary toxin B chain.

Methods of Identifying or Producing an Aptamer to a *C. difficile* Toxin

The present disclosure provides methods of identifying or producing a slow off-rate aptamer that binds to a toxin produced by *C. difficile* wherein said toxin is selected from toxin A, toxin B, binary toxin A chain, and binary toxin B chain, the method comprising:

(a) preparing a candidate mixture of nucleic acids, wherein the candidate mixture comprises modified nucleic acids in which one, several or all pyrimidines in at least one, or each, nucleic acid of the candidate mixture comprises a chemical modification at a C-5 position; (b) contacting the candidate mixture with a target which is said toxin produced by *C. difficile* and exposing the candidate mixture to a slow off-rate enrichment process, wherein nucleic acids having a slow rate of dissociation from the target relative to other nucleic acids in the candidate mixture bind the target, forming nucleic acid-target molecule complexes; (c) partitioning slow off-rate nucleic acids from the candidate mixture; and (d) amplifying the slow off-rate nucleic acids to yield a mixture of nucleic acids enriched in nucleic acid sequences that are capable of binding to the target molecule with a slow off-rate, whereby a slow off-rate aptamer to the target molecule may be identified. The methods of identifying or producing a slow off rate aptamer to a *C. difficile* toxin may comprise at least one pyrimidine wherein a chemical modification at a C-5 position is independently chosen from at least one of the modifications shown in FIG. 9. The methods of identifying or producing a slow off rate aptamer to a *C. difficile* toxin may comprise at least one pyrimidine wherein a chemical modification at a C-5 position is independently chosen from benzylcarboxyamide, naphthylmethylcarboxyamide, tryptaminocarboxyamide, tyrosylcarboxyamide, 2-naphthylmethylcarboxyamide and phenethyl-1-carboxyamide. The methods of identifying or producing a slow off rate aptamer to a *C. difficile* toxin may comprise at least one additional chemical modification, wherein said at least one additional chemical modification is a chemical substitution at one or more positions independently selected from the group consisting of a ribose position, a deoxyribose position, a phosphate position, and a base position. Further, the methods of identifying or producing a slow off rate aptamer to a *C. difficile* toxin may comprise at least one additional chemical modification, wherein said at least one additional chemical modification is independently selected from the group consisting of a 2'-position sugar modification, a 2'-amino (2'—NH$_2$), a 2'-fluoro (2'-F), a 2'-β-methyl (2'-OMe) a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap. The methods of identifying or producing a slow off rate aptamer to a *C. difficile* toxin may comprise a slow off-rate enrichment process selected from incubation of a candidate mixture with a competitor molecule, dilution of a candidate mixture, or dilution of a candidate mixture in the presence of a competitor molecule.

The present disclosure further provides methods of producing an aptamer having a slow rate of dissociation from a toxin produced by *C. difficile* wherein said toxin is selected from toxin A, toxin B, binary toxin A chain, and binary toxin B chain, said method comprising the step of preparing or synthesizing an aptamer based on a nucleic acid sequence identified by a process comprising the steps of: (a) preparing a candidate mixture of nucleic acids, wherein the candidate mixture comprises modified nucleic acids in which one, several or all pyrimidines in at least one, or each, nucleic acid of the candidate mixture comprises a chemical modification at a C-5 position; (b) contacting the candidate mixture with a target which is said toxin produced by *C. difficile* and exposing the candidate mixture to a slow off-rate enrichment process, wherein nucleic acids having a slow rate of dissociation from the target molecule relative to other nucleic acids in the candidate mixture bind the target molecule, forming nucleic acid-target molecule complexes; (c) partitioning slow off-rate nucleic acids from the candidate mixture; and (d) amplifying the slow off-rate nucleic acids to yield a mixture of nucleic acids enriched in nucleic acid sequences that are capable of binding to the target molecule with a slow off-rate, whereby a slow off-rate aptamer to the target molecule is identified. Such methods of producing an aptamer having a slow rate of dissociation from a *C. difficile* toxin may comprise at least one pyrimidine wherein a chemical modification at a C-5 position is independently chosen from at least one of the modifications shown in FIG. 9. The methods of producing an aptamer having a slow rate of dissociation from a *C. difficile* toxin may comprise at least one pyrimidine wherein a chemical modification at a C-5 position is independently chosen from benzylcarboxyamide, naphthylmethylcarboxyamide, tryptaminocarboxyamide, tyrosylcarboxyamide, 2-naphthylmethylcarboxyamide and phenethyl-1-carboxyamide. The methods of producing an aptamer having a slow rate of dissociation from a *C. difficile* toxin may comprise at least one additional chemical modification, wherein said at least one additional chemical modification is a chemical substitution at one or more positions independently selected from the group consisting of a ribose position, a deoxyribose position, a phosphate position, and a base position. Further, the methods of producing an aptamer having a slow rate of dissociation from a *C. difficile* toxin may comprise at least one additional chemical modification, wherein said at least one additional chemical modification is independently selected from the group consisting of a 2'-position sugar modification, a 2'-amino (2'-NH$_2$), a 2'-fluoro (2'-F), a 2'-β-methyl (2'-OMe) a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap. The methods of producing an aptamer having a slow rate of dissociation from a *C. difficile* toxin may comprise a slow off-rate enrichment process selected from incubation of a candidate mixture with a competitor molecule, dilution of a candidate mixture, or dilution of a candidate mixture in the presence of a competitor molecule.

The present disclosure further provides methods for producing a nuclease resistant aptamer that binds to a toxin produced by *C. difficile* wherein said toxin is selected from toxin A, toxin B, binary toxin A chain, and binary toxin B chain, the method comprising preparing or synthesizing said nuclease resistant aptamer based on a nucleic acid sequence identified by a process comprising: (a) preparing a candidate mixture of modified nucleic acids, wherein the candidate mixture comprises modified nucleic acids in which at least one pyrimidine in at least one, or in each, nucleic acid of the candidate mixture comprises a chemical modification at a C-5 position; (b) contacting the candidate mixture with a target which is said toxin produced by *C. difficile*, wherein nucleic acids having an increased affinity to the target molecule relative to other nucleic acids in the candidate mixture bind the target molecule, forming nucleic acid-target molecule complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target molecule with increased affinity and that are nuclease resistant, whereby a nuclease resistant aptamer to the target molecule is identified. The methods of producing a nuclease resistant aptamer to a *C. difficile* toxin may comprise at least one pyrimidine wherein a chemical modification at a C-5 position is independently chosen from at least one of the modifications shown in FIG. 9. The methods of producing a nuclease resistant aptamer to a *C. difficile* toxin may comprise at least one pyrimidine wherein a chemical modification at a C-5 position is independently chosen from benzylcarboxyamide, naphthylmethylcarboxyamide, tryptaminocarboxyamide, tyrosylcarboxyamide, 2-naphthylmethylcarboxyamide and phenethyl-1-carboxyamide. The methods of producing a nuclease resistant aptamer to a *C. difficile* toxin may comprise at least one additional chemical modification, wherein said at least one additional chemical modification is a chemical substitution at one or more positions independently selected from the group consisting of a ribose position, a deoxyribose position, a phosphate position, and a base position. Further, the methods of producing a nuclease resistant aptamer to a *C. difficile* toxin may comprise at least one additional chemical modification, wherein said at least one additional chemical modification is independently selected from the group consisting of a 2'-position sugar modification, a 2'-amino (2'-$NH_2$), a 2'-fluoro (2'-F), a 2'-O-methyl (2'-OMe) a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap.

Aptamers

The aptamers to *C. difficile* toxins of the instant disclosure were identified using the improved SELEX method for identifying aptamers having slow off-rates, as described above. The form of *C. difficile* toxins used in the selection process were recombinant toxins prepared by PCR amplification of desired gene fragments from *C. difficile* genomic DNA, as described in Example 1.

SELEX was performed using purified His-tag proteins obtained from over-expression of cloned *C. difficile* toxin gene fragments. Libraries of 40mer random sequences were used that contained one of six modified nucleotides, 5-tyrosylcarboxyamide-dU (TyrdU), 5-benzylcarboxyamide-dU (BndU), 5-naphthylmethylcarboxyamide-dU (NapdU), 5-tryptaminocarboxyamide-dU (TrpdU), 5-(2-naphthylmethyl)carboxyamide (2NapdU), or 5-phenethyl-1-carboxyamide (PEdU) instead of dU. Seven or eight rounds of selection were carried out, and a kinetic challenge with dextran sulfate was applied in rounds 2-8. The aptamer pools obtained after the last round of SELEX were tested for affinity to their targets in filter binding assays, and the $K_d$'s and plateaus were determined (Table 2). All pools with sufficient affinity ($K_d$ of ~10 nM or below) were cloned and the sequences of at least 48 clones per pool were determined.

Aptamers to Toxin A

For toxin A, the aptamer pool 4943 (TrpdU) had excellent affinity with a $K_d$=2.42 nM. Pools 4936 (TyrdU) and 4939 (NapdU) were active, with $K_d$'s of 11.5 and 10.8 nM, respectively. Pools 5564 (2NapdU) and 5577 (2NapdU) had good affinity, with $K_d$'s of 4.63 and 6.40 nM. For toxin A, the aptamer pool 5570 (PEdU) was the best, with a $K_d$=1.61 nM. Aptamer clones with good affinities for toxin A were isolated from all of the pools with TrpdU, TyrdU, NapdU, 2NapdU, and PEdU modified nucleotides (Table 3); the sequences of *C. difficile* toxin A aptamers are listed on Table 4. In addition to identifying aptamer clones with good binding affinity to toxin A, consensus sequences between such aptamer clones were identified.

The leading aptamer clone from pool 5570 (PEdU) was 5570-54, with $K_d$=0.12 nM for the recombinant toxin A and $K_d$=6.91 nM for native toxin A.

Some aptamer clones demonstrated excellent affinity for both recombinant toxin A and native toxin A, e.g. aptamer clone 4943-51 (TrpdU) had $K_d$=1.23 nM for recombinant toxin A and $K_d$=1.78 nM for native toxin A; aptamer clone 5564-49 (2NapdU) had $K_d$=1.13 nM for recombinant toxin A and $K_d$=1.78 nM for native toxin A.

Some aptamer clones demonstrated relatively little drop off of affinity between recombinant toxin A and native toxin A, e.g. aptamer clone 5577-1 (2NapdU) had $K_d$=1.59 nM for recombinant toxin A and $K_d$=4.97 nM for native toxin A; aptamer clone 5577-3 (2NapdU) had $K_d$=1.73 nM for recombinant toxin A and $K_d$=5.52 nM for native toxin A; aptamer clone 4943-60 (TrpdU) had $K_d$=2.65 nM for recombinant toxin A and $K_d$=4.57 nM for native toxin A.

In addition to identifying aptamer clones with good binding affinity to toxin A, consensus sequences between such aptamer clones were identified.

Aptamers to Toxin B

The affinities of aptamers for toxin B were generally very good and correlated well between the 68.8 kDa amino-terminal catalytic domain of *C. difficile* toxin B fragment that had been used in SELEX and the 270 kDa native, full-length toxin B. Aptamer clones with sub-nanomolar $K_d$'s for toxin B were isolated from all of the pools with TyrdU, BndU, NapdU, TrpdU, 2NapdU and PEdU modified nucleotides (Table 5); the sequences of *C. difficile* toxin B aptamers are listed in Table 6, with the best clones shown in bold.

The highest-affinity aptamers were clones with NapdU or TrpdU modified nucleotides. Five aptamers demonstrated very low $K_d$'s of <0.1 nM: aptamer clone 4940-1 (NapdU) had $K_d$=0.04 nM for recombinant toxin B and $K_d$=0.06 for native toxin B; aptamer clone 4940-23 (NapdU) had $K_d$=0.07 nM for recombinant toxin B and $K_d$=0.09 nM for native toxin B; aptamer clone 4940-27 (NapdU) had $K_d$=0.10 nM for recombinant toxin B and $K_d$=0.09 nM for native toxin B; aptamer clone 4944-5 (TrpdU) had $K_d$=0.08 nM for recombinant toxin B and $K_d$=0.09 nM for native toxin B; and aptamer clone 4944-30 (TrpdU) had $K_d$=0.06 nM for recombinant toxin B and $K_d$=0.08 nM for native toxin B. Aptamer clones with good affinities for toxin B were isolated from all of the pools with TrpdU, TyrdU, NapdU, 2NapdU, BndU and PEdU modified nucleotides (Table 5); the sequences of *C. difficile* toxin B aptamers are listed on Table 6. In addition to identifying aptamer clones with good binding affinity to toxin B, consensus sequences between such aptamer clones were identified.

Aptamers to Binary Toxin (A chain)

SELEX with the recombinant binary toxin A chain (CdtA) yielded active aptamers with TrpdU, 2NapdU and PEdU modified nucleotides (Table 7). The sequences and common sequence patterns of CdtA aptamers are shown in Table 8. Cloning of pool 4758 (TrpdU) revealed clone 4758-6 which comprised 18% of the sequences in that pool and showed good affinity ($K_d$=0.86 nM) to CdtA binary toxin. Twenty sequences from 2NapdU pools were obtained, most of them with subnanomolar affinity, and several sequence patterns shared between these 2NapdU clones were identified. PEdU pools contained five active aptamers.

Aptamers to Binary Toxin (B chain)

SELEX with recombinant binary toxin B chain (CdtB) yielded active aptamers with 2NapdU modified nucleotides (Table 9). The sequences and common sequence patterns of CdtB aptamers are shown in Table 10. The most active clone was 5556-51 $K_d$=1.68 nM.

The present disclosure provides aptamers to toxins produced by *C. difficile* identified using the SELEX method and listed in Tables 4, 6, 8 and 10. Aptamers to toxins produced by *C. difficile* that are substantially homologous to any of the listed aptamers and that have a substantially similar ability to bind the respective toxin produced by *C. difficile* as that of an aptamer selected from the group of aptamers set forth in Tables 4, 6, 8 and 10 are also encompassed by the present disclosure. Further, aptamers to the respective toxin produced by *C. difficile* that have substantially the same structural form as the aptamers identified herein and that have a substantially similar ability to bind the respective toxin produced by *C. difficile* as that of an aptamer selected from the group of aptamers set forth in Tables 4, 6, 8 and 10 are also encompassed by the present disclosure.

In one aspect, the present disclosure provides an aptamer that specifically binds to a toxin produced by *C. difficile* and includes a primary nucleic acid sequence. In one embodiment, the primary nucleic acid sequence is selected from a sequence disclosed in Table 4, 6, 8, or 10. In other embodiments, the primary nucleic acid sequence is selected such that it is at least about 75% identical, at least about 80% identical, at least about 85% identical, at least about 90% identical, or at least about 95% identical to a primary nucleic acid sequence disclosed in Table 4, 6, 8 or 10.

The terms "sequence identity", "percent sequence identity", "percent identity", "% identical", "% identity", and variations thereof, when used in the context of two or more nucleic acid sequences, are used interchangeably to refer to two or more sequences or subsequences that are the same or have a specified percentage of nucleotides that are the same, when compared and aligned for maximum correspondence, as measured using a sequence comparison algorithm or by visual inspection. For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 1981. 2:482, by the homology alignment algorithm of Needleman and Wunsch, J. Mol. Biol., 1970. 48:443, by the search for similarity method of Pearson and Lipman, Proc. Nat'l. Acad. Sci. USA, 1988. 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul et al., J. Mol. Biol., 1990. 215:403-410 and Altschul et al., Nucleic Acids Res., 1997. 15:3389-3402. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis et al., Nucleic Acids Res., 2004. 32:W20-W25.

As used herein, when describing the percent identity of a nucleic acid, such as an aptamer to a toxin produced by *C. difficile*, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be any one of the entire nucleotide sequences shown in Table 4, 6, 8 or 10, or any fragment of any of these sequences.

In one aspect, a consensus sequence selected from the group consisting of SEQ ID NOs: 5, 11, 15, 23, 28, 32, 47, 66, 75, 83, 90, 95, 98, 110, 124, 125, 134, 139, 145, 151, 152 or 157 can be modified to comprise at least one insertion, one deletion and/or one transposition. In one embodiment, the consensus sequence selected from the group consisting of SEQ ID NOs: 5, 11, 15, 23, 28, 32, 47, 66, 75, 83, 90, 95, 98, 110, 124, 125, 134, 139, 145, 151, 152 or 157 is modified such that at least one nucleotide is inserted into the consensus sequence. In another embodiment, a consensus sequence selected from the group consisting of SEQ ID NOs: 5, 11, 15, 23, 28, 32, 47, 66, 75, 83, 90, 95, 98, 110, 124, 125, 134, 139, 145, 151, 152 or 157 is modified such that at least one nucleotide is deleted from the consensus sequence. In another embodiment, a consensus sequence selected from the group consisting of SEQ ID NOs: 5, 11, 15, 23, 28, 32, 47, 66, 75, 83, 90, 95, 98, 110, 124, 125, 134, 139, 145, 151, 152 or 157 is modified such that at least one nucleotide is transposed from one location in the consensus sequence to another location in the consensus sequence. It is also recognized that a consensus sequence selected from the group consisting of SEQ ID NOs: 5, 11, 15, 23, 28, 32, 47, 66, 75, 83, 90, 95, 98, 110, 124, 125, 134, 139, 145, 151, 152 or 157 may be modified to comprise a combination of one or more insertions, deletions or transpositions while still maintaining adequate affinity to a toxin produced by *C. difficile* to have utility in a diagnostic assay.

In various embodiments, the aptamer to a toxin produced by *C. difficile* includes a sequence of contiguous nucleotides that are identical to a sequence of contiguous nucleotides included in any of the nucleotide sequences shown in Table 4, 6, 8 or 10. In various embodiments, the sequence of contiguous nucleotides in the aptamer to a toxin produced by *C. difficile* can include any number of nucleotides that are identical to the same number of nucleotides in a sequence of contiguous nucleotides included in any of the sequences shown in Table 4, 6, 8 or 10. In various embodiments, the sequence of contiguous nucleotides in the aptamer to a toxin produced by *C. difficile* includes a sequence of from about 4 to about 30 contiguous nucleotides that are identical to a sequence of from about 4 to about 30 contiguous nucleotides included in any of the sequences shown in Table 4, 6, 8 or 10. In an exemplary embodiment, the aptamer to a toxin produced by C. difficile includes a sequence of 40 contiguous nucleotides that are identical to a sequence of 40 contiguous nucleotides included in any of the sequences shown in Table 4, 6, 8 or 10 which has 40 or more contiguous nucleotide. In an exemplary embodiment, the aptamer to a toxin produced by C. difficile includes a sequence of 30 contiguous nucleotides that are identical to a sequence of 30 contiguous nucleotides included in any of the sequences shown in Table 4, 6, 8 or 10. In another exemplary embodiment, the aptamer to a toxin produced by C. difficile includes a sequence of 20 contiguous nucleotides that are identical to a sequence of 20 contiguous nucleotides included in any the sequences shown in Table 4, 6, 8 or 10. In yet another exemplary embodiment, the aptamer to a toxin produced by C. difficile includes a sequence of 8 contiguous nucleotides that are identical to a sequence of 8 contiguous nucleotides included in any of the sequences shown in Table 4, 6, 8 or 10. In yet another exemplary embodiment, the aptamer to a toxin produced by C. difficile includes a sequence of 4 contiguous nucleotides that are identical to a sequence of 4 contiguous nucleotides included in any of the sequences shown in Table 4, 6, 8 or 10.

In one embodiment, the aptamer to toxin A is selected from the group consisting of SEQ ID NOS: 1-4, 6-10, 12-14, 16-22, 24-27, or 29-31. In yet another embodiment, the aptamer to toxin A is derived from a consensus sequence selected from any one of SEQ ID NOS: 5, 11, 15, 23 or 28. In one embodiment, the aptamer to toxin A is at least about 95% identical, at least about 90% identical, at least about 85% identical, at least about 80% identical, or at least about 75% identical to any of SEQ ID NOS: 1-31. In another embodiment, the aptamer to toxin A includes a sequence from any of SEQ ID NOS: 1-31 or fragments of any of these.

In one embodiment, the aptamer to toxin B is selected from the group consisting of SEQ ID NOS: 33-46, 48-65, 67-74, 76-82, 84-89, 91-94, 96-97, or 99-108. In yet another embodiment, the aptamer to toxin B is derived from a consensus sequence selected from any one of SEQ ID NOS: 32, 47, 66, 75, 83, 90, 95 and 98. In one embodiment, the aptamer to toxin B is at least about 95% identical, at least about 90% identical, at least about 85% identical, at least about 80% identical, or at least about 75% identical to any of SEQ ID NOS: 32-108. In another embodiment, the aptamer to toxin B includes a sequence from any of SEQ ID NOS: 32-108 or fragments of any of these.

In one embodiment, the aptamer to binary toxin A chain is selected from the group consisting of SEQ ID NOS: 109, 111-123, 126-133, 135-138, 140-144, or 146-150. In yet another embodiment, the aptamer to binary toxin A chain is derived from a consensus sequence selected from any one of SEQ ID NOS: 110, 124-125, 134, 139, or 145. In one embodiment, the aptamer to binary toxin A chain is at least about 95% identical, at least about 90% identical, at least about 85% identical, at least about 80% identical, or at least about 75% identical to any of SEQ ID NOS: 109-150. In another embodiment, the aptamer to binary toxin A chain includes a sequence from any of SEQ ID NOS: 109-150 or fragments of any of these.

In one embodiment, the aptamer to binary toxin B chain is selected from the group consisting of SEQ ID NOS: 153-156, 158-162. In yet another embodiment, the aptamer to binary toxin B chain is derived from the consensus sequence of SEQ ID NOS: 151, 152 or 157. In one embodiment, the aptamer to binary toxin B chain is at least about 95% identical, at least about 90% identical, at least about 85% identical, at least about 80% identical, or at least about 75% identical to any of SEQ ID NOS: 151-162. In another embodiment, the aptamer to binary toxin B chain includes a sequence from any of SEQ ID NOS: 151-162 or fragments of any of these.

The aptamer to a toxin produced by C. difficile can contain any number of nucleotides in addition to the region which binds the C. difficile toxin. In various embodiments, the aptamer can include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

The aptamer to a toxin produced by C. difficile can be selected to have any suitable dissociation constant ($K_d$) for the respective toxin. In an exemplary embodiment, the aptamer to a toxin produced by C. difficile has a dissociation constant ($K_d$) for the respective toxin of about 10 nM or less. In another exemplary embodiment, the aptamer to a toxin produced by C. difficile has a dissociation constant ($K_d$) for the respective toxin of about 15 nM or less. In yet another exemplary embodiment, the aptamer to a toxin produced by C. difficile has a dissociation constant ($K_d$) for the respective toxin of about 20 nM or less. In yet another exemplary embodiment, the aptamer to a toxin produced by C. difficile has a dissociation constant ($K_d$) for the respective toxin of about 25 nM or less. A suitable dissociation constant can be determined with a binding assay using a multi-point titration and fitting the equation $y=(max-min)(Protein)/(K_d+Protein)+min$. It is to be understood that the determination of dissociation constants is highly dependent upon the conditions under which they are measured and thus these numbers may vary significantly with respect to factors such as equilibration time, etc. In other embodiments, the aptamer to a toxin produced by C. difficile is an aptamer with a $K_d$ that is less than or equal to the $K_d$ of an aptamer selected from the sequences disclosed in Tables 4, 6, 8 and 10.

Since the binary toxin is composed of an A chain and a B chain, more efficient binding may be achieved by using a dimeric or other multimeric form of aptamer. Thus, in another embodiment, the aptamer is a multimerization of any combination of the sequences of Table 8 and the sequences of Table 10. The same strategies could be applied to any aptamer sequence with the appropriate binding characteristics for binary toxin. In another embodiment, an aptamer for A chain could be used in conjunction with an aptamer for B chain to detect binary toxin in a sandwich assay.

Kits Comprising Aptamers to Toxins Produced by C. difficile

The present disclosure provides kits comprising any of the aptamers to toxins produced by C. difficile described herein. Such kits can comprise, for example, (1) at least one aptamer to a toxin produced by C. difficile; and (2) at least one diagnostic testing reagent, such as a solvent or solution. Additional kit components can optionally include, for example: (1) at least one container, vial or similar apparatus for holding and/or mixing the kit components; and (2) apparatus for collecting a sample to be tested for the presence of a C. difficile toxin.

Methods of Detecting Toxins Produced by C. difficile

The present disclosure provides methods of detecting the presence of a C. difficile toxin in a test sample comprising contacting said test sample with an aptamer that binds to a toxin produced by C. difficile wherein said toxin is selected from toxin A, toxin B, binary toxin A chain, and binary toxin B chain. Further disclosed are methods of detecting the presence of a *C. difficile* toxin comprising aptamers which comprise at least one pyrimidine modified at a C-5 position wherein said at least one pyrimidine modified at a C-5 position comprises a C-5 modification independently chosen from at least one of the modifications shown in FIG. 9. Also disclosed are methods of detecting the presence of a *C. difficile* toxin comprising aptamers which comprise at least one pyrimidine modified at a C-5 position wherein said at least one pyrimidine modified at a C-5 position comprises a C-5 modification independently chosen from benzylcarboxyamide, naphthylmethylcarboxyamide, tryptaminocarboxyamide, tyrosylcarboxyamide, 2-naphthylmethylcarboxyamide and phenethyl-1-carboxyamide. The methods of detecting a *C. difficile* toxin disclosed herein may comprise an aptamer which comprises at least one additional chemical modification, wherein said at least one additional chemical modification is a chemical substitution at one or more positions independently selected from the group consisting of a ribose position, a deoxyribose position, a phosphate position, and a base position. Further, the methods of detecting a *C. difficile* toxin disclosed herein may comprise at least one additional chemical modification is independently selected from the group consisting of a 2'-position sugar modification, a 2'-amino (2'-NH$_2$), a 2'-fluoro (2'-F), a 2'-O-methyl (2'-OMe) a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap.

The present disclosure provides methods of detecting the presence of a *C. difficile* toxin in a test sample wherein the method of detecting is selected from a pull-down assay, dot blot assay, PCR assay or sandwich assay.

The present disclosure further provides methods of detecting the presence of *C. difficile* toxin A in a test sample comprising contacting said test sample with an aptamer comprising a sequence selected from the group consisting of SEQ ID NOS: 1-4, 6-10, 12-14, 16-22, 24-27, or 29-31 or a fragment thereof. Methods of detecting the presence of *C. difficile* toxin A in a test sample may comprise a pull-down assay, dot blot assay, PCR assay or sandwich assay. Sandwich assays used for detecting the presence of *C. difficile* toxin A may be selected from an aptamer-target-antibody assay, antibody-target-aptamer assay, and aptamer-target-aptamer assay. Methods of detecting the presence of *C. difficile* toxin A in a test sample may provide a quantitative measure of toxin A.

The present disclosure further provides methods of detecting the presence of *C. difficile* toxin B in a test sample comprising contacting said test sample with an aptamer comprising a sequence selected from the group consisting of SEQ ID NOS: 33-46, 48-65, 67-74, 76-82, 84-89, 91-94, 96-97, or 99-108 or a fragment thereof. Methods of detecting the presence of *C. difficile* toxin B in a test sample may comprise a pull-down assay, dot blot assay, PCR assay or sandwich assay. Sandwich assays used for detecting the presence of *C. difficile* toxin B may be selected from an aptamer-target-antibody assay, antibody-target-aptamer assay, and aptamer-target-aptamer assay. Methods of detecting the presence of *C. difficile* toxin B in a test sample may provide a quantitative measure of toxin B.

The present disclosure further provides methods of detecting the presence of *C. difficile* binary toxin A chain in a test sample comprising contacting said test sample with an aptamer comprising a sequence selected from the group consisting of SEQ ID NOS: 109, 111-123, 126-133, 135-138, 140-144, or 146-150 or a fragment thereof. Methods of detecting the presence of *C. difficile* binary toxin A chain in a test sample may comprise a pull-down assay, dot blot assay, PCR assay or sandwich assay. Sandwich assays used for detecting the presence of *C. difficile* binary toxin A chain may be selected from an aptamer-target-antibody assay, antibody-target-aptamer assay, and aptamer-target-aptamer assay. Methods of detecting the presence of *C. difficile* binary toxin A chain in a test sample may provide a quantitative measure of binary toxin A chain.

The present disclosure further provides methods of detecting the presence of *C. difficile* binary toxin B chain in a test sample comprising contacting said test sample with an aptamer comprising a sequence selected from the group consisting of SEQ ID NOS: 153-156, 158-162 or a fragment thereof. Methods of detecting the presence of *C. difficile* binary toxin B chain in a test sample may comprise a pull-down assay, dot blot assay, PCR assay or sandwich assay. Sandwich assays used for detecting the presence of *C. difficile* binary toxin B chain may be selected from an aptamer-target-antibody assay, antibody-target-aptamer assay, and aptamer-target-aptamer assay. Methods of detecting the presence of *C. difficile* binary toxin B chain in a test sample may provide a quantitative measure of binary toxin B chain.

The present disclosure further provides methods of detecting the presence of a *C. difficile* toxin in a test sample comprising contacting said test sample with an aptamer comprising a consensus sequence selected from the group consisting of SEQ ID NOS: 5, 11, 15, 23, 28, 32, 47, 66, 75, 83, 90, 95, 98, 110, 124-125, 134, 139, 145, 151-152 and 157 or a fragment thereof. Methods of detecting the presence of a *C. difficile* toxin with an aptamer comprising such consensus sequence in a test sample may comprise a pull-down assay, dot blot assay, PCR assay or sandwich assay. Sandwich assays used for detecting the presence of a *C. difficile* toxin may be selected from an aptamer-target-antibody assay, antibody-target-aptamer assay, and aptamer-target-aptamer assay. Methods of detecting the presence of a *C. difficile* toxin in a test sample may provide a quantitative measure of such *C. difficile* toxin.

EXAMPLES

The following examples are provided for illustrative purposes only and are not intended to limit the scope of the invention as defined by the appended claims. All examples described herein should be considered in the context of standard techniques, which are well known and routine to those of skill in the art. Routine molecular biology techniques can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Example 1

SELEX with *C. difficile* Toxins A/B and Binary Toxin: Target Procurement

Target Procurement

Targets suitable for SELEX were prepared by PCR amplification of desired gene fragments from *C. difficile* genomic DNA, cloning in frame into vector pET-51b between the Strep-tag and His-tag sequences, and overexpression in *E. coli* Rosetta (Table 1). For toxin A, a recombinant polypeptide was obtained that consisted of the carboxy-terminal β-hairpin repeats 17-32. This toxin domain was chosen since a crystal structure has been published for a similar toxin A peptide of just five receptor-binding repeats (Ho, J. G., et al., Proc. Natl.

Acad. Sci. USA, 2005. 102(51): p. 18373-8). For toxin B, the amino-terminal catalytic domain was purified; a crystal structure of this domain has been obtained (Reinert, D. J., et al., J. Mol. Biol., 2005. 351(5): p. 973-81). For binary toxin, the full-length CdtA subunit but without the predicted signal sequence was produced in recombinant form (crystal structure available (Sundriyal, A., et al., J. Biol. Chem., 2009. 284(42): p. 28713-9)), and a CdtB fragment (amino acid residues 30-207) was produced that represents the so-called activation domain that has presumably been cleaved off the CdtB precursor protein (Perelle, S., et al., Infect. Immun., 1997. 65(4): p. 1402-7).

Cloning and purification of all *C. difficile* toxins is shown in FIG. 1A-1D, along with available crystal structures. The recombinant, double tagged proteins were purified via affinity chromatography on Ni-NTA agarose and streptactin agarose using standard protocols.

The aptamer pools obtained after the last round of SELEX were tested for affinity to their targets in filter binding assays, and the $K_d$'s and plateaus were determined (Table 2). For toxin A, the aptamer pool 4943 (TrpdU) had good affinity with a $K_d$=2.42 nM. Pools 4936 (TyrdU) and 4939 (NapdU) were active, with $K_d$'s of 11.5 and 10.8 nM, respectively. Pools 5564 (2NapdU) and 5577 (2NapdU) were also active, with $K_d$'s of 4.63 and 6.40 nM. For toxin A, the aptamer pool 5570 (PEdU) was the best, with a $K_d$=1.61 nM.

For toxin B, aptamer pools TyrdU, BndU, NapdU, TrpdU, 2NapdU and PEdU demonstrated excellent affinities with $K_d$'s in the range of 0.11-1.11 nM.

Binary toxin A chain was also successful in selecting high affinity aptamers and yielded pool 4758 (TrpdU) with $K_d$=0.40 nM; pool 5567 (2NapdU) with $K_d$=0.19 nM; and

TABLE 1

PCR amplification of *C. difficile* toxin genes for cloning and overexpression

| PCR amplification | | Target protein | | | |
|---|---|---|---|---|---|
| Gene | PCR primers | Amplicon (nucleotides) | Protein (UniProt) | Domain (residues) | Size (kDa) (tagged) |
| tcdA | tcdA-6 + tcdA-2 | 6751-8127 | Toxin A (TOXA_CLODI) | 2250-2709 | 57.1 |
| tcdB | tcdB-5 + tcdB-7 | 1-1638 | Toxin B (TOXB_CLODI) | 1-546 | 68.8 |
| cdtA | cdtA-1 + cdtA-2 | 103-1387 | Binary Toxin A (O32738_CLODI) | 35-463 | 54.7 |
| ctdB | cdtB-15 + cdtB-16 | 90-622 | Binary Toxin B (O32739_CLODI) | 30-207 | 26.0 |

| SEQ ID NO: | Primer | Primer Sequence (restriction sites for cloning underlined) |
|---|---|---|
| 163 | tcdA-6 | GCGCAAGCTTCTTCAAAATGGATATATTACTATTGAAAG |
| 164 | tcdA-2 | GCGCGAGCTCCATATATCCCAGGGGCTTTTAC |
| 165 | tcdB-5 | GCGCAAGCTTATGAGTTTAGTTAATAGAAAACAGTTAG |
| 166 | tcdB-7 | GCGCGAGCTCCATCTTCACCAAGAGAACCTTC |
| 167 | cdtA-1 | GCGCAAGCTTCAAGACTTACAAAGCTATAGTG |
| 168 | cdtA-2 | GCGCGAGCTCCAGGTATCAATGTTGCATCAAC |
| 169 | cdtB-15 | GCGCAAGCTTCAAACTAGTACAAGTAATC |
| 170 | cdtB-15 | GCGCGAGCTCGGTCAAAGAAATTGTTATTTGGG |

Example 2

SELEX with *C. difficile* Toxins A/B and Binary Toxin: SELEX and Pool Affinities SELEX with the purified His-tagged proteins was performed using Dynabeads® (Talon® or His-Tag) partitioning. Libraries of 40mer random sequences were used that contained one of the six modified nucleotides, 5-tyrosylcarboxyamide-dU (TyrdU), 5-benzylcarboxyamide-dU (BndU), 5-naphthylmethylcarboxyamide-dU (NapdU), 5-tryptaminocarboxyamide-dU (TrpdU), 5-(2-naphthylmethyl)carboxyamide (2NapdU), or 5-phenethyl-1-carboxyamide (PEdU) instead of dU. Seven or eight rounds of selection were carried out, and a kinetic challenge with dextrane sulfate was applied in rounds 2-8. The aptamer pools obtained after the last round of SELEX were tested for affinity to their targets in filter binding assays, and the $K_d$'s and plateaus were determined (Table 2).

pool 5574 (PEdU) with $K_d$=0.30 nM. Binary toxin B chain was used to select active pool 5556 (2NapdU), with $K_d$=7.58 nM.

All pools with sufficient affinity ($K_d$ of ~10 nM or below) were cloned and the sequences of at least 48 clones per pool were determined

TABLE 2

SELEX with *C. difficile* toxins

| Target | Library | MOD | Sample ID | Pool | $K_d$ (nM) | Plateau |
|---|---|---|---|---|---|---|
| Toxin A | 40N29.14 | TyrdU, | S247-R8-S1 | 4936 | 11.50 | 42% |
| | | BndU | S247-R8-S9 | n/a[1] | 70.30 | 40% |
| | | NapdU | S247-R8-S17 | 4939 | 10.80 | 48% |
| | | TrpdU | S247-R8-S25 | 4943 | 2.42 | 46% |

TABLE 2-continued

SELEX with *C. difficile* toxins

| Target | Library | MOD | Sample ID | Pool | $K_d$ (nM) | Plateau |
|---|---|---|---|---|---|---|
| | 40N32.24 | 2NapdU | S270-R8-S1 | 5564 | 4.63 | 42% |
| | | PEdU | S270-R8-S9 | 5570 | 1.61 | 21% |
| | | 2NapdU | S270-R8-S29 | 5577 | 6.40 | 23% |
| Toxin B | 40N29.14 | TyrdU, | S247-R8-S3 | 4937 | 0.57 | 43% |
| | | BndU | S247-R8-S11 | 4938 | 1.11 | 24% |
| | | NapdU | S247-R8-S19 | 4940 | 0.20 | 44% |
| | | TrpdU | S247-R8-S27 | 4944 | 0.24 | 43% |
| | 40N32.24 | 2NapdU | S270-R8-S5 | 5566 | 0.11 | 18% |
| | | PEdU | S270-R8-S13 | 5573 | 0.12 | 50% |
| | | 2NapdU | S270-R8-S30 | 5578 | 0.79 | 16% |
| Binary Toxin A Chain | 40N58.50 | TrpdU | S239-R7-S39 | 4758 | 0.40 | 50% |
| | 40N32.24 | 2NapdU | S261-R8-S24 | 5551 | 0.22 | 36% |
| | | PEdU | S261-R8-S32 | 5555 | 3.73 | 33% |
| | | 2NapdU | S270-R8-S6 | 5567 | 0.19 | 45% |
| | | PEdU | S270-R8-S14 | 5574 | 0.30 | 65% |
| | | 2NapdU | S270-R8-S31 | 5579 | 0.33 | 63% |
| Binary Toxin B Chain | 40N32.24 | 2NapdU | S261-R8-S33 | 5556 | 7.58 | 32% |

[1]pool not cloned due to insufficient affinity

Example 3

Toxin A Aptamer Clones

Representative clones from SELEX pools 4936 (TyrdU), 4939 (NapdU), 4943 (TrpdU), 5564 (2NapdU), 5577 (2NapdU), and 5570 (PEdU) were evaluated for affinity to toxin A in filter binding assays. Nearly all clones had good affinity to the recombinant 57.1 kDa toxin A fragment that had been used for selection, however, only some of the clones demonstrated affinity for the native, 308 kDa toxin A. This is not surprising, since some of the epitopes on the smaller, recombinant protein may not be accessible for aptamer binding of the full-length, native toxin.

The affinities ($K_d$'s) and plateaus of the binding curves are shown in Table 3 and the corresponding sequences are listed in Table 4, with the best clones shown in bold.

Clones from Pool 4936 (TyrdU): Clone 4936-4 represented 20% of the sequences in the pool and was the most active with $K_d$=3.8 nM for the recombinant toxin A domain and $K_d$=14.5 nM for native toxin A.

Clones from Pool 4939 (NapdU): Three unrelated sequences were found five times each in this pool. Clone 4939-280 was the most active clone in this pool, with $K_d$=2.34 nM for the recombinant protein and $K_d$=15.3 nM for native toxin A.

Clones from Pool 4943 (TrpdU): Four clones with good (low nanomolar) affinity for native toxin A were found in this pool. The best clone, 4943-51 ($K_d$=1.78 nM for native toxin A), made up 19% of all sequences in this pool. The other three clones had the common motif NANAnnCNNNCnnCnN (SEQ ID NO:5, N=TrpdU; n=A, G, C, or TrpdU). Clones 4943-50, 4943-60, and 4943-49 which possessed only 32 nucleotides instead of the usual 40 within the random region (Kd's, 5.60 nM, 4.57 nM, and 7.91 nM for native toxin A respectively) showed good affinity.

Clones from Pool 5564 (2NapdU): The most active clone of this pool was 5564-49 ($K_d$=1.78 nM for native toxin A). Several other clones were also present in this pool, sharing one of the three sequence patterns NAAAGNAGGN (SEQ ID NO:11) CGGGNCGNGACA-GANCGCA (SEQ ID NO:23), respectively (N=2NapdU; R=A or G; M=A or C; K=G or N).

Clones from Pool 5570 (PEdU): The leading clone, 5570-54, with $K_d$=0.12 nM for the recombinant toxin A and $K_d$=6.91 nM for native toxin A, was the most abundant sequence in this pool.

Clones from Pool 5577 (2NapdU): The active clones shared all or part of the pattern NAC-CGAACGNNnNCAGNCNGA (SEQ ID NO:28, N=2NapdU; n=A, G, C or 2NapdU). These sequences had been selected in a special SELEX, where a competing toxin A aptamer (4943-51) was present in twofold excess over the target protein concentration.

TABLE 3

Affinities of Aptamer Clones from SELEX with *C. difficile* toxin A.

| Toxin A (TOXA_CLODI) Aptamer | | | Affinity to recombinant protein (SELEX Target) | | Affinity to mature protein (native target) | |
|---|---|---|---|---|---|---|
| Clone ID | Aptamer-ID | MOD | $K_d$ (nM) | Plateau | $K_d$ (nM) | Plateau |
| 247-8-1-1 | 4936-1_0 | TyrdU | 17.0 | 33% | | |
| 247-8-1-3 | 4936-3_0 | TyrdU | 23.9 | 27% | | |
| 247-8-1-4 | 4936-4_0 | TyrdU | 3.80 | 37% | 14.5 | 29% |
| 247-8-1-9 | 4936-9_0 | TyrdU | 33.3 | 11% | | |
| 247-8-1-13 | 4936-13_0 | TyrdU | 25.7 | 45% | | |
| 247-8-1-18 | 4936-18_0 | TyrdU | 74.5 | 36% | | |
| 247-8-1-32 | 4936-32_0 | TyrdU | 19.9 | 40% | | |
| 247-8-17-195 | 4939-195_0 | NapdU | 23.3 | 9% | >100 | 2% |
| 247-8-17-196 | 4939-196_0 | NapdU | 8.63 | 34% | 61.6 | 37% |
| 247-8-17-194 | 4939-194_0 | NapdU | 20.5 | 8% | | |
| 247-8-17-280 | 4939-280_0 | NapdU | 2.34 | 28% | 15.3 | 30% |
| 247-8-17-281 | 4939-281_0 | NapdU | 1.35 | 24% | >100 | 0% |
| 247-8-17-209 | 4939-209_0 | NapdU | 11.4 | 27% | 202 | 55% |
| 247-8-17-202 | 4939-202_0 | NapdU | 13.2 | 34% | 104 | 50% |
| 247-8-17-246 | 4939-246_0 | NapdU | 12.5 | 34% | 58.4 | 31% |
| 247-8-25-49 | 4943-49_0 | TrpdU | 1.39 | 49% | 7.91 | 43% |
| 247-8-25-50 | 4943-50_0 | TrpdU | 2.81 | 36% | 5.60 | 54% |
| 247-8-25-51 | 4943-51_0 | TrpdU | 1.23 | 43% | 1.78 | 54% |
| 247-8-25-60 | 4943-60_0 | TrpdU | 2.65 | 46% | 4.57 | 46% |
| 247-8-25-71 | 4943-71_0 | TrpdU | 6.26 | 18% | | |
| 247-8-25-73 | 4943-73_0 | TrpdU | 0.82 | 13% | | |
| 247-8-25-91 | 4943-91_0 | TrpdU | 0.43 | 10% | | |
| 270-8-1-49 | 5564-49_0 | 2NapdU | 1.13 | 30% | 1.78 | 11% |

TABLE 3-continued

Affinities of Aptamer Clones from SELEX with *C. difficile* toxin A.

| Toxin A (TOXA_CLODI) Aptamer | | | Affinity to recombinant protein (SELEX Target) | | Affinity to mature protein (native target) | |
|---|---|---|---|---|---|---|
| Clone ID | Aptamer-ID | MOD | $K_d$ (nM) | Plateau | $K_d$ (nM) | Plateau |
| 270-8-1-50 | 5564-50_0 | 2NapdU | 6.99 | 31% | >100 | 0% |
| 270-8-1-52 | 5564-52_0 | 2NapdU | 1.86 | 41% | 19.30 | 20% |
| 270-8-1-58 | 5564-58_0 | 2NapdU | 6.29 | 43% | 46.00 | 25% |
| 270-8-1-65 | 5564-65_0 | 2NapdU | 2.80 | 20% | >100 | 1% |
| 270-8-1-84 | 5564-84_0 | 2NapdU | 2.87 | 46% | >100 | 1% |
| 270-8-1-89 | 5564-89_0 | 2NapdU | 3.40 | 34% | 11.90 | 17% |
| 270-8-1-66 | 5564-66_0 | 2NapdU | 7.17 | 41% | >100 | 2% |
| 270-8-1-161 | 5564-161_0 | 2NapdU | 2.71 | 67% | 6.15 | 12% |
| 270-8-9-50 | 5570-50_0 | PEdU | 4.87 | 23% | >100 | 0% |
| 270-8-9-54 | 5570-54_0 | PEdU | 0.12 | 24% | 6.91 | 8% |
| 270-8-29-1 | 5577-1_0 | 2NapdU | 1.59 | 48% | 4.97 | 21% |
| 270-8-29-3 | 5577-3_0 | 2NapdU | 1.73 | 39% | 5.52 | 22% |
| 270-8-29-12 | 5577-12_0 | 2NapdU | 6.48 | 53% | 12.90 | 19% |

TABLE 4

*C. difficile* Toxin A Aptamer Clones. Lead sequences have their "Aptamer ID No." bolded and consensus sequences are underlined and appear under the label "Sequence Pattern". Base capital "N" represents the modified nucleotide as indicated for the particular pool (TyrdU, NapdU, TrpdU, 2NapdU, or PEdU). Base lower case "n" in the consensus sequence indicates a variable base within a motif which is selected from A, G, C or the modified nucleotide for the particular pool (TyrdU, NapdU, TrpdU, 2NapU, or PEdU).
IUPAC nucleotide ambiguity codes were used:
M = A or C; R = A or G; K = G or N (N representing the pool-specific modified dU), and a cut-off of 90% representation was used to define consensus.

| SEQ ID NO. | Aptamer ID No. | Count | Pct | |
|---|---|---|---|---|
| Clones from Pool 4936 (TyrdU) | | | | |
| 1 | 4936-4 | 8 | 20% | AANNCCNANCCNANNCANCACNNNCNNAGANNANNCNANG |
| Clones from Pool 4939 (NapdU) | | | | |
| 2 | 4939-196 | 5 | 3% | ACNNGNAGNAGCCCNNAANNGGGNNGCGNCGGCANNANGG |
| 3 | 4939-280 | 5 | 3% | ACNNGNAGNAGCCCNNAANNGGGNNGCGNCGGCANNANGG |
| 4 | 4939-246 | 5 | 3% | CNCGNNAGGGNNNANCCAANACCGNGGNGCCNNAACNAAA |
| Clones from Pool 4943 (TrpdU) | | | | |
| | | | | Sequence Pattern |
| 5 | | | | <u>NANAnnCNNNCnnCnN</u> |
| 6 | 4943-50 | 6 | 7% | AGCANNAAANNANAGACNNNCGNCANCGNCCCCCNNCGGN |
| 7 | 4943-60 | 6 | 7% | ANCNCNCACANNANAGACNNNCNNCANGGNCCNCCNGAGA |
| 8 | 4943-49 | 4 | 5% | NGCCNAAACCNANAACCNNNNCCACGNGNACNN |
| 9 | 4943-51 | 15 | 19% | GNANANCAACNCGNCANGGNAGCGNAANNCNAGCNNAGA |
| Clones from Pool 5564 (2NapdU) | | | | |
| 10 | 5564-49 | 6 | 7% | CCNGACGGGCGAGGNNCCAACNNACNNCCGNCACNANNGC |
| | | | | Sequence Pattern |
| 11 | | | | <u>NAAAGNAGGN</u> |
| 12 | 5564-52 | 15 | 17% | CGCANGNGNNCNGANACACNGGCCNAAAGNAGGNCNGNAG |
| 13 | 5564-57 | 1 | 1% | CCGNNCNAANACCAANGGANAAAGNAGGNAGGAGCNCGCA |
| 14 | 5564-82 | 1 | 1% | NACCAGANAGNNANAANACGCNGGCNAAAGNAGGNACNAA |
| | | | | Sequence Pattern |
| 15 | | | | <u>GNNRNCMKNCNGA</u> |
| 16 | 5564-89 | 2 | 2% | CNAAANGAAGNNGNCAGNCNGACGCCAGNGCGNACCGN |
| 17 | 5564-54 | 1 | 1% | NGCGNACCCGCNGNNGNCAGNCNGAGAGANCGGCNAAGAA |
| 18 | 5564-59 | 1 | 1% | CNAGCGNCANACCCCACGNNGNCAGNCNGAGCGCCCACN |
| 19 | 5564-164 | 1 | 1% | NGCCNGCCCACCNGNNGNCAGNCNGAGAGCNANCCAAACA |
| 20 | 5564-167 | 1 | 1% | CANGCCNGCANACCACACGNNGNNAGNCNGAGGGNNAGG |
| 21 | 5564-67 | 4 | 5% | GGNACCNACCCGCAGNGNNANCANNCNGACCGCGACNNNN |
| 22 | 5564-58 | 4 | 5% | CNGNNANCCGNCNGACACCNACCNACCGGAGNAAGANCC |

TABLE 4-continued

C. difficile Toxin A Aptamer Clones. Lead sequences have their
"Aptamer ID No." bolded and consensus sequences are underlined and appear
under the label "Sequence Pattern". Base capital "N" represents the
modified nucleotide as indicated for the particular pool (TyrdU, NapdU, TrpdU, 2NapdU,
or PEdU). Base lower case "n" in the consensus sequence indicates a variable
base within a motif which is selected from A, G, C or the modified nucleotide for
the particular pool (TyrdU, NapdU, TrpdU, 2NapU, or PEdU).
IUPAC nucleotide ambiguity codes were used:
M = A or C; R = A or G; K = G or N (N representing the pool-specific
modified dU), and a cut-off of 90% representation was used to define consensus.

| SEQ ID NO. | Aptamer ID No. | Count | Pct | |
|---|---|---|---|---|
| | | | | Sequence Pattern |
| 23 | | | | CGGGNCGNGACAGANCGCA |
| 24 | 5564-161 | 4 | 5% | CGAGCGGGNCGNGACAGANCGCAGAGCGAAGGCNNANCNAC |
| 25 | 5564-152 | 2 | 2% | NCNGANGGGCCAACAAANGNCCGGGNCGNGACAGANCGCA |
| | | | | Clones from Pool 5570 (PEdU) |
| 26 | 5570-54 | 10 | 23% | GCNGAGGCCGNGCNCANNAANNGAACNNAGAANANCCCNA |
| | | | | Clones from Pool 5577 (2NapdU) |
| 27 | 5577-1 | 4 | 9% | ACCGCNAAAGNAGGNCACGNNCNAANACCCNGGGAGGNGN |
| | | | | Sequence Pattern |
| 28 | | | | NACCGAACGNNnNCAGNCNGA |
| 29 | 5577-3 | 3 | 7% | GCNGCCNACCGAACGNNGNCAGNCNGAGCGANCGAACNNG |
| 30 | 5577-12 | 3 | 7% | AGCCACGNACANACCGAACGNNANCAGNCNGACGCNGNGA |
| 31 | 5577-16 | 1 | 2% | CCGNGCANACCCCCNGNNGNCAGNCNGACGGCCAGACAC |

Example 4

Toxin B Aptamer Clones

The affinities of aptamers for toxin B were generally very good and correlated well between the 68.8 kDa amino-terminal catalytic domain of *C. difficile* toxin B fragment that had been used in SELEX and the 270 kDa native, full-length toxin B. Aptamer clones with sub-nanomolar $K_d$'s for toxin B were isolated from all of the pools with TyrdU, BndU, NapdU, TrpdU, 2NapdU and PEdU modified nucleotides (Table 5); the sequences of *C. difficile* toxin B aptamers are listed in Table 6, with the best clones shown in bold.

Clones from Pool 4937 (TyrdU): Alignments of the TyrdU aptamers indicated the presence of two distinct sequence patterns (YNNSSNGAAW (SEQ ID NO: 32), YGAAWN (SEQ ID NO: 47)), (N=TyrdU; W=A or N; S=C or G; Y=C or N), as well as one orphan sequence.

Clones from Pool 4938 (BndU): This pool contained three unrelated sequences, all were present in multiple copies.

Clones from Pool 4940 (NapdU): The most abundant sequences, including four of the leading clones, contained all or part of the pattern KSGANNGGRW (SEQ ID NO: 66) (N=NapdU; R=A or G; W=A or N; S=C or G; K=G or N). In addition, three unrelated orphan sequences were present.

Clones from Pool 4944 (TrpdU): The majority of the sequences contained the pattern NnCYnnnNCNNnAARN-MAMSYN (SEQ ID NO: 75); two other sequences shared a different pattern, CNnGnANCNGGAAAN, (SEQ ID NO:83, N=TrpdU; n=A, G, C or TrpdU; M=A or C; R=A or G; W=A or N; S=C or G; Y=C or N), and four orphan sequences were also present.

Clones from Pool 5566 (2NapdU): Pattern AnCnNNNAAGNGAACNNN-nAnnnnnnnnnGnGNNnANA (SEQ ID NO:90, N=2NapdU; n=A, G, C or 2NapdU) was found in a couple of clones. This pool contained two additional unrelated sequences in multiple copies.

Clones from Pool 5573 (PEdU): Two patterns were identified, GCCNNNCNNGNNAAACGNCCNNGANG-GCAGCGNN (SEQ ID NO:95) and (SEQ ID NO:98, N=PEdU). Six additional, unrelated clones were present.

Clones from Pool 5578 (NapdU): Two active clones were present in multiple copies. These sequences had been selected in a special SELEX, where a competing toxin B aptamer (4940-23) was present in twofold excess over the target protein concentration.

The highest-affinity aptamers were clones with NapdU or TrpdU modified nucleotides. Five aptamers demonstrated very low $K_d$'s of <0.1 nM for native toxin B.

TABLE 5

Affinities of Aptamer Clones from SELEX with *C. difficile* toxin B.

| Toxin B (TOXB_CLODI) Aptamer | | | Affinity to recombinant protein (SELEX Target) | | Affinity to mature protein (native target) | |
|---|---|---|---|---|---|---|
| Clone ID | Aptamer-ID | MOD | $K_d$ (nM) | Plateau | $K_d$ (nM) | Plateau |
| 247-8-3-49 | 4937-49_0 | TyrdU | 0.19 | 23% | 0.16 | 6% |
| 247-8-3-50 | 4937-50_0 | TyrdU | 0.36 | 26% | 0.27 | 4% |
| 247-8-3-51 | 4937-51_0 | TyrdU | 0.60 | 31% | 1.07 | 14% |

TABLE 5-continued

Affinities of Aptamer Clones from SELEX with *C. difficile* toxin B.

| Toxin B (TOXB_CLODI) Aptamer | | | Affinity to recombinant protein (SELEX Target) | | Affinity to mature protein (native target) | |
|---|---|---|---|---|---|---|
| Clone ID | Aptamer-ID | MOD | $K_d$ (nM) | Plateau | $K_d$ (nM) | Plateau |
| 247-8-3-55 | 4937-55_0 | TyrdU | 0.15 | 39% | 0.15 | 15% |
| 247-8-3-57 | 4937-57_0 | TyrdU | 0.15 | 35% | 0.12 | 11% |
| 247-8-3-66 | 4937-66_0 | TyrdU | 0.63 | 34% | 0.59 | 14% |
| 247-8-3-67 | 4937-67_0 | TyrdU | 0.11 | 21% | 0.23 | 16% |
| 247-8-3-81 | 4937-81_0 | TyrdU | 0.23 | 19% | 0.28 | 13% |
| 247-8-3-85 | 4937-85_0 | TyrdU | 0.27 | 32% | 0.72 | 25% |
| 247-8-3-94 | 4937-94_0 | TyrdU | 0.27 | 27% | 0.36 | 12% |
| 247-8-11-1 | 4938-1_0 | BndU | 0.84 | 23% | 2.03 | 20% |
| 247-8-11-6 | 4938-6_0 | BndU | 1.02 | 16% | 1.52 | 17% |
| 247-8-11-17 | 4938-17_0 | BndU | 0.36 | 32% | 0.50 | 16% |
| 247-8-19-1 | 4940-1_0 | NapdU | 0.04 | 24% | 0.06 | 14% |
| 247-8-19-3 | 4940-3_0 | NapdU | 1.04 | 27% | 0.67 | 12% |
| 247-8-19-6 | 4940-6_0 | NapdU | 0.05 | 15% | 0.43 | 7% |
| 247-8-19-8 | 4940-8_0 | NapdU | 0.19 | 33% | 0.27 | 10% |
| 247-8-19-19 | 4940-19_0 | NapdU | 0.11 | 23% | 0.14 | 8% |
| 247-8-19-23 | 4940-23_0 | NapdU | 0.07 | 37% | 0.09 | 13% |
| 247-8-19-27 | 4940-27_0 | NapdU | 0.10 | 34% | 0.09 | 12% |
| 247-8-27-1 | 4944-1_0 | TrpdU | 0.20 | 26% | 0.13 | 10% |
| 247-8-27-4 | 4944-4_0 | TrpdU | 0.10 | 29% | 0.16 | 11% |
| 247-8-27-5 | 4944-5_0 | TrpdU | 0.08 | 33% | 0.09 | 10% |
| 247-8-27-9 | 4944-9_0 | TrpdU | 0.18 | 36% | 0.14 | 9% |
| 247-8-27-11 | 4944-11_0 | TrpdU | 0.14 | 24% | 0.22 | 6% |
| 247-8-27-14 | 4944-14_0 | TrpdU | 0.24 | 20% | 0.70 | 9% |
| 247-8-27-20 | 4944-20_0 | TrpdU | 0.12 | 25% | 0.18 | 7% |
| 247-8-27-30 | 4944-30_0 | TrpdU | 0.06 | 28% | 0.08 | 9% |
| 247-8-27-34 | 4944-34_0 | TrpdU | 0.07 | 35% | 0.41 | 10% |
| 270-8-5-53 | 5566-53_0 | 2NapdU | 0.02 | 5% | 0.22 | 15% |
| 270-8-5-74 | 5566-74_0 | 2NapdU | 0.04 | 6% | 0.25 | 21% |
| 270-8-5-77 | 5566-77_0 | 2NapdU | NT | NT | 0.23 | 6% |
| 270-8-13-2 | 5573-2_0 | PEdU | 0.03 | 33% | 0.11 | 15% |
| 270-8-13-3 | 5573-3_0 | PEdU | 0.04 | 52% | 0.25 | 12% |
| 270-8-13-4 | 5573-4_0 | PEdU | 0.03 | 54% | 0.08 | 12% |
| 270-8-13-5 | 5573-5_0 | PEdU | 0.06 | 49% | 0.55 | 14% |
| 270-8-13-9 | 5573-9_0 | PEdU | 0.01 | 45% | 0.14 | 13% |
| 270-8-13-11 | 5573-11_0 | PEdU | 6.82 | 36% | 2.70 | 8% |
| 270-8-13-14 | 5573-14_0 | PEdU | 0.04 | 21% | 0.33 | 9% |
| 270-8-13-23 | 5573-23_0 | PEdU | 1.49 | 35% | 0.55 | 9% |
| 270-8-13-24 | 5573-24_0 | PEdU | 0.02 | 33% | 0.11 | 10% |
| 270-8-30-66 | 5578-66_0 | 2NapdU | 0.98 | 14% | NT | NT |
| 270-8-30-73 | 5578-73_0 | 2NapdU | 1.62 | 18% | NT | NT |

TABLE 6

*C. difficile* Toxin B Aptamer Clones. Lead sequences have their "Aptamer ID No." bolded and consensus sequences are underlined and appear under the label "Sequence Pattern". Base capital "N" represents the modified nucleotide as indicated for the particular pool (TyrdU, BndU, NapdU, TrpdU, 2NapdU, or PEdU). Base lower case "n" in the consensus sequence indicates a variable base within a motif which is selected from A, G, C or the modified nucleotide for the particular pool (TyrdU, NapdU, TrpdU, 2NapdU, or PEdU). IUPAC nucleotide ambiguity codes were used: M = A or C; R = A or G; W = A or N; S = C or G; Y = C or N; K = G or N (N representing the pool-specific modified dU), and a cut-off of 90% representation was used to define consensus.

| SEQ ID NO. | Aptamer IN No. | Count | Pct | Sequence Pattern |
|---|---|---|---|---|
| | | | | Clones from Pool 4937 (TyrdU) |
| 32 | | | | YNNSSNGAAW |
| 33 | 4937-50 | 6 | 8% | NANNNCCNNAAGGCNNGGNGAAAACCGCNNNNCGGNNGCG |
| 34 | 4937-51 | 3 | 4% | NGGACCACNANCCCNCCCCACNNNNNCGNGAACNNGAGNN |
| 35 | 4937-53 | 2 | 3% | NGGANCACGNANNCCCACNNACCNNCCNGAAAANAGCANNN |
| 36 | 4937-54 | 4 | 5% | ACNNGGNGAAANNCACNNNNCNGCCAGCANCNANNCCCGCN |
| 37 | 4937-56 | 2 | 3% | NNGGCACGAAGNANNGACNNNGAAANNGCNGAAACANCNNNNNCN |
| 38 | 4937-57 | 5 | 6% | NGGACACCNANNACAGNCNNCGNGAAANNGCANNN |
| 39 | 4937-61 | 2 | 3% | GNGCNGCCNANCNANCCNCNCNNANGAANCCGAANNCC |
| 40 | 4937-63 | 2 | 3% | NCCANNCCACCGCGGNGCCACAGNANCANGNNNGCNGAAN |
| 41 | 4937-74 | 2 | 3% | NCCNANCCNCNCNNCGNGAANCCGAANNGCCNACNGCCNN |

TABLE 6-continued

*C. difficile* Toxin B Aptamer Clones. Lead sequences have their "Aptamer ID No."
bolded and consensus sequences are under TABLE 6-continued C. difficile Toxin B Aptamer Clones. Lead sequences have their "Aptamer ID No."
bolded and consensus sequences are underlined and appear under the label
"Sequence Pattern". Base capital "N" represents the modified nucleotide as
indicated for the particular pool (TyrdU, BndU, NapdU, TrpdU, 2NapdU, or PEdU).
Base lower case "n" in the consensus sequence indicates a variable base within
a motif which is selected from A, G, C or the modified nucleotide for the
particular pool (TyrdU, NapdU, TrpdU, 2NapdU, or PEdU). IUPAC nucleotide ambiguity
codes were used: M = A or C; R = A or G; W = A or N; S = C or G;
Y = C or N; K = G or N (N representing the pool-specific modified dU),
and a cut-off of 90% representation was used to define consensus.

| SEQ ID NO. | Aptamer IN No. | Count | Pct | |
|---|---|---|---|---|
| | | | | Clones from Pool 5566 (2NapdU) |
| | | | | Sequence Pattern |
| 90 | | | | AnCnNNNAAGNGAACNNNnAnnnnnnnnnGnGNNnANA |
| 91 | 5566-53 | 3 | 7% | CCAGCANNNAAGNGAACNNNAAGGAAGGGAGGAGNNCANA |
| 92 | 5566-90 | 1 | 2% | AGACCGNNNAAGNGAACNNNCAACGGGANGCGNGNNAANA |
| 93 | 5566-74 | 4 | 9% | AGNGGCGNNAANGCANNNAACGAGCACNGAGGCGNNAANA |
| 94 | 5566-77 | 3 | 7% | CNNNNNNACCGCNGCANGACNNNAGCGGCAGNCGNGNGNG |
| | | | | Clones from Pool 4473 (PEdU) |
| | | | | Sequence Pattern |
| 95 | | | | GCCNNNCNNGNNAAACGNCCNNGANGGCAGCGNN |
| 96 | 5573-23 | 2 | 5% | GAACGN GCCNNNCNNGNNAAACGNCCNNGANGGCAGCGNN |
| 97 | 5573-25 | 1 | 2% | AACNCG GCCNNNCNNGNNAAACGNCCNNGANGGCAGCGNN |
| | | | | Sequence Pattern |
| 98 | | | | AGNNNGANCCC |
| 99 | 5573-3 | 7 | 16% | NACGGCANNCNGGNGGCAAGNNNGANCCCNCCGAGCCNAN |
| 100 | 5573-5 | 2 | 5% | CGANCACANCGCACANNAGNCAGNNNGANCCCANNAANCA |
| 101 | 5573-2 | 14 | 32% | NCAGGNNANACCCAGNGNAGGAAAACGNGNACGNNCCGAN |
| 102 | 5573-4 | 8 | 18% | AANNNANGNGANCAANNGAGCAGACCGCCANNNGACNNCG |
| 103 | 5573-14 | 3 | 7% | GGNGGNGGAAANNGGCAAGNGNANGGNGGNNACGCCGNAN |
| 104 | 5573-24 | 2 | 5% | NGCGNCNGANCCGNAAAACCANNNCAAGCNACCANGNNNA |
| 105 | 5573-9 | 2 | 5% | CGCCGNNNCCGNCCGGCCACAANNNAAGNACAANNGGAN |
| 106 | 5573-11 | 2 | 5% | NGNCCGCCGACCANNNNCNGNANAGCCNCNNGNAANNAGN |
| | | | | Clones from Pool 5578 (2NapdU) |
| 107 | 5578-66 | 3 | 7% | GAAAGCNNCGNACGNAGNNGNGAGAGGNCNCNGCCCNCNN |
| 108 | 5578-73 | 4 | 9% | ANNAAGCNNGNGGCNGGNAGCNGACAGCCAGGGANNCNGA |

Example 5

Binary Toxin (A Chain) Aptamer Clones

SELEX with the recombinant binary toxin A chain (CdtA) yielded active aptamers with TrpdU, 2NapdU, and PEdU modified nucleotides (Table 7).

The sequences and common sequence patterns of CdtA aptamers are shown in Table 8.

Cloning of pool 4758 (TrpdU) revealed clone 4758-6 which comprised 18% of the sequences in that pool and showed good affinity ($K_d$=0.86 nM) to CdtA binary toxin.

Twenty sequences from 2NapdU pools were obtained, most of them with subnanomolar affinity, and several sequence patterns shared between these 2NapdU clones were identified: GAANANnNCCGNGAnGNAANGnnANANNS (SEQ ID NO: 110), ANNRGCNnCCNGGCS (SEQ ID NO: 124), WAWNNANNA (SEQ ID NO: 125), and GGANNG-CAGGNNCMC (SEQ ID NO: 134) (N=PEdU; n=A, G, C or PEdU; M=A or C; W=A or N; S=C or G; R=A or G).

PEdU pools contained five active aptamers; they were present in multiple copies, and three of the sequences shared the pattern NAAAWGNNN (SEQ ID NO: 145) (N=PEdU; W=A or N).

TABLE 7

Affinities of Aptamer Clones from SELEX with
C. difficile binary toxin A chain.

| Binary Toxin A Chain (CdtA_CLODI) Aptamer | | | Affinity to recombinant CdtA protein (SELEX Target) | |
|---|---|---|---|---|
| Clone ID | Seq-ID | MOD | $K_d$ (nM) | Plateau |
| 239-7-39-6 | 4758-6_0 | TrpdU | 0.86 | 18% |
| 261-8-24-49 | 5551-49_0 | 2NapdU | 0.31 | 9% |
| 261-8-24-50 | 5551-50_0 | 2NapdU | 0.09 | 30% |
| 261-8-24-52 | 5551-52_0 | 2NapdU | 0.14 | 26% |
| 261-8-24-60 | 5551-60_0 | 2NapdU | 5.79 | 60% |
| 261-8-24-81 | 5551-81_0 | 2NapdU | 0.54 | 32% |
| 261-8-32-6 | 5555-6_0 | PEdU | 0.62 | 21% |
| 261-8-32-15 | 5555-15_0 | PEdU | 1.72 | 18% |
| 261-8-32-39 | 5555-39_0 | PEdU | 0.34 | 12% |
| 270-8-6-1 | 5567-1_0 | 2NapdU | 0.15 | 24% |
| 270-8-6-2 | 5567-2_0 | 2NapdU | 6.81 | 25% |
| 270-8-6-10 | 5567-10_0 | 2NapdU | 0.03 | 17% |
| 270-8-6-13 | 5567-13_0 | 2NapdU | 0.03 | 22% |
| 270-8-6-18 | 5567-18_0 | 2NapdU | 0.16 | 10% |
| 270-8-6-34 | 5567-34_0 | 2NapdU | 0.09 | 14% |
| 270-8-6-46 | 5567-46_0 | 2NapdU | 0.05 | 12% |
| 270-8-14-49 | 5574-49_0 | PEdU | 0.16 | 57% |
| 270-8-14-56 | 5574-56_0 | PEdU | 2.92 | 55% |
| 270-8-31-5 | 5579-5_0 | 2NapdU | 2.24 | 13% |
| 270-8-31-7 | 5579-7_0 | 2NapdU | 2.44 | 44% |
| 270-8-31-8 | 5579-8_0 | 2NapdU | 0.53 | 41% |

TABLE 7-continued

Affinities of Aptamer Clones from SELEX with C. difficile binary toxin A chain.

| Binary Toxin A Chain (CdtA_CLODI) Aptamer | | | Affinity to recombinant CdtA protein (SELEX Target) | |
|---|---|---|---|---|
| Clone ID | Seq-ID | MOD | $K_d$ (nM) | Plateau |
| 270-8-31-10 | 5579-10_0 | 2NapdU | 0.15 | 36% |
| 270-8-31-11 | 5579-11_0 | 2NapdU | 0.07 | 33% |
| 270-8-31-12 | 5579-12_0 | 2NapdU | 0.97 | 53% |
| 270-8-31-21 | 5579-21_0 | 2NapdU | 0.24 | 35% |

TABLE 8

C. difficile Binary Toxin A Chain Aptamer Clones. Lead sequences have their "Aptamer ID No." bolded and consensus sequences are underlined and appear under the label "Sequence Pattern". Base capital "N" represents the modified nucleotide as indicated for the particular pool (TrpdU, 2NapdU, or PEdU). Base lower case "n" in the consensus sequence indicates a variable base within a motif which is selected from A, G, C or the modified base within nucleotide for the particular pool (TrpdU, 2NapdU, or PEdU). IUPAC nucleotide ambiguity codes were used: M = A or C; R = A or G; W = A or N; S = C or G; (N representing the pool-specific modified dU), and a cut-off of 90% representation was used to define consensus.

| SEQ ID NO. | Aptamer ID No. | Count | Pct | Sequence |
|---|---|---|---|---|
| Clones from Pool 4758 (TrpdU) | | | | |
| 109 | 4758-6 | 8 | 18% | GAAGACTTTAATTCTGACATGGTGTCCAATGGCGCGCGAG |
| Clones from Pool 5551, 5567, 5579 (2NapdU) | | | | |
| | | | | Sequence Pattern |
| 110 | | | | <u>GAANANnNCCGNGAnGNAANGnnANANNS</u> |
| 111 | 5567-30 | 1 | 1% | GAANCNGNCCGNGACGNAANG AANANNC |
| 112 | 5579-21 | 5 | 4% | GAANCNGNCCGNGACGNAANGCCANANNCGGAGGGGAN |
| 113 | 5579-28 | 1 | 1% | GAANCNGNCCGNGAAGNAANGCCANANNCGCANG |
| 114 | 5567-1 | 11 | 9% | GAANANGNCCGNGAAGNAANGCGANANNC |
| 115 | 5567-41 | 1 | 1% | GAANANGNCCGNGAAGNAANGGCANANNCGNCCACGNGGG |
| 116 | 5551-77 | 1 | 1% | CGGGNCACCGCANNCNCCGNGACGNAANGACANANNCGGN |
| 117 | 5551-60 | 2 | 2% | AACCCCGCGGCAANNANCCGNGAAGNAANG AANANNCCGA |
| 118 | 5579-48 | 1 | 1% | ACAGAGGCANNCNCCGNGANGNAANGCAANANNCCGCCGN |
| 119 | 5567-2 | 4 | 3% | NGCAACNANCCGNGANGNAANGCAANANNGCAACANGNGC |
| 120 | 5567-26 | 1 | 1% | GGACNACNCNCCGNGANGNAANGCGAAANNCCCAGANGNA |
| 121 | 5551-81 | 4 | 3% | NCGAANGANAACANGNAACNCCGNGANNACANCGAANAGN |
| 122 | 5579-7 | 7 | 6% | CNAAGCNCCGAGGCNNACNCCGNGANCGCANGGNNNAACC |
| 123 | 5579-12 | 4 | 9% | NCGAGCAACGAGNAACNCCGNGANNACAANCGANAGANGA |
| | | | | Sequence Pattern |
| 124,125 | | | | <u>ANNRGCN CCNGGCS WAWNNANNA</u> |
| 126 | 5579-11 | 10 | 11% | NNGCNACCCAANNAGCN CCNGGCGG GNNAANNANNAGACA |
| 127 | 5551-64 | 1 | 1% | CANCCAANNAGCNCCCNGGCGA NGNAANNANNANGGCACN |
| 128 | 5551-78 | 1 | 1% | NCGNANACCGAANNAGCNCGCCNGGCGA CCNAANNANNACA |
| 129 | 5551-50 | 2 | 2% | CCNGCCNCANNAGCN CCNGGCGCCCNNAANNANNAAAACN |
| 130 | 5579-45 | 1 | 1% | GACCNCANCANNGGCN CCNGGCCG GNNAANNANNACCACC |
| 131 | 5567-13 | 3 | 2% | NAGAGAAANNGGCNGCGNGGCCACCCNAANNANNAGAGCA |
| 132 | 5567-34 | 3 | 2% | CNCAAGGCNANNGGCN GCNGGCAGA NNAANNANNAAAGNC |
| 133 | 5567-10 | 8 | 6% | ANNGGCN CCNGGCCGGANAANNNANNACCCAGNGAGNGAA |
| Clones from Pools 5551, 5567, 5579 (2NapdU) | | | | |
| | | | | Sequence Pattern |
| 134 | | | | <u>GGANNGCAGGNNCMC</u> |
| 135 | 5579-10 | 2 | 2% | NAGNCACGGNGAACNGGANNGCAGGNNCCCCCCNGGCNA |
| 136 | 5551-52 | 13 | 15% | GGNCAGCNGGANNGCAGGNNCCCCCCNGANAGGACGGNNN |
| 137 | 5551-59 | 2 | 2% | GNAGNCGGANNGCAGGNNCCCACCAAACACCNNNGGNAGA |
| 138 | 5567-46 | 2 | 2% | CNGGAGACNGGNCAGAACAGCCGGGANNGCAGGNNCACGG |
| | | | | Sequence Pattern |
| 139 | | | | <u>GAANNGNNCCG</u> |
| 140 | 5579-5 | 3 | 3% | GNNGAANNGNNCCGCCGCCNNNCNGNCCGCGGGNNGCNGN |
| 141 | 5579-34 | 1 | 1% | NGCNCAGAANNGNNCCGANAGGGNNGCNGCCACNGANAN |
| 142 | 5551-49 | 5 | 6% | GCCNNNNGGCGAGGNGAGNNNNCCCAGNCNGANGAAGCNN |

TABLE 8-continued

C. difficile Binary Toxin A Chain Aptamer Clones. Lead sequences have their
"Aptamer ID No." bolded and consensus sequences are underlined and appear
under the label "Sequence Pattern". Base capital "N" represents the
modified nucleotide as indicated for the particular pool (TrpdU, 2NapdU,
or PEdU). Base lower case "n" in the consensus sequence indicates a variable base
within a motif which is selected from A, G, C or the modified base within nucleotide
for the particular pool (TrpdU, 2NapdU, or PEdU). IUPAC nucleotide ambiguity codes
were used: M = A or C; R = A or G; W = A or N; S = C or G; (N representing the pool-
specific modified dU), and a cut-off of 90% representation was used to define consensus.

| SEQ ID NO. | Aptamer ID No. | Count | Pct | |
|---|---|---|---|---|
| 143 | 5579-8 | 5 | 6% | CGGAGCCCGAAGGNNAAGCGGNNCACCANNANACGANACG |
| 144 | 5567-18 | 2 | 2% | CNCCGNANNGCGNCCNGGGCAGNNAANCNANNAGAAGCCA |

Clones from Pools 5555, 5574 (PEdU)

| | | | | Sequence Pattern |
|---|---|---|---|---|
| 145 | | | | NAAAWGNNN |
| 146 | 5555-6 | 9 | 14% | GNGNGNCAGCGCANNANACGCGNAANNAAANGNNNAGAGA |
| 147 | 5555-15 | 8 | 12% | GCGNGNCNGNANNAAAAGNNNGCGGAGGGGNNCCCGGNAC |
| 148 | 5574-49 | 13 | 20% | NNNCGAGAANAAANGNNNGANACANNACNNANAANANGGN |
| 149 | 5555-39 | 3 | 5% | AGCCGGNGNGNGNANNAACNCNNNCGGCNNNCCNCCCGCA |
| 150 | 5574-56 | 11 | 17% | CNNGNGNAAACCGNGCGNNAGNANNGGAGANAGCNGACAN |

Example 6

Binary Toxin (B Chain) Aptamer Clones

SELEX with recombinant binary toxin B chain (CdtB) yielded active aptamers with 2NapdU modified nucleotides (Table 9). The sequences and common sequence patterns of CdtB aptamers are shown in Table 10. The most active clone, 5556-51, contained all of these patterns, NNARASCS (SEQ ID NO: 151), NNNGGCNNNACG (SEQ ID NO: 152), and AGCCNNNGRCNN (SEQ ID NO: 157) (N=2NapdU; R=A or G; S=C or G), some of which were present in other sequences. Three additional clones had unrelated sequences.

TABLE 9

Affinities of Aptamer Clones from SELEX with C. difficile binary toxin B chain.

| Binary Toxin B Chain (CdtA_CLODI) Aptamer | | | Affinity to recombinant CdtB protein (SELEX Target) | |
|---|---|---|---|---|
| Clone ID | Seq-ID | MOD | $K_d$ (nM) | Plateau |
| 261-8-33-51 | 5556-51_0 | 2NapdU | 1.68 | 38% |
| 261-8-33-57 | 5556-57_0 | 2NapdU | 11.60 | 37% |
| 261-8-33-60 | 5556-60_0 | 2NapdU | 12.30 | 48% |
| 261-8-33-67 | 5556-67_0 | 2NapdU | 2.16 | 45% |
| 261-8-33-83 | 5556-83_0 | 2NapdU | 7.62 | 33% |

TABLE 10

C. difficile Binary Toxin B Chain Aptamer Clones. Lead sequences have their
"Aptamer ID No." bolded and consensus sequences are underlined and appear
under the label "Sequence Pattern". Base capital "N" represents 2NapdU. IUPAC
nucleotide ambiguity codes were used: R = A or G; S = C or G; and a cut-off
of 90% representation was used to define consensus.
Clones from Pool 5556 (2NapdU)

| SEQ ID NO. | Aptamer ID No. | Count | Pct | Sequence Pattern |
|---|---|---|---|---|
| 151 | | | | NNARASCS |
| 152 | | | | NNNGGCNNNACG |
| 153 | 5556-51 | 5 | 15% | AAGNNAAACCGAGACGCGGCCGGAAGCCNNNGGCNNNACG |
| 154 | 5556-87 | 1 | 3% | GNNAAACCCCGGGGGGCCAAGCGCANNNGGCNNNACGAA |
| 155 | 5556-94 | 1 | 3% | CAACGNNAANNAGAGCCNNNGNCCNAACAAANNACGCANG |
| 156 | 5556-69 | 1 | 3% | AANCGGAGCCCNNANAACCCNNAAACCCNNNANACCAANN |
| | | | | |
| 157 | | | | AGCCNNNGRCNN |
| 158 | 5556-51 | 5 | 15% | AAGNNAAACCGAGACGCGGCCGGAAGCCNNNGGCNNNACG |
| 159 | 5556-60 | 1 | 3% | GNNAANNAGAGCCNNNGACNNGAACAGGNNCACGCANNAC |
| 160 | 5556-57 | 4 | 12% | CNNGACNGNACCNNNNNCGACACAGAACAGCAAGACCNNC |
| 161 | 5556-67 | 2 | 6% | GGACCGANGAANCNAGCNNGNNAANAGCGNNGAGCNANCC |
| 162 | 5556-83 | 2 | 6% | CACNNAGCAACCGACACAAGNNGNNCCGNNANCCGNNANA |

Example 7

Use of Aptamers for Toxin A/B and Binary Toxin as Diagnostic Reagents: Pull-Down Assays Aptamers were used to specifically pull-down their respective targets, toxin A, toxin B, or binary toxin, from spiked samples, thus affinity purification of these proteins is achieved, as needed.

In this assay, biotinylated aptamers were immobilized on MyOne streptavidin beads and mixed with their targets for 1 h to allow binding. The beads were then washed, and captured target was tagged with NHS-Alexa-647. After extensive washing, the captured targets were eluted with 20 mM NaOH, neutralized, analyzed by SDS-PAGE, and proteins were visualized using the cy5 channel.

Figure 2A:
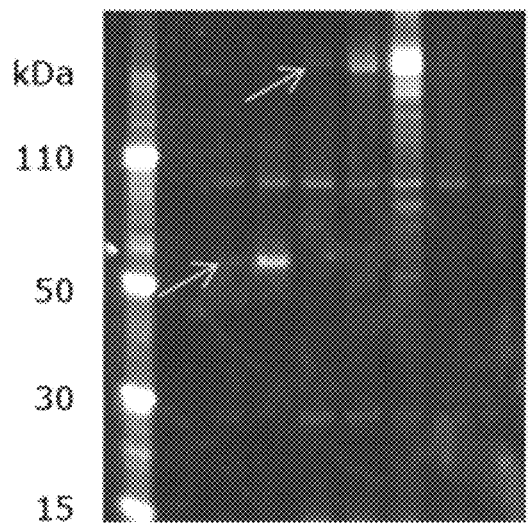
FIG. 2A illustrates the results of a pull-down assay of recombinant and native toxin A using toxin A aptamers showing high specificity over the control proteins toxin B or BSA.
Figure 2B:
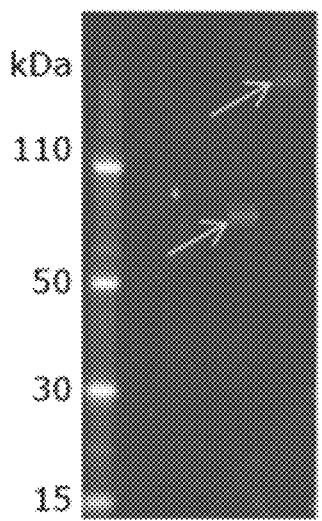
FIG. 2B illustrates the results of a pull-down assay of recombinant and native toxin B using toxin B aptamers showing high specificity over the control proteins recombinant and native toxin A.

FIG. 2 illustrates the following pull down assay results: the toxin A aptamer pulled down toxin A (recombinant or native) with good specificity over the control proteins toxin B or BSA; the toxin B aptamer pulled down toxin B (recombinant or native), but not toxin A; the aptamer for binary toxin A subunit pulled down CdtA, but not CdtB; and no proteins were present in the pull-down fraction when a random aptamer was used.

Example 8

Use of Aptamers for Toxin A/B and Binary Toxin as Diagnostic Reagents: Dot Blot Assays Aptamers were used for the detection of toxins in dot blot assays, e.g. using biotinylated aptamers and a signal amplifying enzyme such as alkaline phosphatase (AP) or horseradish peroxidase (HRP).

Figures 3A, 3B:
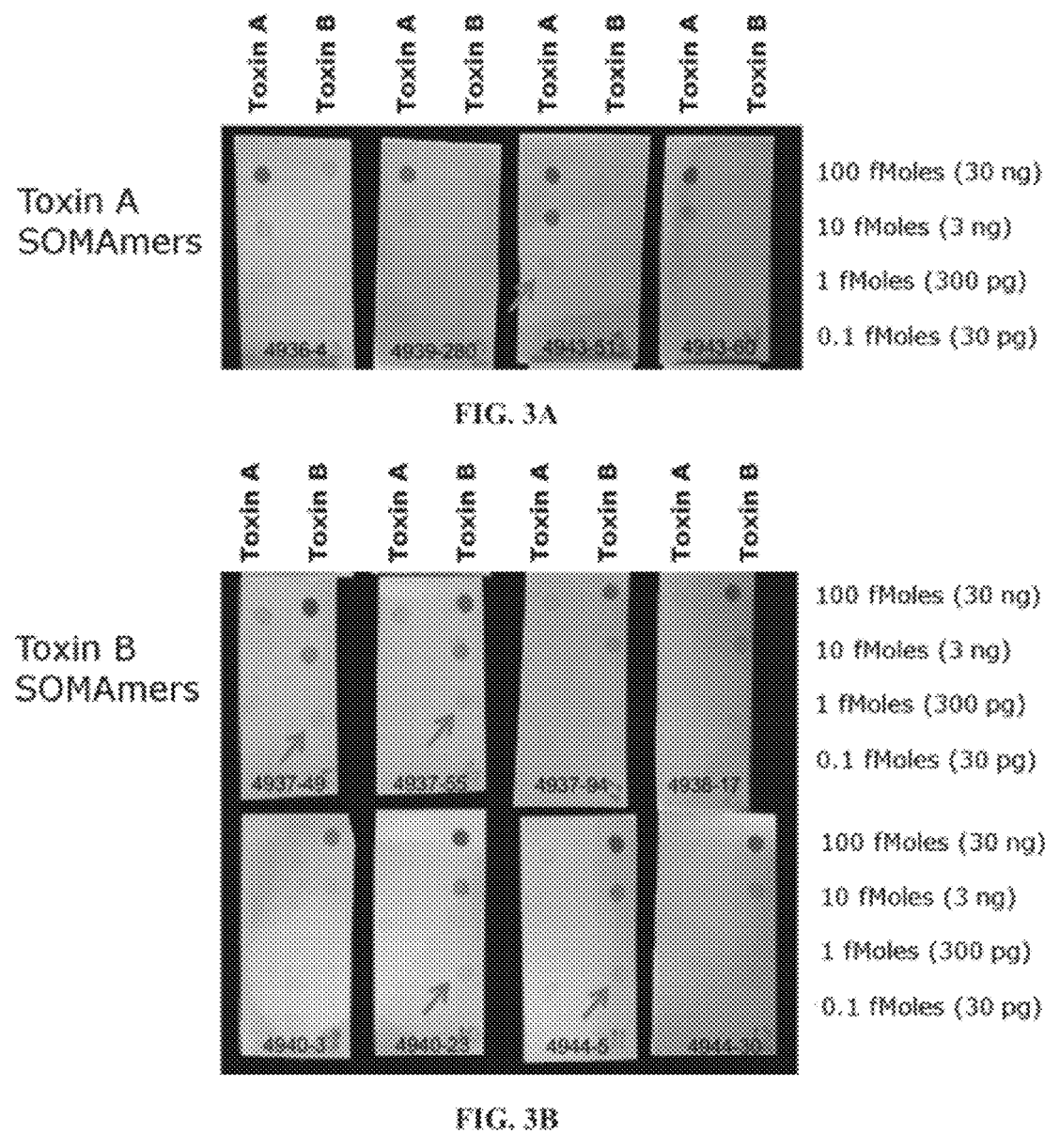

Toxin detection was demonstrated in simple dot blots of toxin A and B (FIGS. 3A and 3B). In this assay, 1 μL of serially diluted target was spotted and air-dried onto nitrocellulose membranes. After blocking, individual biotinylated aptamers were added (1 nM), followed by SA-AP conjugate (200 ng/mL) and developed with NBT/BCIP substrate. Detection limits were ~1 fmole (300 pg) for either toxin A and B with aptamers. Monoclonal antibodies used for the same assay and at the same concentration (1 nM) were not as good, but were able to detect 2 fmoles (600 pg) of toxin A and 20 fMoles (6 ng) of toxin B.

Example 9

Figure 8:
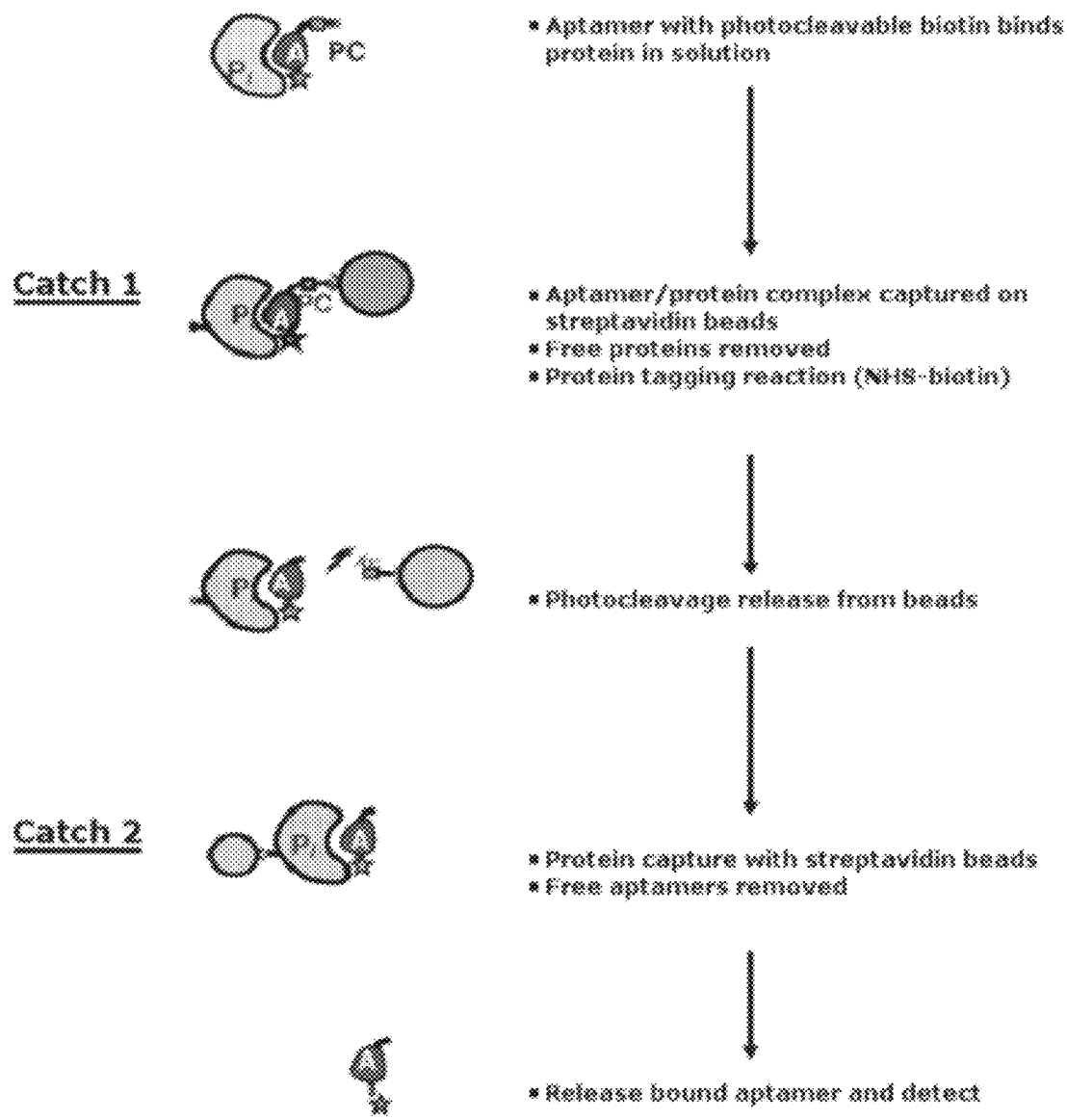
FIG. 8 illustrates relevant steps of a Catch 1-Catch 2 assay.

Use of Aptamers for Toxin A/B and Binary Toxin as Diagnostic Reagents: Catch 1 & 2 Assay with qPCR Detection A Catch 1-Catch 2 assay is illustrated at FIG. 8. Toxins A and B were detected quantitatively via qPCR of catch 2 eluates (FIG. 4A-B). In catch 1, spiked samples containing toxin (0.001-10 nM) and excess BSA (1.5 μM) were equilibrated with aptamers comprising a photocleavable biotin-D spacer (10 nM) and captured on streptavidin agarose beads (relatively clear beads which allow light to pass through). After wash removal of free protein, the toxin (target) of the catch 1 samples was tagged with NHS-biotin, aptamers were photocleaved off the streptavidin agarose beads and complexes were captured on MyOne streptavidin beads (catch 2). Since after photocleavage the photocleavable biotin-D spacer could no longer mediate binding to the MyOne streptavidin beads, in catch 2 the binding to the MyOne streptavidin beads was mediated by the NHS-biotin on the toxin (target). After wash removal of free aptamers, the target-bound aptamers were eluted at high pH and used for qPCR; standard curves for the aptamers were run side-by-side. Quantitative results for toxin A and B were obtained at concentrations of >0.1 nM only. There was non-specific background at the lower target concentrations, and pPCR curves reached a plateau after less than 12 cycles. This was most likely due to considerable carry-over of free aptamers during catch 1 and 2, and due to a rather high (10 nM) aptamer concentration.

Example 10

Figure 5A:
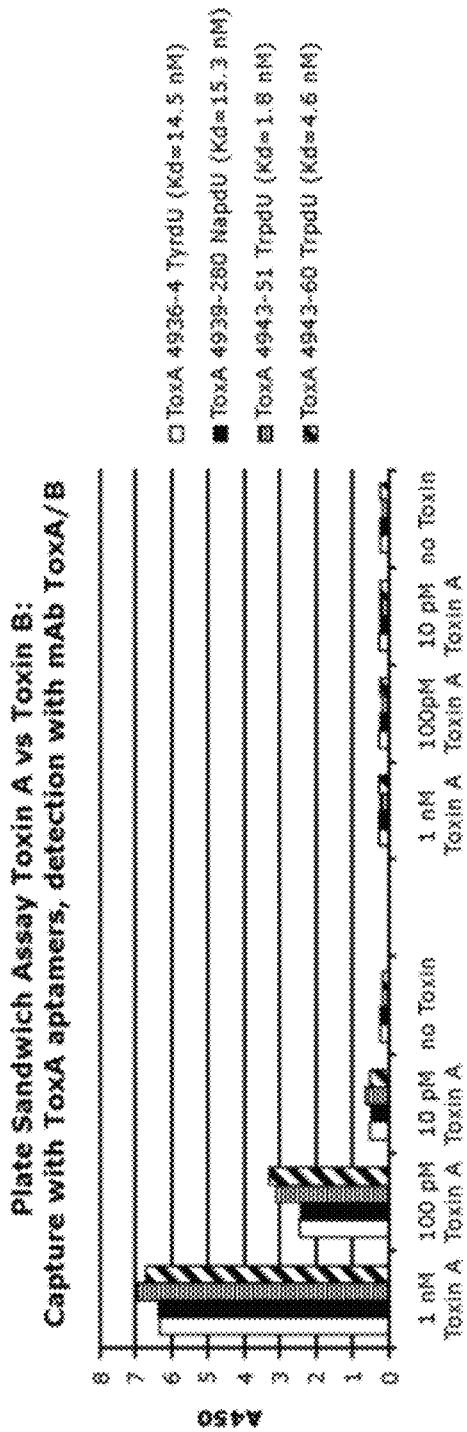
FIG. 5A illustrates results of detection of *C. difficile* toxin A via streptavidin plate sandwich (aptamer-target-antibody) assay, using biotinylated aptamers to toxin A and mouse monoclonal antibodies to toxin A detected with goat-anti-mouse antibodies.
Figure 5B:
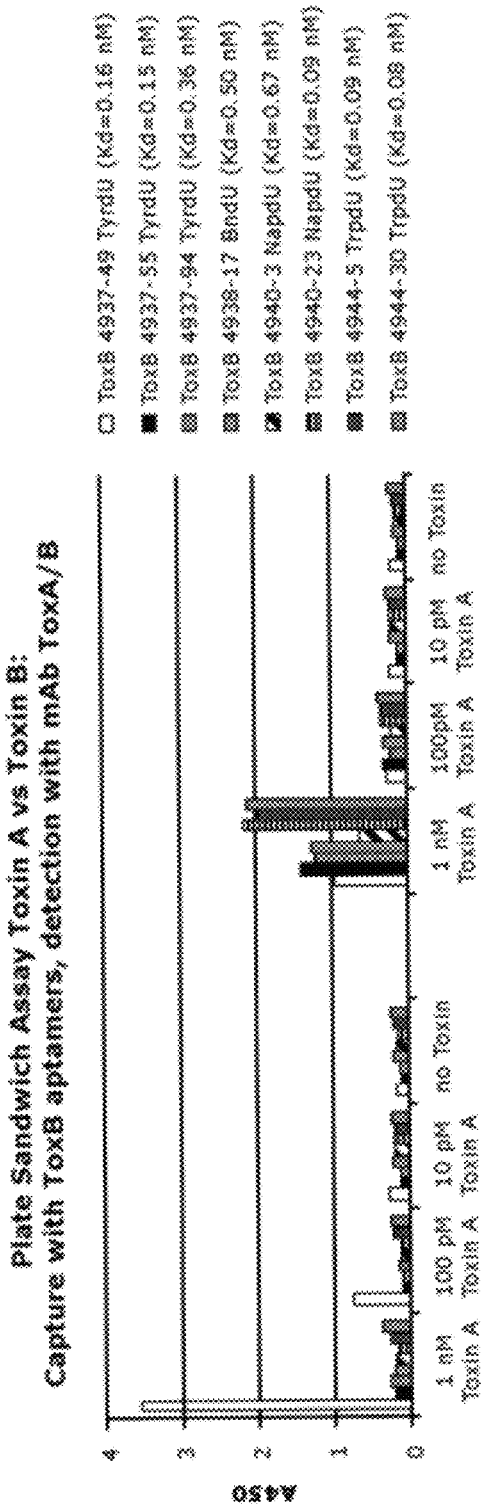
FIG. 5B illustrates results of detection of *C. difficile* toxin B via streptavidin plate sandwich (aptamer-target-antibody) assay, using biotinylated aptamers to toxin B and mouse monoclonal antibodies to toxin B detected with goat-anti-mouse antibodies.

Use of Aptamers for Toxin A/B and Binary Toxin as Diagnostic Reagents: Aptamer-Target-Antibody Sandwich Assay Toxins were detected in streptavidin plate sandwich assay, using biotinylated aptamers and monoclonal antibodies (FIG. 5A-B).

Toxin detection was demonstrated for toxins A and B. Biotinylated aptamers (1 pmole/well) were immobilized on a streptavidin plate, and target proteins were added (1 nM, 100 pM, 10 pM, no protein), corresponding to 100 fMoles (30 ng), 10 fMoles (3 ng), 1 fMole (300 pg), and no protein control. The plates were washed and monoclonal antibodies to Toxin A or B (2 nM each) were added and allowed to bind for 1 h with shaking at RT. Complexes were detected with goat-anti-mouse HRP conjugate and TMB as HRP substrate (FIGS. 5A and 5B).

The sandwich assay produced robust results with target concentration-dependent signals and low background. All four toxin A aptamers were able to detect 10 μM toxin A (1 fMole, 300 pg) regardless of their $K_d$ and did not cross-react with toxin B. Aptamers for toxin B, in spite of better $K_d$'s, had poor sensitivity in this assay, possibly due to overlapping binding sites of the aptamer and antibody. One of the toxin B aptamers (4937-49) did cross-react with toxin A, which is consistent with data from pull-down experiments.

Example 11

Figure 6:
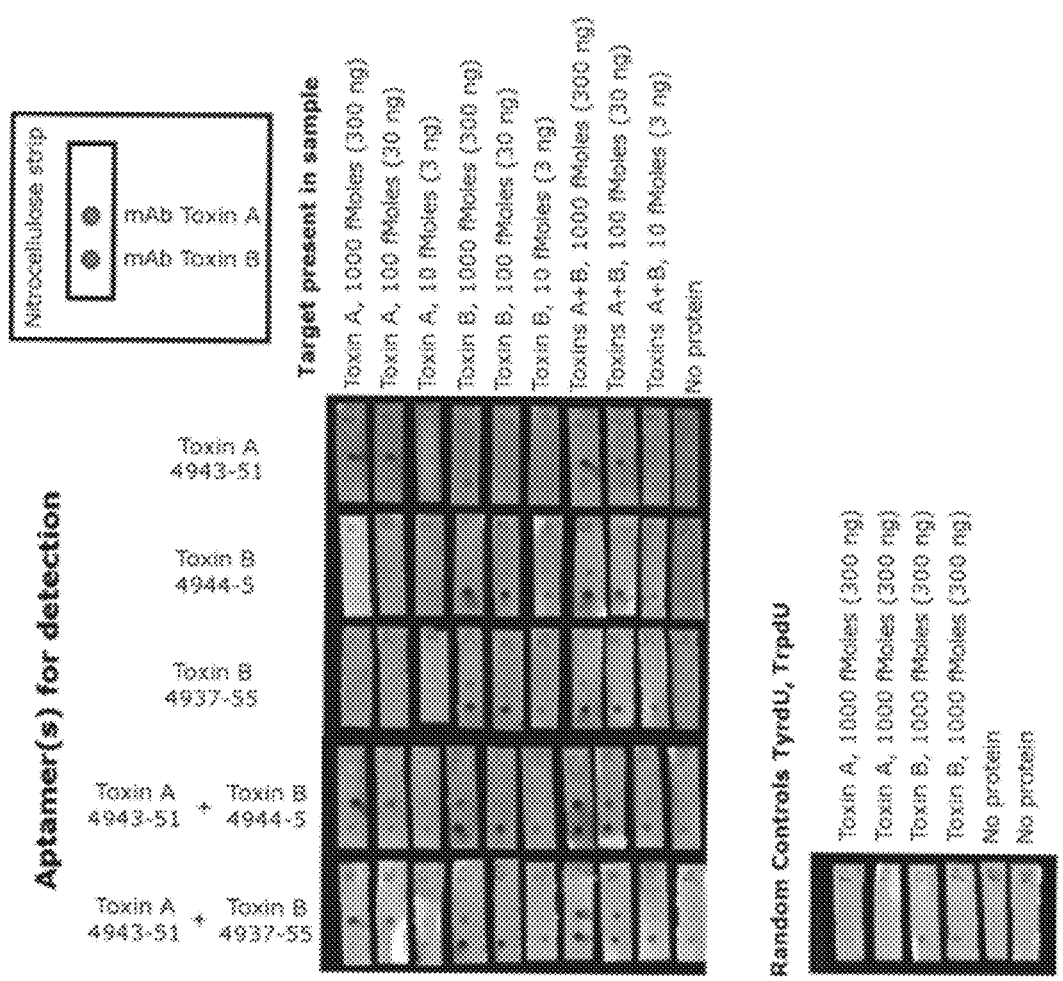
FIG. 6 illustrates results of detection of *C. difficile* toxin A and B via sandwich (antibody-target-aptamer) assays on nitrocellulose, wherein monoclonal antibodies are spotted onto nitrocellulose and air dried, blocked, samples containing toxin A or B added, washed, biotinylated aptamers added, washed, and developed with streptavidin-alkaline phosphatase conjugate.

Use of Aptamers for Toxin A/B and Binary Toxin as Diagnostic Reagents: Antibody-Target-Aptamer Sandwich Assay Aptamers were used for the detection of toxins in antibody-aptamer sandwich assays, e.g. in a dipstick-type assay format, using biotinylated aptamers and monoclonal antibodies (FIG. 6).

Monoclonal antibodies to toxin A and B were spotted separately on a small (0.6 cm×2.5 cm) strip of nitrocellulose and air-dried. After blocking with SB18T+1% BSA, the strips were placed upright in a deep well plate and 0.6 mL samples containing toxin A and/or toxin B or controls were added. After shaking for 1 h at RT, the strips were washed 3×. Biotinylated aptamers (1 nM) were added (0.6 mL) and allowed to bind for 1 h at RT. The strips were washed again and developed with 1 nM streptavidin-alkaline phosphatase conjugate (1 h) and NBT/BCIP (FIG. 6).

The toxin A aptamer 4943-51 detected toxin A accurately in all samples containing only toxin A or both toxins A and B (1000 fMoles or 100 fMoles), and did not cross-react with toxin B. Similarly, toxin B aptamers were able to detect toxin B. Background was high especially in the toxin B spot, even when no protein was present in the sample and when random control aptamers were used, suggesting non-specific binding of the streptavidin-alkaline phosphatase conjugate to the toxin B monoclonal antibody.

Example 12

Use of Aptamers for Toxin A/B and Binary Toxin as Diagnostic Reagents: Aptamer-Target-Aptamer Sandwich Assay Aptamers were used for the detection of toxins in aptamer-aptamer sandwich assays, e.g. in a bead-based assay format using a pair of aptamers, without the need of any antibodies (FIG. 7).

Capture beads were prepared by attaching the first, biotinylated aptamer (clone 4758-6) to MyOne™ streptavidin beads. A sample containing target protein (CdtA) in serial dilutions was added, and CdtA was allowed to bind to these capture beads. After washing the beads, a second, radiolabeled CdtA aptamer clone was added for equilibrium binding. Then the mixture was filtered through MAHVN plates (0.22μ), using the capture beads themselves for partitioning. This method will detect only labeled aptamers that are bound in sandwich-type format to the streptavdin-aptamer 4758-6-CdtA complex.

Figure 7:
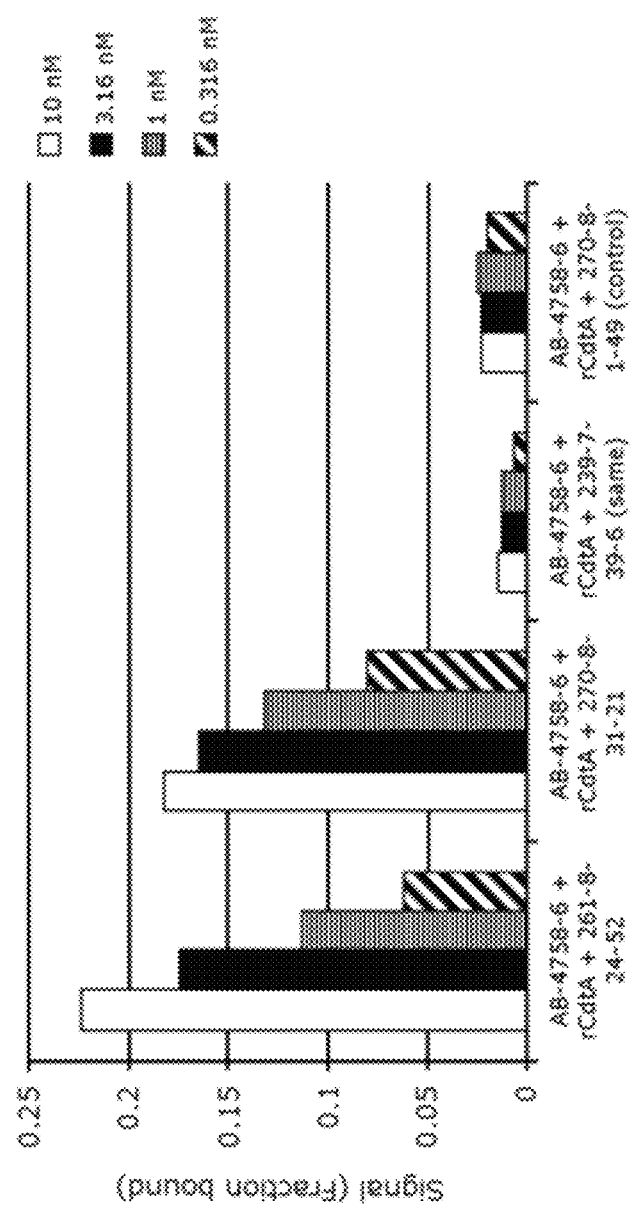
FIG. 7 illustrates results of detection of *C. difficile* binary toxin A chain in a sandwich (aptamer-target-aptamer) assay with a first biotinylated aptamer to binary toxin A chain attached a streptavidin bead, addition of target, and addition of a second, radiolabeled aptamer to binary toxin A chain.

The results of the capture bead assay for CdtA aptamer pairs are shown in FIG. 7. Suitable pairs of aptamers produced target concentration-dependent signals. No signals were produced if the same aptamer (binding to the same epitope) or a control aptamer (binding to a different target) was used.

This assay can be used to screen aptamers for binding to distinct epitopes on the target, that is, each aptamer binding to a separate site, as opposed to competing for the same epitope.

What is claimed is:

1. A method of detecting the presence of *C. difficile* toxin in a test sample comprising contacting said test sample with an aptamer that binds to *C. difficile* toxin B wherein said aptamer comprises a sequence selected from the group consisting of SEQ ID NOS: 67-71.

2. The method of claim 1, wherein said aptamer further comprises at least one addition chemical modification, wherein said at least one addition chemical modification is a chemical substitution at one or more position independently selected from the group consisting of a ribose position, a deoxyribose position, a phosphate position, and a base position.

3. The method of claim 2, wherein said at least one additional chemical modification is independently selected from the group consisting of a 2'-amino (2'-$NH_2$), a 2'-fluoro (2'-F), a 2'-O-methyl (2'-Ome), a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap.

4. The method of claim 1, wherein said aptamer comprises a $K_d$ for *C. difficile* toxin B of 30 nM or less.

5. The method of claim 1, wherein said aptamer is nuclease resistant.

6. The method claim 1, wherein said aptamer has a slow off rate.

* * * * *